(12) United States Patent
Otsuki et al.

(10) Patent No.: US 11,322,695 B2
(45) Date of Patent: May 3, 2022

(54) INK COMPOSITION FOR ORGANIC LIGHT-EMITTING DEVICE, ORGANIC LIGHT-EMITTING DEVICE INCLUDING FILM FORMED BY USING THE INK COMPOSITION, AND METHOD OF MANUFACTURING THE ORGANIC LIGHT-EMITTING DEVICE

(71) Applicants: SAMSUNG ELECTRONICS CO., LTD., Suwon-si (KR); DIC Corporation, Tokyo (JP)

(72) Inventors: Eiji Otsuki, Sakura (JP); Masanori Wakita, Sakura (JP); Fumiaki Kato, Kanagawa (JP); Satoshi Inayama, Kanagawa (JP); Norihito Ishii, Kanagawa (JP); Katsunori Shibata, Kanagawa (JP); Mitsunori Ito, Kanagawa (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/887,208

(22) Filed: May 29, 2020

(65) Prior Publication Data

US 2020/0295273 A1    Sep. 17, 2020

Related U.S. Application Data

(62) Division of application No. 15/647,609, filed on Jul. 12, 2017, now abandoned.

(30) Foreign Application Priority Data

Jul. 12, 2016 (JP) .......................... JP2016-0137892

(51) Int. Cl.
| | |
|---|---|
| C07C 43/18 | (2006.01) |
| C07C 49/213 | (2006.01) |
| C07C 69/612 | (2006.01) |
| C07D 209/82 | (2006.01) |
| C09D 11/38 | (2014.01) |
| C09D 11/52 | (2014.01) |
| H01L 51/00 | (2006.01) |

(52) U.S. Cl.
CPC ........ *H01L 51/0072* (2013.01); *C07D 209/82* (2013.01); *C09D 11/38* (2013.01); *C09D 11/52* (2013.01); *H01L 51/0007* (2013.01); *C07C 43/18* (2013.01); *C07C 49/213* (2013.01); *C07C 69/612* (2013.01)

(58) Field of Classification Search
CPC .............. C07D 209/82; H01L 51/0072; H01L 51/0007; C09D 11/52; C09D 11/38
See application file for complete search history.

(56) References Cited

U.S. PATENT DOCUMENTS

| | | |
|---|---|---|
| 8,174,000 B2 | 5/2012 | Cheon et al. |
| 9,331,295 B2 | 5/2016 | Watanabe et al. |
| 9,653,685 B2 | 5/2017 | Watanabe |
| 9,705,091 B2 | 7/2017 | Ikeda et al. |
| 10,276,637 B2 | 4/2019 | Matsumoto et al. |
| 2004/0225056 A1 | 11/2004 | Spreitzer et al. |

(Continued)

FOREIGN PATENT DOCUMENTS

| | | |
|---|---|---|
| EP | 2746273 A1 | 6/2014 |
| EP | 2991128 A1 | 3/2016 |

(Continued)

OTHER PUBLICATIONS

Chemical Book, CAS Data Base List—Anisole, 2017 [retrieved on Jul. 11, 2019]. Retrieved from the Internet<URL:https:// www.chemicalbook.com/ChemicalProductProperty_EN_CB5100716.htm>]. (Year: 2017).

(Continued)

*Primary Examiner* — Amanda L. Aguirre
(74) *Attorney, Agent, or Firm* — Cantor Colburn LLP

(57) ABSTRACT

An ink composition for an organic light-emitting device, the ink composition including a luminescent host material and a solvent, wherein the luminescent host material includes at least one compound represented by Formula (1) and Formula (3), and wherein the solvent includes at least one selected from an aromatic ether, an aromatic ester, and an aromatic ketone:

Formula (1)

$(A_1)$—$(L_1)_{a1}$—[carbazole]—$(L_3)_{a3}$—$(A_3)$,
$(L_2)_{a2}$—$(A_2)$

Formula (3)

$(A_1)$—$(L_1)_{a1}$—[bicarbazole]—$(L_{63})_{a63}$—$(A_3)$
$(L_2)_{a2}$—$(A_2)$ wherein, in Formulas (1) and (3), groups and variables are the same as described in the specification.

15 Claims, 1 Drawing Sheet

(56) References Cited

U.S. PATENT DOCUMENTS

| | | |
|---|---|---|
| 2009/0302752 A1 | 12/2009 | Parham et al. |
| 2010/0200841 A1 | 8/2010 | Cheon et al. |
| 2011/0101328 A1 | 5/2011 | Kaiser et al. |
| 2013/0240796 A1* | 9/2013 | Parham .............. H01L 51/0072 252/500 |
| 2013/0306959 A1 | 11/2013 | Ikeda et al. |
| 2014/0159023 A1 | 6/2014 | Matsumoto et al. |
| 2015/0214489 A1 | 7/2015 | Parham et al. |
| 2015/0228908 A1 | 8/2015 | Lee et al. |
| 2015/0340621 A1* | 11/2015 | Parham ............... C09K 11/025 257/40 |
| 2016/0072078 A1 | 3/2016 | Lee et al. |
| 2016/0329505 A1* | 11/2016 | Ikeda .................. H01L 51/0072 |
| 2017/0018719 A1* | 1/2017 | Kawakami .......... H01L 51/0072 |
| 2017/0125676 A1 | 5/2017 | Anemian et al. |
| 2017/0338427 A1 | 11/2017 | Otsuki et al. |
| 2018/0019411 A1 | 1/2018 | Otsuki et al. |

FOREIGN PATENT DOCUMENTS

| | | |
|---|---|---|
| EP | 3184522 A1 | 6/2017 |
| JP | 2004535653 A | 11/2004 |
| JP | 2011198544 A | 10/2011 |
| JP | 2012517673 A | 8/2012 |
| JP | 2013131574 A | 7/2013 |
| JP | 201477046 A | 5/2014 |
| JP | 2015079609 A | 4/2015 |
| JP | 2015185640 A | 10/2015 |
| JP | 2015530363 A | 10/2015 |
| JP | 5837051 B2 | 11/2015 |
| JP | 2015191792 A | 11/2015 |
| JP | 2017114858 A | 6/2017 |
| JP | 2018009078 A | 1/2018 |
| KR | 1020150094398 A | 8/2015 |
| KR | 1020160026744 A | 3/2016 |
| KR | 2017114858 A | 6/2017 |
| KR | 1020170074811 A | 6/2017 |
| WO | 2006025186 A1 | 3/2006 |
| WO | 2012147208 A1 | 11/2012 |
| WO | 2012157211 A1 | 11/2012 |
| WO | 2013146117 A1 | 10/2013 |
| WO | 2014015931 A1 | 1/2014 |
| WO | 2016093111 A1 | 6/2016 |
| WO | 2018230548 A1 | 12/2018 |

OTHER PUBLICATIONS

Extended Search Report issued by the European Patent Office dated Nov. 29, 2017, with English Translation.

Office Action issued by the European Patent Office dated Dec. 10, 2018, in the examination of the European Patent Application No. 17180927.0.

PubChem Database, CID: 7519 "Anisole", Create Date: Sep. 16, 2004. (Year: 2004).

Royal Society of Chemistry ChemSpider Entry No. 2681 "4-Methoxytoluene" [retrieved online on Sep. 23, 2019][retrieved from: http://www.chemspider.com/Chemical-Structure.13865438.html]. (Year: 2019).

Sigma-Aldrich Product No. 148091 "4-Methylanisole" Safety Data Sheet, print date: Aug. 7, 2019 [retrieved online on Sep. 19, 2019][retrieved from https://www.sigmaaldrich.com]. (Year: 2019).

ThermoFischer Scientific Cat. No. AC164660000 "4-Methylanisole" Safety Data Sheet, print date: Jan. 18, 2018 [retrieved online on Sep. 23, 2019][retrieved from https://www.fishersci.com/], (Year: 2018).

Office Action issued by the Japanese Patent Office dated Mar. 24, 2020 in the examination of the Japanese Patent Application No. 2016-137892, which corresponds to the U.S. Application above.

English Translation of Office Action issued by the Japanese Patent Office dated Mar. 24, 2020 in the examination of the Japanese Patent Application No. 2016-137892, which corresponds to the U.S. Application above.

English Translation of Office Action dated Jul. 28, 2021 in KR Patent Application No. 10-2017-0088659.

Office Action dated Jul. 28, 2021 in KR Patent Application No. 10-2017-0088659.

English Translation of Office Action dated Dec. 15, 2021 issued in JP Patent Application No. 2016-137892, 9 pp.

Office Action dated Dec. 15, 2021 issued in JP Patent Application No. 2016-137892, 7 pp.

\* cited by examiner

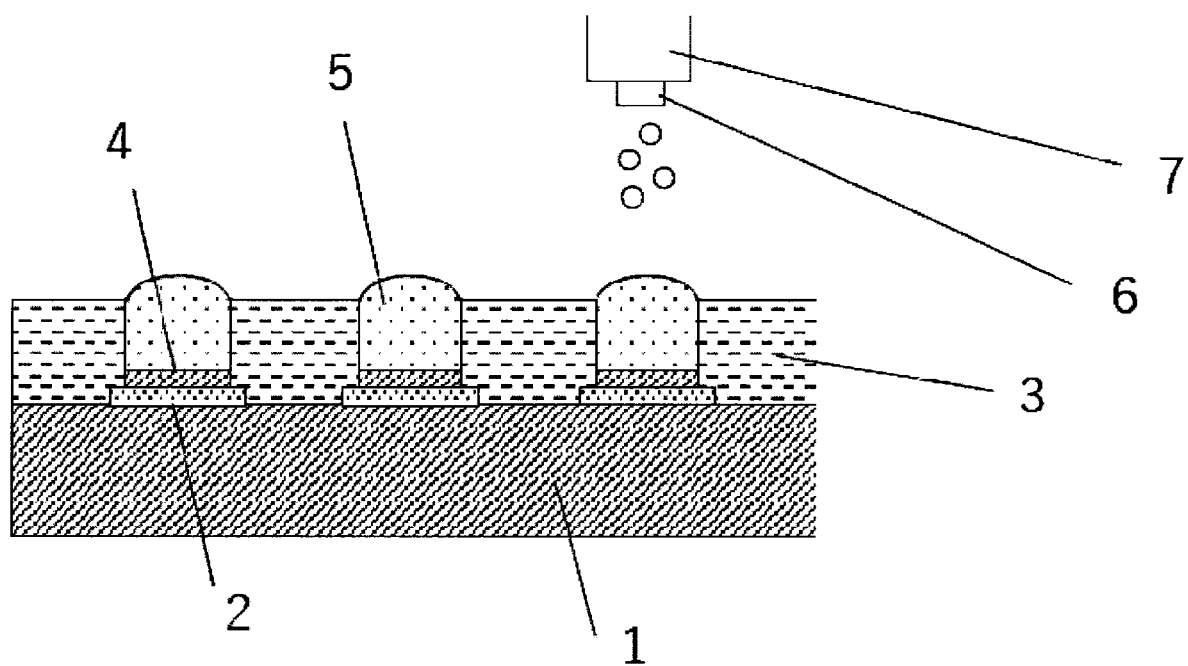

INK COMPOSITION FOR ORGANIC LIGHT-EMITTING DEVICE, ORGANIC LIGHT-EMITTING DEVICE INCLUDING FILM FORMED BY USING THE INK COMPOSITION, AND METHOD OF MANUFACTURING THE ORGANIC LIGHT-EMITTING DEVICE

CROSS-REFERENCE TO RELATED APPLICATION

This application is a divisional of U.S. patent application Ser. No. 15/647,609, filed Jul. 12, 2012, which claims priority to Japanese Patent Application No. 2016-0137892, filed on Jul. 12, 2016, in the Japanese Patent Office, and all the benefits accruing therefrom under 35 U.S.C. § 119, the disclosure of both applications being incorporated herein in their entirety by reference.

BACKGROUND

1. Field

One or more embodiments relate to an ink composition for an organic light-emitting device, an organic light-emitting device including a film formed by using the ink composition, and a method of manufacturing the organic light-emitting device.

2. Description of the Related Art

In general, an organic light-emitting device (OLED) includes an anode, a hole transport layer, an emission layer, an electron transport layer, and a cathode. When an electric field is applied to the organic light-emitting device, holes are injected from the anode to the hole transport layer, and electrons are injected from the cathode to the electron transport layer. The holes and the electrons then move toward the emission layer and recombine in the emission layer to generate energy. The generated energy causes a light-emitting material in the emission layer to emit light. In some cases, the organic light-emitting device may not include the hole transport layer and/or the electron transport layer. Furthermore, the organic light-emitting device may further include a hole injection layer and an electron injection layer.

The constituting layers of the organic light-emitting device are generally formed by using dry deposition or wet deposition.

In the dry deposition, a deposition film is formed by heating and evaporating an organic material in a vacuum environment. In the wet deposition, a film is formed by coating a coating composition (for example, an ink composition) including an organic material and drying the coated film obtained therefrom.

Recently, wet deposition, for example, inkjet printing, has attracted attention due to its use in high-resolution patterning and its high material utilization efficiency. There still remains a need in the art for an ink composition possessing optimal properties to be used in an organic light-emitting device.

SUMMARY

Aspects of the present disclosure provide an ink composition for an organic light-emitting device, which has excellent inkjet discharge stability and is capable of realizing high light emission efficiency, an organic light-emitting device including a film formed by using the ink composition, and a method of manufacturing the organic light-emitting device.

Additional aspects will be set forth in part in the description which follows and, in part, will be apparent from the description, or may be learned by practice of the presented embodiments.

The inventors of the subject matter of the present application found that the above problems could be solved by using at least one compound selected from an aromatic ether, an aromatic ester, and an aromatic ketone, with respect to an organic host material having a certain structure.

An aspect of the present disclosure provides an ink composition for an organic light-emitting device, the ink composition including a luminescent host material and a solvent, wherein the luminescent host material includes at least one compound represented by Formula (1), and wherein the solvent includes at least one selected from an aromatic ether, an aromatic ester, and an aromatic ketone:

Formula (1)

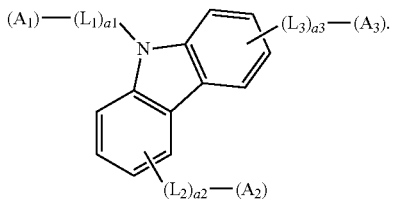

In Formula (1), $L_1$ to $L_3$ may each independently be selected from a single bond, *—O—*', *—S—*', *—N($R_5$)—*', a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a3 may each independently be an integer from 1 to 10, $A_1$ to $A_3$ may each independently be selected from hydrogen, deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_1)(Q_2)$, and $-C(=O)(Q_1)$, any neighboring groups in $A_1$ to $A_3$ may optionally be linked to form a substituted or unsubstituted $C_5$-$C_{30}$ carbocyclic group or a substituted or unsubstituted $C_2$-$C_{30}$ heterocyclic group, provided that $*$-$(L_2)_{a2}$-$(A_2)$ and $*$-$(L_3)_{a3}$-$(A_3)$ in Formula (1) are not hydrogen at the same time, at least one substituent of the substituted $C_2$-$C_{60}$ alkylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_5$-$C_{30}$ carbocyclic group, and the substituted $C_2$-$C_{30}$ heterocyclic group may be selected from:

deuterium, $-F$, $-Cl$, $-Br$, $-I$, $-CD_3$, $-CD_2H$, $-CDH_2$, $-CF_3$, $-CF_2H$, $-CFH_2$, $-NCS$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, $-F$, $-Cl$, $-Br$, $-I$, $-CD_3$, $-CD_2H$, $-CDH_2$, $-CF_3$, $-CF_2H$, $-CFH_2$, $-NCS$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{11})(Q_{12})(Q_{13})$, $-N(Q_{11})(Q_{12})$, and $-C(=O)(Q_{11})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, $-F$, $-Cl$, $-Br$, $-I$, $-CD_3$, $-CD_2H$, $-CDH_2$, $-CF_3$, $-CF_2H$, $-CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-Si(Q_{21})(Q_{22})(Q_{23})$, $-N(Q_{21})(Q_{22})$, and $-C(=O)(Q_{21})$; and $-Si(Q_{31})(Q_{32})(Q_{33})$, $-N(Q_{31})(Q_{32})$, and $-C(=O)(Q_{31})$, and $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

Another aspect of the present disclosure provides an organic light-emitting device including:
an anode;
an emission layer; and
a cathode,
wherein the emission layer is an organic film formed by using the ink composition described above,
wherein the emission layer includes a luminescent host material, and
wherein the luminescent host material includes at least one compound represented by Formula (1).

Another aspect of the present disclosure provides a method of manufacturing an organic light-emitting device, the method including:
forming an anode on a substrate;
forming an emission layer including the luminescent host material by coating the ink composition for an organic light-emitting device on the anode and drying the obtained coating film; and
forming a cathode on the emission layer.

BRIEF DESCRIPTION OF THE DRAWING

These and/or other aspects will become apparent and more readily appreciated from the following description of the embodiments, taken in conjunction with the FIGURE which is a schematic partial cross-sectional view for describing a method of forming a coating film by using inkjet printing.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Hereinafter, various embodiments of the present disclosure will be described in detail with reference to the accompanying drawings.

Ink Composition for Organic Light-Emitting Device

An ink composition for an organic light-emitting device, according to an embodiment, may include a luminescent host material and a solvent, wherein the luminescent host material may include at least one compound represented by Formula (1). The ink composition may, if necessary, further include other luminescent impurities (for example, a dopant for use in an emission layer of an organic light-emitting device), an additive, and the like. The term "light emission" or "luminescence" as used herein includes a light emission caused by fluorescence and light emission caused by phosphorescence.

The ink composition for an organic light-emitting device has excellent inkjet discharge stability, and accordingly, an organic light-emitting device, which includes a film formed by using the ink composition for an organic light-emitting device, may have high luminescent efficiency. While not wishing to be bound by any theory, the reason for this is understood to be due to a mechanism to be described below. Also, since the ink composition for an organic light-emitting device has excellent inkjet discharge stability, it may be used as an ink composition for inkjet printing.

Although not limited by a specific theory, when a composition A that includes a luminescent host material including at least one compound represented by Formula (1) and an aliphatic ether solvent, compatibility between the luminescent host material and the aliphatic ether solvent is insufficient, and thus, aggregation of the luminescent host material may occur in the composition A. Therefore, when inkjet printing is performed by using the composition A, the luminescent host material may precipitate around an inkjet nozzle, and inkjet discharge stability may be reduced due to a deterioration in straightness of droplets. Also, the aggregation of droplets of the composition A attached on a support accelerates when dried, resulting in a reduction in luminescent efficiency of an organic light-emitting device including a film formed by using the composition A.

However, unlike the composition A described above, the ink composition for an organic light-emitting device uses at least one compound selected from an aromatic ether, an aromatic ester, and an aromatic ketone as a solvent, and accordingly, compatibility between the luminescent host material including the compound represented by Formula (1) and the solvent may be improved. Also, since an aromatic group and an ether group or a carbonyl group in the solvent relaxes a stacking interaction of the luminescent host material, the aggregation of the luminescent host material may be suppressed. Thus, the ink composition for an organic light-emitting device has excellent inkjet discharge stability, and luminescent efficiency of an organic light-emitting device including a film formed by the ink composition may be improved.

The above-described mechanism is merely a presumption, and even if the effects of the present disclosure are obtained by other mechanisms, they fall within the technical scope of the present disclosure.

Luminescent Host Material

The luminescent host material may be used in an organic layer of an organic light-emitting device for various purposes.

For example, the luminescent host material may be used for a luminescent host in an emission layer of an organic light-emitting device.

The luminescent host may have a function of transporting holes and electrons injected into the emission layer.

The luminescent host material may include at least one compound represented by Formula (1):

Formula (1)

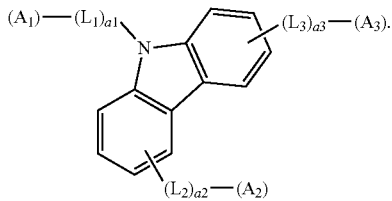

In Formula (1), $L_1$ to $L_3$ may each independently be selected from a single bond, *—O—*', *—S—*', *—N($R_5$)—*', a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{00}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a3 may each independently be an integer from 1 to 10, $A_1$ to $A_3$ may each independently be selected from hydrogen, deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —C(=O)($Q_1$), any neighboring groups in $A_1$ to $A_3$ may optionally be linked to form a substituted or unsubstituted $C_5$-$C_{30}$ carbocyclic group or a substituted or unsubstituted $C_2$-$C_{30}$ heterocyclic group, provided that *-($L_2$)$_{a2}$-($A_2$) and *-($L_3$)$_{a3}$-($A_3$) in Formula (1) are not hydrogen at the same time, at least one substituent of the substituted $C_2$-$C_{60}$ alkylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_5$-$C_{30}$ carbocyclic group, and the substituted $C_2$-$C_{30}$ heterocyclic group may be selected from:

deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), and —C(=O)($Q_{11}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), and —C(=O)($Q_{21}$); and —Si($Q_{31}$)($Q_{32}$)($Q_{33}$), —N($Q_{31}$)($Q_{32}$), and —C(=O)($Q_{31}$), $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

A "hydrogen atom" also includes a deuterium atom.

The term "$C_1$-$C_{60}$ alkyl group" as used herein refers to a linear or branched saturated aliphatic hydrocarbon monovalent group having 1 to 60 carbon atoms. The term "$C_1$-$C_{60}$ alkylene group" as used herein refers to a divalent group having the same structure as the $C_1$-$C_{60}$ alkyl group.

The term "$C_3$-$C_{10}$ cycloalkyl group" as used herein refers to a monovalent saturated hydrocarbon monocyclic group having 3 to 10 carbon atoms. The term "$C_3$-$C_{10}$ cycloalkylene group" as used herein refers to a divalent group having the same structure as the $C_3$-$C_{10}$ cycloalkyl group.

Examples of the substituted or unsubstituted alkyl group and the substituted or unsubstituted cycloalkyl group may include:

a linear alkyl group such as a methyl group, an ethyl group, a propyl group, an n-pentyl group, an n-hexyl group, an n-heptyl group, an n-octyl group, an n-nonyl group, an n-decyl group, a n-undecyl group, an-undecyl group, an n-tridecyl group, an n-tetradecyl group, an n-pentadecyl group, an n-hexadecyl group, an n-heptadecyl group, and an n-octadecyl group;

a branched alkyl group such as an iso-propyl group, an n-butyl group, an iso-butyl group, an s-butyl group, and a t-butyl group; and a cyclic alkyl group such as a cyclopentyl group, a cyclohexyl group, a cycloheptyl group, and a cyclooctyl group.

Among them, an alkyl group or a cycloalkyl group having 1 to 10 carbon atoms, for example, a methyl group, an ethyl group, a propyl group, an iso-propyl group, an n-butyl group, an iso-butyl group, an s-butyl group, a t-butyl group, a cyclopentyl group, a cyclohexyl group, and a cycloheptyl group may be used.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group. The term "$C_2$-$C_{60}$ alkenylene group" as used herein refers to a divalent group having the same structure as the $C_2$-$C_{60}$ alkenyl group.

The term "$C_3$-$C_{10}$ cycloalkenyl group" as used herein refers to a monovalent monocyclic group that has 3 to 10 carbon atoms and at least one carbon-carbon double bond in the ring thereof, that is non-aromatic. The term "$C_3$-$C_{10}$ cycloalkenylene group" as used herein refers to a divalent group having the same structure as the $C_3$-$C_{10}$ cycloalkenyl group.

Examples of the substituted or unsubstituted alkenyl group and the substituted or unsubstituted cycloalkenyl group may include:

a linear alkenyl group such as a vinyl group, a propenyl group, a butenyl group, a pentenyl group, a hexenyl group, a heptenyl group, an octenyl group, a nonenyl group, a decenyl group, a dodecenyl group, a tetradecenyl group, a hexadecenyl group, and an octadecenyl group;

a branched alkenyl group such as a methylpentenyl group; and a cyclic alkenyl group such as a cyclohexenyl group, a cycloheptenyl group, or a 4-methylcyclohexane group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group. The term "$C_2$-$C_{60}$ alkynylene group" as used herein refers to a divalent group having the same structure as the $C_2$-$C_{60}$ alkynyl group.

Examples of the substituted or unsubstituted alkynyl group may include ethynyl group, a 1-prophynyl group, a 2-propynyl group, a 1-butynyl group, a 1-pentynyl group, a 1-hexynyl group, a 1-heptynyl group, a 1-octynyl group, a 1-nonynyl group, a 1-decynyl group, a 1-untadecynyl group, a 1-dodecynyl group, a 1-tridecynyl group, a 1-tetradecynyl group, a 1-pentadecynyl group, a 1-hexadecynyl group, 1-heptadecynyl group, a 1octadecynyl group, and a 1-nonadecynyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. When the $C_6$-$C_{60}$ aryl group and the $C_6$-$C_{60}$ arylene group each include two or more rings, the rings may be fused to each other.

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in the entire molecular structure. The term "divalent non-aromatic condensed polycyclic group," as used herein, refers to a divalent group having the same structure as the monovalent non-aromatic condensed polycyclic group.

Examples of the substituted or unsubstituted aryl group and the substituted or unsubstituted monovalent non-aromatic condensed polycyclic group may include a phenyl group, a biphenyl group, a terphenyl group, a naphthyl group, an anthranyl group, a phenanthryl group, a phenylterphenyl group, a pyrenyl group, a chrysenyl group, a fluorenyl group, a 9,9-dimethylfluorenyl group, a bisphenylfluorenyl group, a (9-fluorenyl)fluorenyl group, a spiro-fluorenyl group, and a fluoranthenyl group. Examples of the substituent of the substituted aryl group and the substituted monovalent non-aromatic condensed polycyclic group may be selected from an alkyl group, an alkenyl group, an alkynyl group, an alkoxy group, an aryloxy group, a halogen group, and a cyano group.

The term "$C_1$-$C_{60}$ heteroaryl group" as used herein refers to a monovalent group having an aromatic system that has at least one heteroatom selected from N, O, P, Si, and S as a ring-forming atom, and 1 to 60 carbon atoms. The term "$C_1$-$C_{60}$ heteroarylene group" as used herein refers to a divalent group having an aromatic system that has at least one heteroatom selected from N, O, P, Si, and S as a ring-forming atom, and 1 to 60 carbon atoms. When the $C_1$-$C_{60}$ heteroaryl group and the $C_1$-$C_{60}$ heteroarylene group each include two or more rings, the rings may be fused to each other.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in the entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

Examples of the substituted or unsubstituted heteroaryl group and the substituted or unsubstituted monovalent non-aromatic condensed heteropolycyclic group may include a monovalent group that is formed by removing a hydrogen atom from a thiophene group, a thiazole group, a furan group, an oxazole group, a pyran group, a pyrrole group, an imidazole group, a pyrazole group, an isothiazole group, an isoxazole group, a furazan group, a triazole group, a pyridine group, a pyrazine group, a pyrimidine group, a pyridazine group, a triazine group, a bipyrimidine group, a bipyridazine group, a bitriazine group, a phenylpyrimidine group, a diphenylpyrimidine group, a triphenylpyrimidine group, a phenylpyridazine group, a diphenylpyridazine group, a triphenylpyridazine group, a phenyltriazine group, a diphenyltriazine group, a triphenyltriazine group, a pyrimidinylterphenyl group, a pyridazinylterphenyl group, a triazinylterphenyl group, a benzothiophene group, a benzothiazole group, a thianthrene group, an iso-benzofuran group, a benzoxazole group, a chromene group, a xanthene group, a phenoxanthin group, an indolidine group, an isoindole group, an indole group, a benzimidazole group, an indazole group, a benzotriazole group, a purine group, a quinolizine group, an isoquinoline group, a quinoline group, a phthalazine group, a naphthylidine group, a quinoxaline group, a quinazoline group, a cinnoline group, a pteridine group, a carbazole group, a carboline group, a phenanthridine group, an acridine group, a perimidine group, a phenanthroline group, a phenazine group, a phenothiazine group, a phenoxazine group, a dibenzodioxin group, a pyrimidobenzothiophene group, a phenylpyrimidobenzothiophene group, a diphenypyrimidobenzothiophene, a dibenzofuran group, or a dibenzothiophene group. For example, the substituted or unsubstituted heteroaryl group and the substituted or unsubstituted monovalent non-aromatic condensed heteropolycyclic group may be a monovalent group that is formed by removing a hydrogen atom from a pyridine group, a pyrazine group, a pyrimidine group, a pyridazine group, or a triazine group, but embodiments of the present disclosure are not limited thereto.

At least one substituent of the substituted $C_2$-$C_{60}$ alkylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_5$-$C_{30}$ carbocyclic group, and the substituted $C_1$-$C_{30}$ heterocyclic group may be:

a halogen atom, a hydroxy group, a thiol group, a nitro group, or a sulfonyl group;

an alkoxy group such as a methoxy group, an ethoxy group, a propoxy group, an iso-propyloxy group, a butoxy group, a phenyloxymethyl group, or a phenyloxyethoxy group;

an alkylcarbonyl group such as a methylcarbonyl group, an ethylcarbonyl group, a propylcarbonyl group, or a butylcarbonyl group;

an ester group such as a methyloxycarbonyl group, an ethyloxycarbonyl group, a propyloxycarbonyl group, or a butyloxycarbonyl group;

an alkyl aryl group such as a methylphenyl group, an ethylphenyl group, a propylphenyl group, or a dimethylfluorenyl group; or a diphenylaminophenyl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

Also, when $A_1$ to $A_3$ are each independently an alkyl group, an alkenyl group, or an alkynyl group, an aryl group or a heteroaryl group may be a substituent. Also, when $A_1$ to $A_3$ are each independently an aryl group, for example, an alkyl group, an alkenyl group, an alkynyl group, an aryl group, or a heteroaryl group may be a substituent. Also, when $A_1$ to $A_3$ are each independently a heteroaryl group, for example, an alkyl group, an alkenyl group, an alkynyl group, an aryl group, or a heteroaryl group may be a substituent.

In an embodiment, at least one of $A_1$ to $A_3$ in the at least one compound represented by Formula (1), which is included in the luminescent host material, may be a group represented by Formula (2-A):

Formula (2-A)

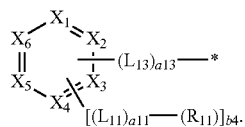

In Formula (2-A), $X_1$ may be N, carbon linked to *-$(L_{11})_{a11}$-$(R_{11})$, or carbon linked to $L_{13}$; $X_2$ may be N, carbon linked to *-$(L_{11})_{a11}$-$(R_{11})$, or carbon linked to $L_{13}$; $X_3$ may be N, carbon linked to *-$(L_{11})_{a11}$-$(R_{11})$, or carbon linked to $L_{13}$; $X_4$ may be N, carbon linked to *-$(L_{11})_{a11}$-$(R_{11})$, or carbon linked to $L_{13}$; $X_5$ may be N, carbon linked to *-$(L_{11})_{a11}$-$(R_{11})$, or carbon linked to $L_{13}$; and $X_6$ may be N, carbon linked to *-$(L_{11})_{a11}$-$(R_{11})$, or carbon linked to $L_{13}$, at least one of $X_1$ to $X_6$ may be N, $L_{11}$ and $L_{13}$ are the same as described in connection with $L_1$, a11 and a13 are the same as described in connection with a1, $R_{11}$ is the same as described in connection with A1, two or more neighboring groups selected from a plurality of groups $R_{11}$ may optionally be linked to form a substituted or unsubstituted $C_5$-$C_{30}$ carbocyclic group or a substituted or unsubstituted $C_2$-$C_{30}$ heterocyclic group, b4 may be an integer from 0 to 4, and

* indicates a binding site to a neighboring atom.

In an embodiment, the group represented by Formula (2-A) may be selected from groups represented by Formulae (2)-1 to (2)-7:

Formula (2)-1

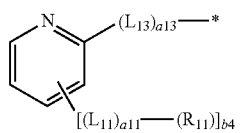

Formula (2)-2

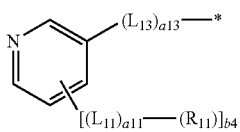

Formula (2)-3

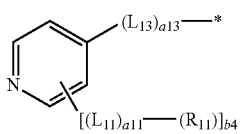

Formula (2)-4

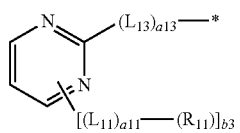

Formula (2)-5

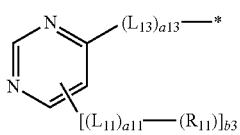

Formula (2)-6

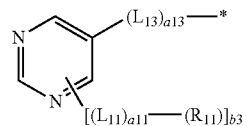

Formula (2)-7

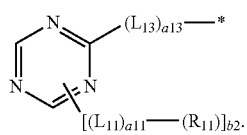

In Formulae (2)-1 to (2)-7, $L_{11}$, $L_{13}$, a11, a13, $R_{11}$, and $(L_{11})_{a11}$-$(R_{11})$ are the same as described herein, b4 may be an integer from 0 to 4, b3 may be an integer from 0 to 3, b2 may be an integer from 0 to 2, and * indicates a binding site to a neighboring atom.

In an embodiment, the group represented by Formula (2-A) may be selected from groups represented by Formulae (2)-A to (2)-F:

Formula (2)-A

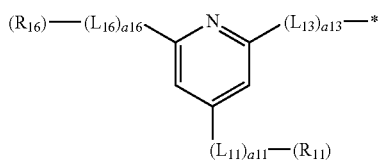

Formula (2)-B

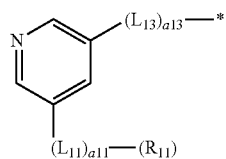

Formula (2)-C

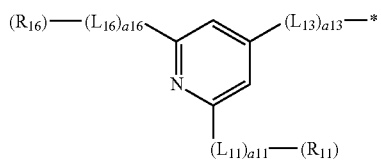

Formula (2)-D

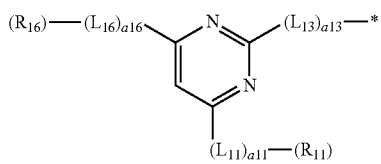

Formula (2)-E

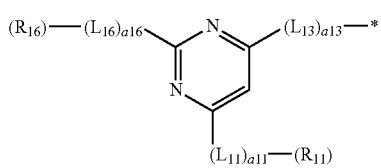

-continued

Formula (2)-F

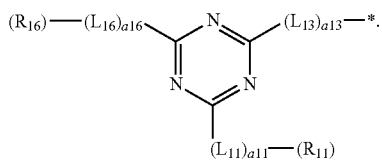

In Formulae (2)-A to (2)-F, $L_{11}$, $L_{13}$, a11, a13, $R_{11}$, and $(L_{11})_{a11}$-$(R_{11})$ are the same as described herein, $L_{16}$, a16, $R_{16}$, and $(L_{16})_{a16}$-$(R_{16})$ are the same as described in connection with $L_{11}$, a11, $R_{11}$, and $(L_{11})_{a11}$-$(R_{11})$, and * indicates a binding site to a neighboring atom.

In one or more embodiments, the luminescent host material may include at least one component represented by Formula (2):

Formula (2)

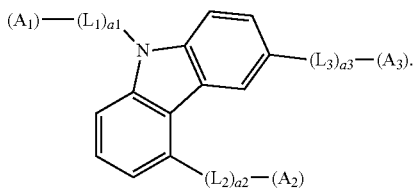

$L_1$ to $L_3$, a1 to a3, and $A_1$ to $A_3$ in Formula (2) are the same as described herein.

For example, at least one of $A_1$ to $A_3$ in Formula (2) may be the group represented by Formula (2-A).

For example, at least of $A_1$ and $A_2$ in Formula (2) may be the group represented by Formula (2-A), but embodiments of the present disclosure are not limited thereto.

In one or more embodiments, the luminescent host material may include at least one compound having a biscarbazole backbone.

For example, the luminescent host material may include at least one compound represented by Formula (3):

Formula (3)

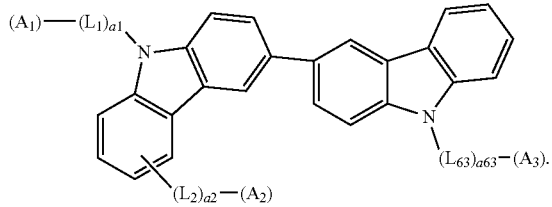

Formula (3) corresponds to a compound in which one of groups $L_3$ in the number of a3 in Formula (1) is "a carbazole group".

In Formula (3), $L_1$, $L_2$, a2, a3, $A_1$, and $A_2$ are the same as described herein, and $L_{63}$, a63, and $A_3$ are the same as described in connection with $L_3$, a3, and $A_3$.

For example, in Formula (3),
$L_1$, $L_2$, and $L_{63}$ may each independently be selected from a single bond, a substituted or unsubstituted $C_2$-$C_{60}$ alkylene group, a substituted or unsubstituted $C_3$-$C_{10}$ cycloalkylene group, a substituted or unsubstituted π electron-depleted nitrogen-free $C_1$-$C_{10}$ heterocycloalkylene group, a substituted or unsubstituted $C_3$-$C_{10}$ cycloalkenylene group, a substituted or unsubstituted π electron-depleted nitrogen-free $C_1$-$C_{10}$ heterocycloalkenylene group, a substituted or unsubstituted $C_6$-$C_{60}$ arylene group, a substituted or unsubstituted π electron-depleted nitrogen-free $C_1$-$C_{60}$ heteroarylene group, a substituted or unsubstituted divalent non-aromatic condensed polycyclic group, and a substituted or unsubstituted divalent π electron-depleted nitrogen-free non-aromatic condensed heteropolycyclic group, a1, a2, and a63 may each independently be an integer from 1 to 10, $A_1$, $A_2$, and $A_{63}$ may each independently be selected from hydrogen, deuterium, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted π electron-depleted nitrogen-free $C_1$-$C_{10}$ heterocycloalkyl group, a substituted or unsubstituted $C_3$-$C_{10}$ cycloalkenyl group, a substituted or unsubstituted π electron-depleted nitrogen-free $C_1$-$C_{10}$ heterocycloalkenyl group, a substituted or unsubstituted $C_6$-$C_{60}$ aryl group, a substituted or unsubstituted π electron-depleted nitrogen-free $C_1$-$C_{60}$ heteroaryl group, a substituted or unsubstituted monovalent non-aromatic condensed polycyclic group, and a substituted or unsubstituted π electron-depleted nitrogen-free monovalent non-aromatic condensed heteropolycyclic group, at least one of the substituted $C_2$-$C_{60}$ alkylene group, the substituted $C_3$-$C_{10}$ cycloalkylene group, the substituted π electron-depleted nitrogen-free $C_1$-$C_{10}$ heterocycloalkylene group, the substituted $C_3$-$C_{10}$ cycloalkenylene group, the substituted π electron-depleted nitrogen-free $C_1$-$C_{10}$ heterocycloalkenylene group, the substituted $C_6$-$C_{60}$ arylene group, the substituted π electron-depleted nitrogen-free $C_1$-$C_{60}$ heteroarylene group, the substituted divalent non-aromatic condensed polycyclic group, the substituted divalent π electron-depleted nitrogen-free non-aromatic condensed heteropolycyclic group, the substituted $C_1$-$C_{60}$ alkyl group, the substituted $C_1$-$C_{60}$ alkoxy group, the substituted $C_3$-$C_{10}$ cycloalkyl group, the substituted π electron-depleted nitrogen-free $C_1$-$C_{10}$ heterocycloalkyl group, the substituted $C_3$-$C_{10}$ cycloalkenyl group, the substituted π electron-depleted nitrogen-free $C_1$-$C_{10}$ heterocycloalkenyl group, the substituted $C_6$-$C_{60}$ aryl group, the substituted π electron-depleted nitrogen-free $C_1$-$C_{60}$ heteroaryl group, the substituted monovalent non-aromatic condensed polycyclic group, and the substituted π electron-depleted nitrogen-free monovalent non-aromatic condensed heteropolycyclic group may be selected from:

deuterium and a $C_1$-$C_{60}$ alkyl group;

a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, and a π electron-depleted nitrogen-free monovalent non-aromatic condensed heteropolycyclic group; and a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, and a π electron-depleted nitrogen-free monovalent non-aromatic condensed heteropolycyclic group, each substituted with at least one selected from deuterium, a $C_1$-$C_{60}$ alkyl group, a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, and a π electron-depleted nitrogen-free monovalent non-aromatic condensed heteropolycyclic group.

In an embodiment, $L_1$, $L_2$, and $L_{63}$ in Formula (3) may each independently be selected from:
a single bond; and
a phenylene group, a fluorenylene group, a spiro-bifluorenylene group, a carbazolylene group, a dibenzofuranylene group, and a dibenzothiophenylene group, each substituted or unsubstituted with at least one selected from deuterium, —$CD_3$, —$CD_2H$, —$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group, a1, a2, and a63 may each independently be 1, 2, or 3, $A_1$, $A_2$, and $A_{63}$ may each independently be selected from:
hydrogen, deuterium, —$CD_3$, —$CD_2H$, —$CDH_2$, a $C_1$-$C_{20}$ alkyl group, and a $C_1$-$C_{20}$ alkoxy group; and
a phenyl group, a fluorenyl group, a spiro-bifluorenyl group, a carbazolyl group, a dibenzofuranyl group, and a dibenzothiophenyl group, each substituted or unsubstituted with at least one selected from deuterium, —$CD_3$, —$CD_2H$, —$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

For example, $L_1$ to $L_3$, $L_{63}$, $L_{11}$, and $L_{13}$ in Formulae (1) to (3) and (2-A) may each independently be selected from a single bond and groups represented by Formulae 6-1 to 6-27, but embodiments of the present disclosure are not limited thereto:

Formula 6-1

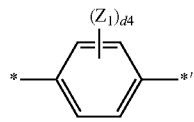

Formula 6-2

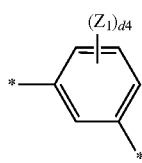

Formula 6-3

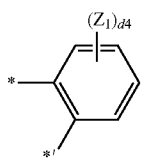

Formula 6-4

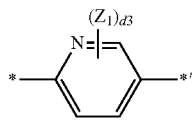

Formula 6-5

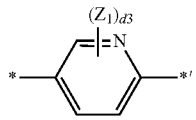

Formula 6-6

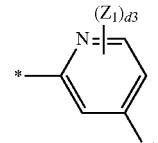

Formula 6-7

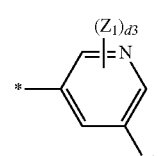

Formula 6-8

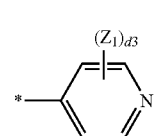

Formula 6-9

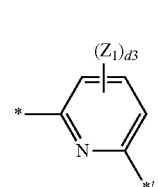

Formula 6-10

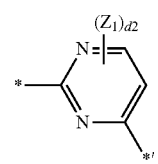

Formula 6-11

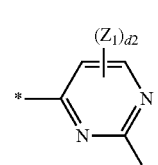

Formula 6-12

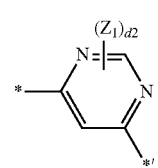

Formula 6-13
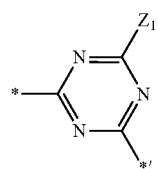
Formula 6-14
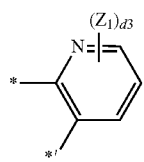
Formula 6-15
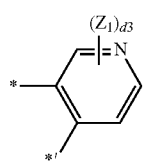
Formula 6-16
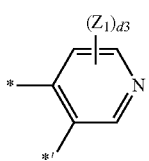
Formula 6-17
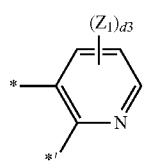
Formula 6-18
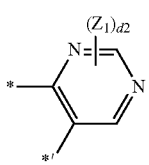
Formula 6-19
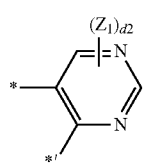
Formula 6-20
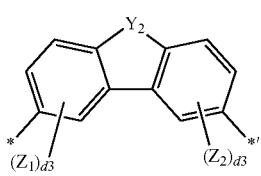
Formula 6-21
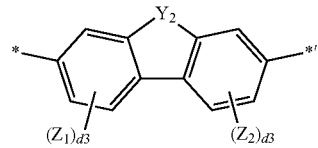
Formula 6-22
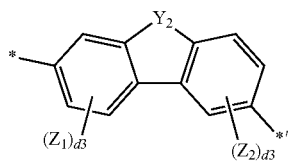
Formula 6-23
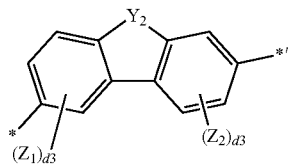
Formula 6-24
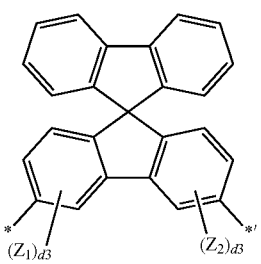
Formula 6-25
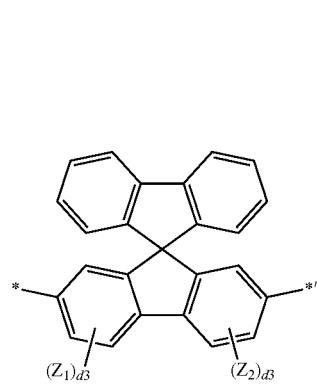
Formula 6-26
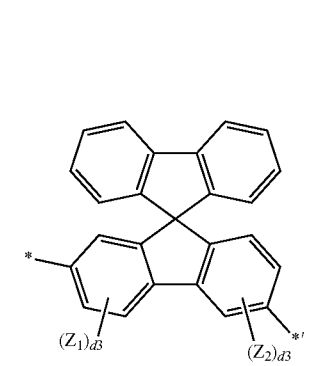

Formula 6-27

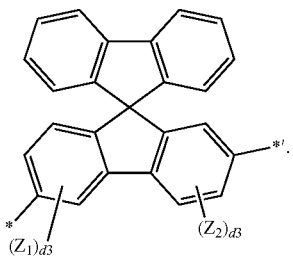

In Formulae 6-1 to 6-27, $Y_2$ may be O, S, $C(Z_3)(Z_4)$, or $N(Z_5)$, $Z_1$ to $Z_5$ may each independently be hydrogen, deuterium, —$CD_3$, —$CD_2H$, —$CDH_2$, a $C_1$-$C_{20}$ alkyl group, a $C_1$-$C_{20}$ alkoxy group, a phenyl group, a biphenyl group, a trimethylsilyl group, or a triphenylsilyl group, d2 may be 1 or 2, d3 may be 1, 2, or 3, d4 may be 1, 2, 3, or 4, and

* and *' each indicate a binding site to a neighboring atom.

In one or more embodiments, $L_1$ to $L_3$, $L_{63}$, $L_{11}$, and $L_{13}$ in Formulae (1) to (3) and (2-A) may each independently be selected from a single bond and groups represented by Formulae 6(1) to 6(10), but embodiments of the present disclosure are not limited thereto:

Formula 6(1)

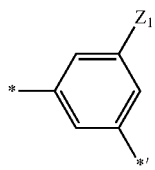

Formula 6(2)

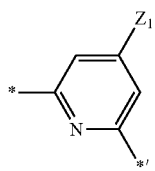

Formula 6(3)

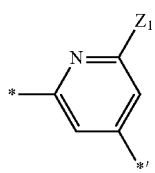

Formula 6(4)

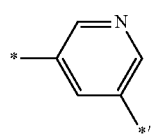

Formula 6(5)

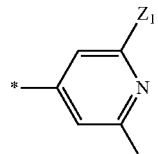

Formula 6(6)

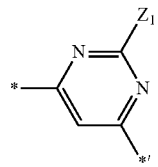

Formula 6(7)

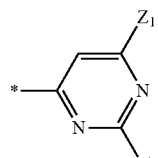

Formula 6(8)

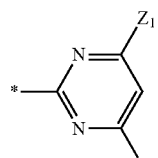

Formula 6(9)

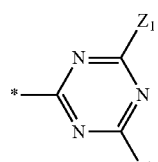

Formula 6(10)

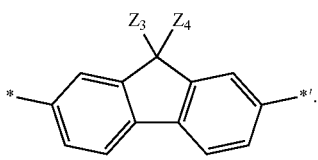

In Formulae 6(1) to 6(10), $Z_1$, $Z_3$, and $Z_5$ may each independently be hydrogen, deuterium, —$CD_3$, —$CD_2H$, —$CDH_2$, a $C_1$-$C_{20}$ alkyl group, a $C_1$-$C_{20}$ alkoxy group, a phenyl group, a biphenyl group, a trimethylsilyl group, or a triphenylsilyl group, and * and *' each indicate a binding site to a neighboring atom.

a1, a2, a3, a63, a11, and a13 respectively indicate the number of groups $L_1$, the number of groups $L_2$, the number of groups $L_3$, the number of groups $L_{63}$, the number of groups $L_{11}$, and the number of groups $L_{13}$, and may each independently be an integer from 1 to 10 or an integer from 1 to 5, but embodiments of the present disclosure are not limited thereto. When a1 is two or more, two or more groups $L_1$ may be identical to or different from each other, and the same applies to a2 and $L_2$, a3 and $L_3$, a63 and $L_{63}$, a11 and $L_{11}$, and a13 and $L_{13}$.

In an embodiment, $A_1$ to $A_3$, $R_5$, and $R_{11}$ in Formulae (1) to (3), (2-A), (2)-1 to (2)-7, (2)-A to (2)-F, and (3)-1 to (3)-11 may each independently be selected from hydrogen, deuterium, a $C_1$-$C_{10}$ alkyl group, groups represented by Formulae 7-1 to 7-57, and groups represented by Formulae 8-1 to 8-7:
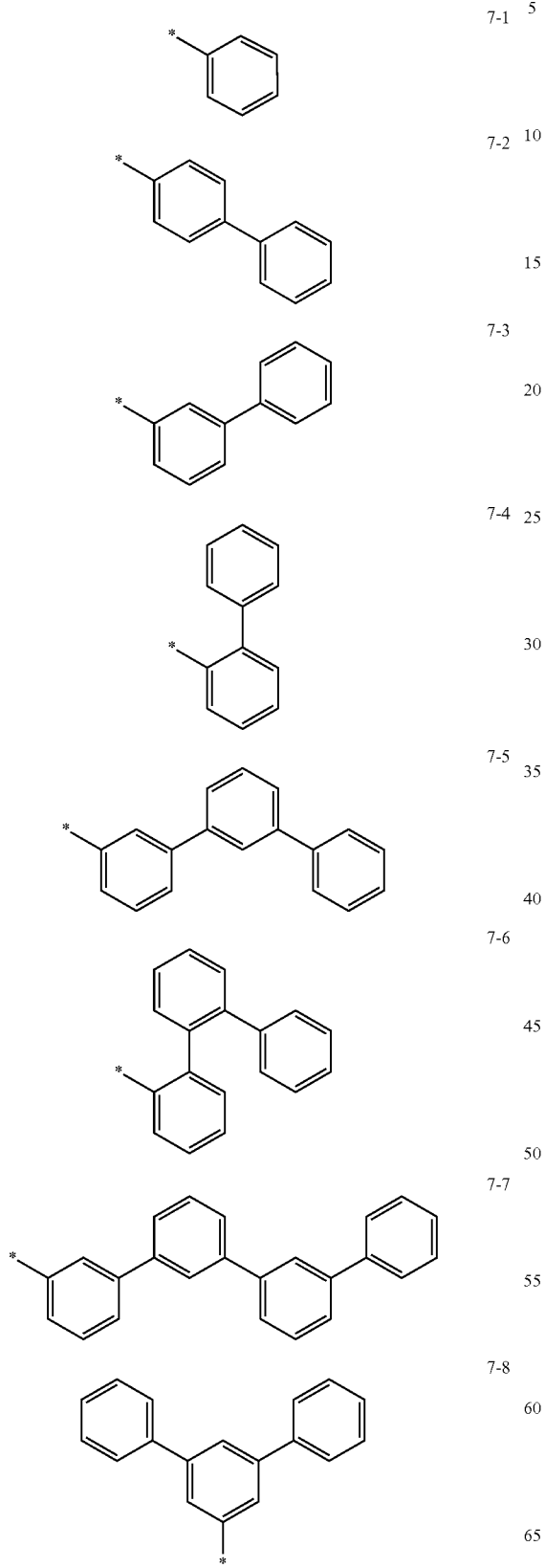
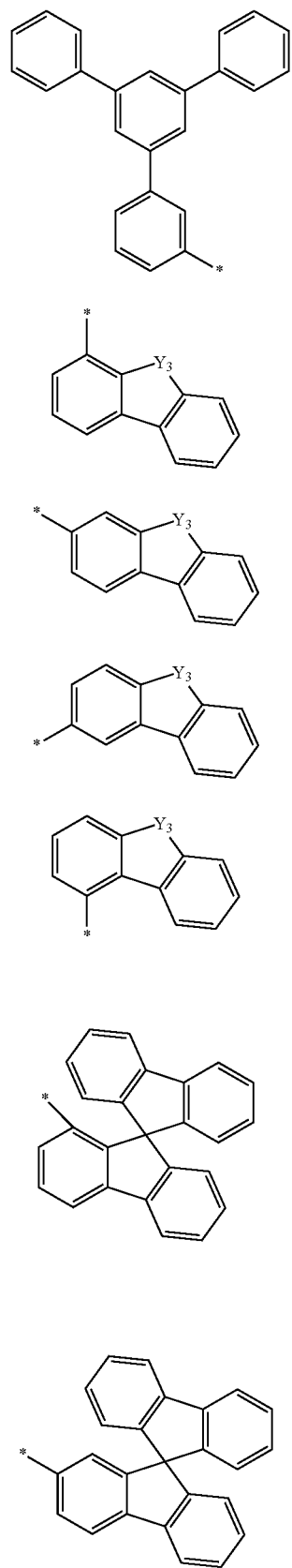

-continued
7-16
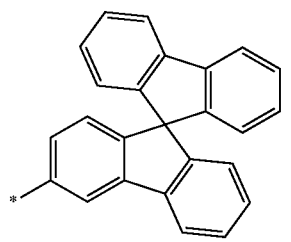
7-17
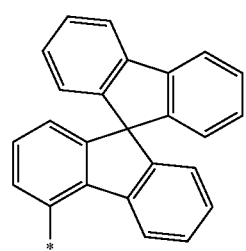
7-18
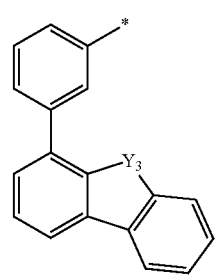
7-19
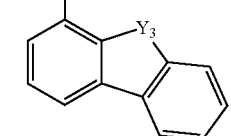
7-20
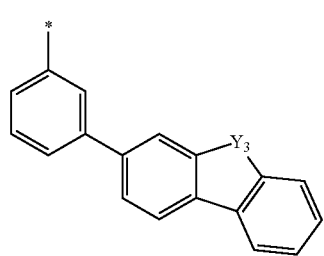
7-21
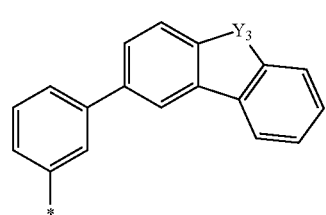
-continued
7-22
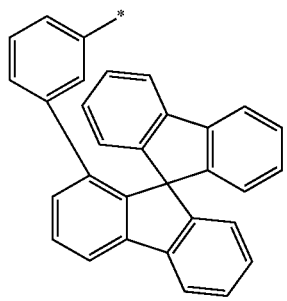
7-23
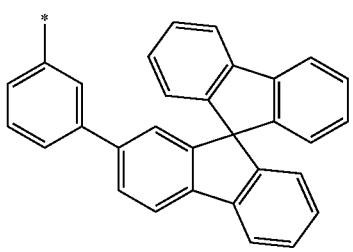
7-24
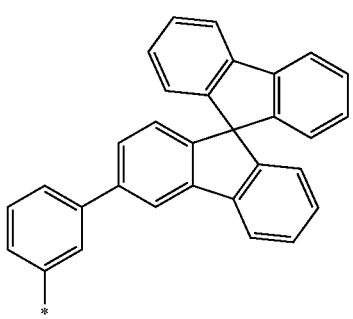
7-25
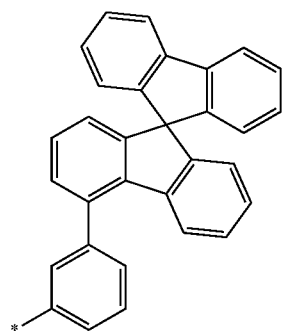
7-26
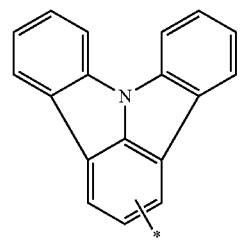

7-27 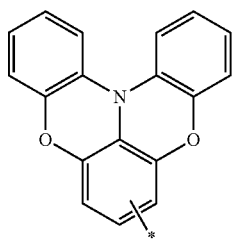
7-28 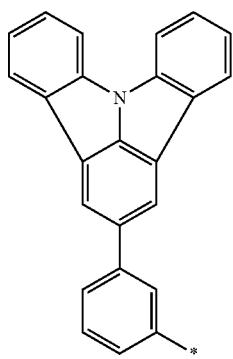
7-29 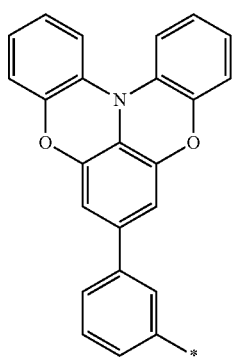
7-30 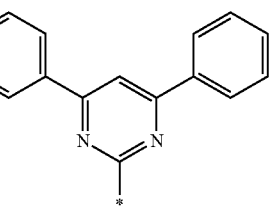
7-31 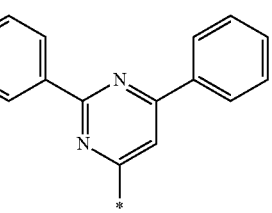
7-32 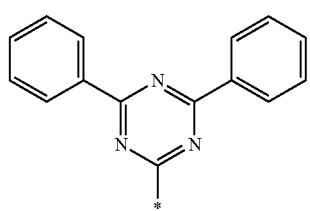
7-33 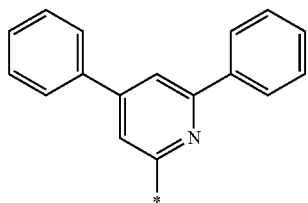
7-34 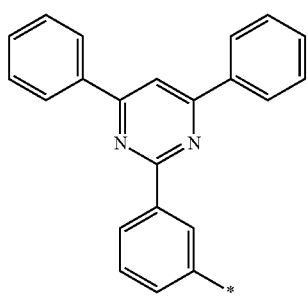
7-35 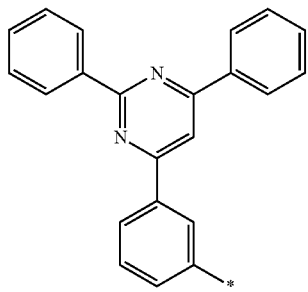
7-36 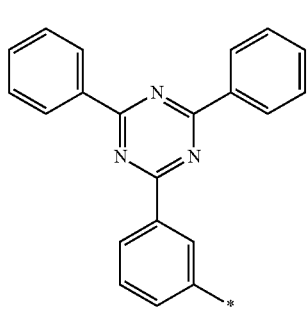
7-37 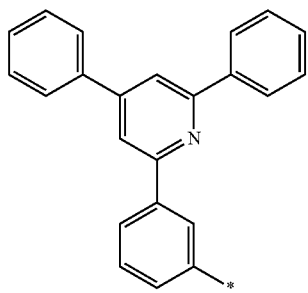

7-38 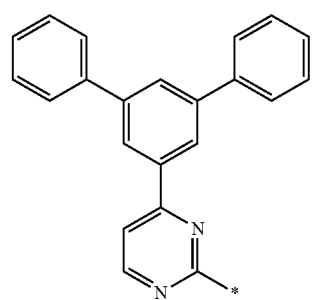
7-39 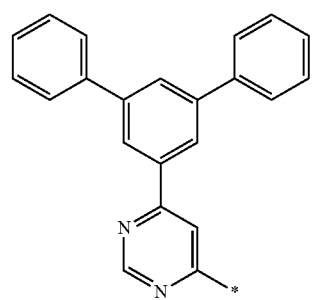
7-40 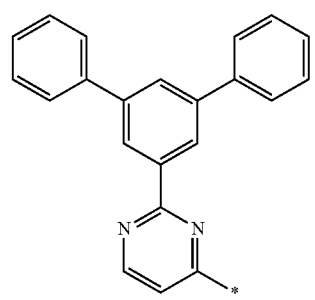
7-41 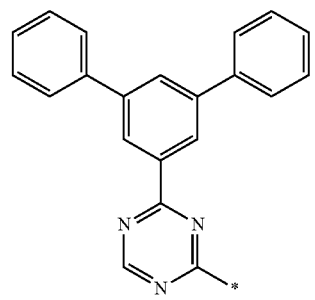
7-42 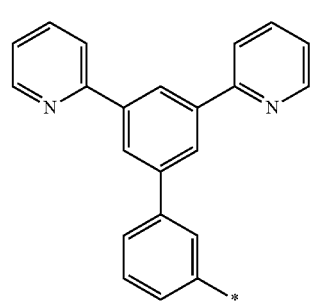
7-43 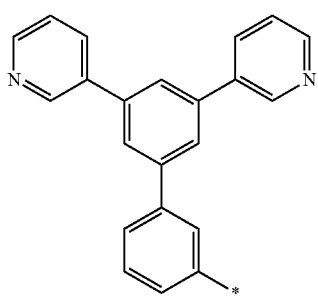
7-44 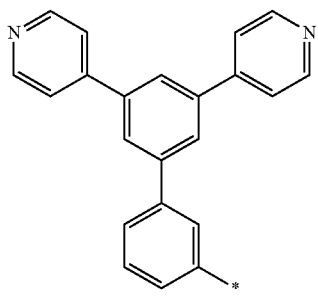
7-45 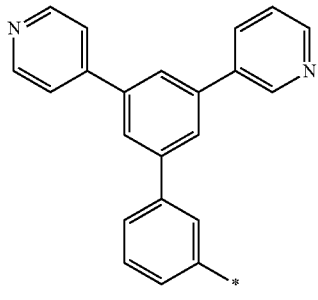
7-46 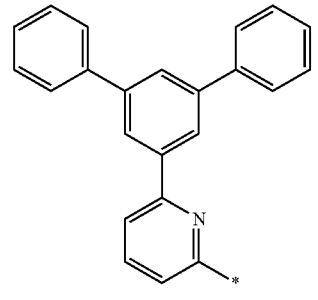
7-47 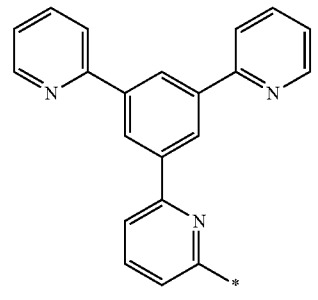

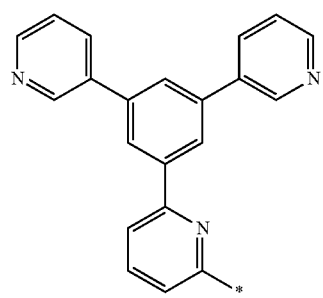
7-48
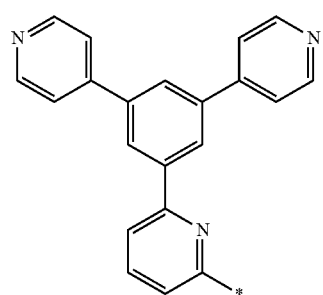
7-49
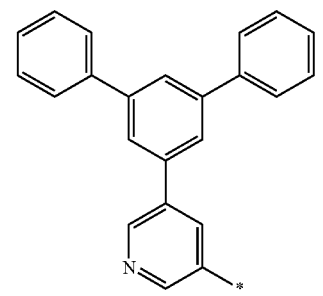
7-50
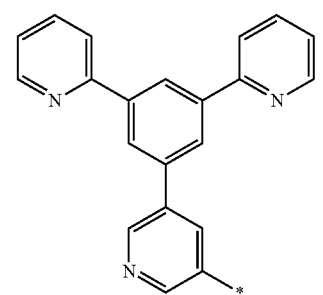
7-51
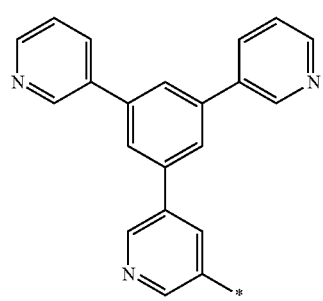
7-52
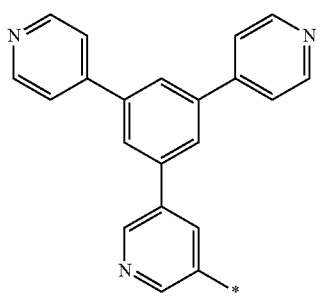
7-53
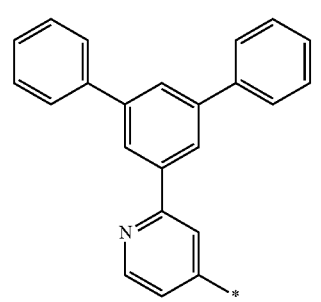
7-54
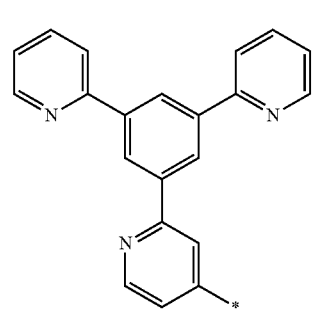
7-55
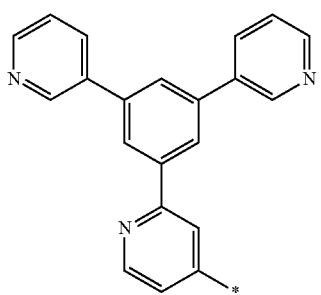
7-56
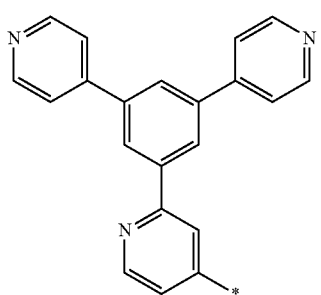
7-57

-continued
8-1
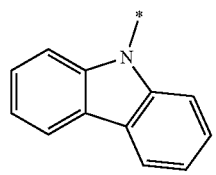
8-2
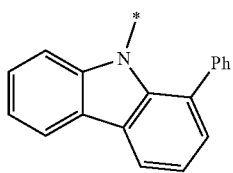
8-3
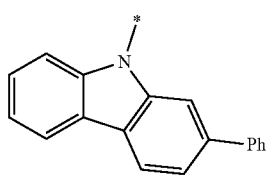
8-4
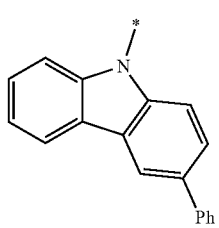
8-5
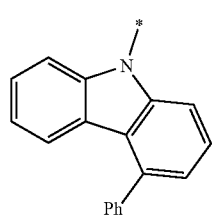
8-6
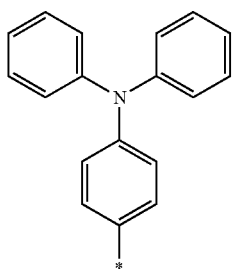
8-7
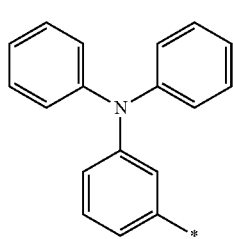
In Formulae 8-1 to 8-7, "Ph" indicates a phenyl group, and "*" indicates a binding site to a neighboring atom.
Specific examples of the compound represented by Formula (1) will be described below. However, the compound according to one or more embodiments is not limited to the structures provided below:
2-1
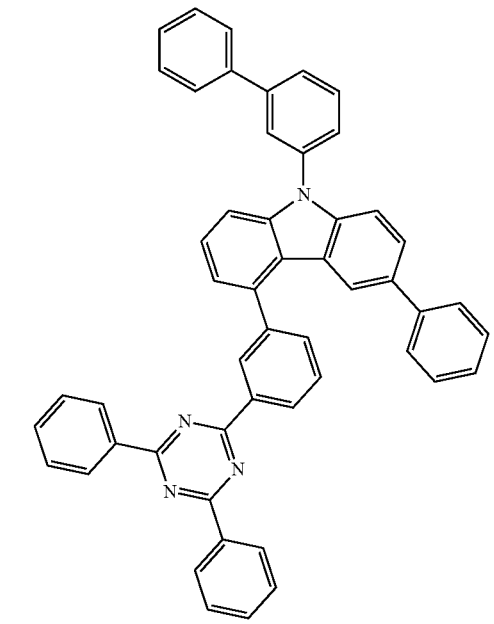
2-2
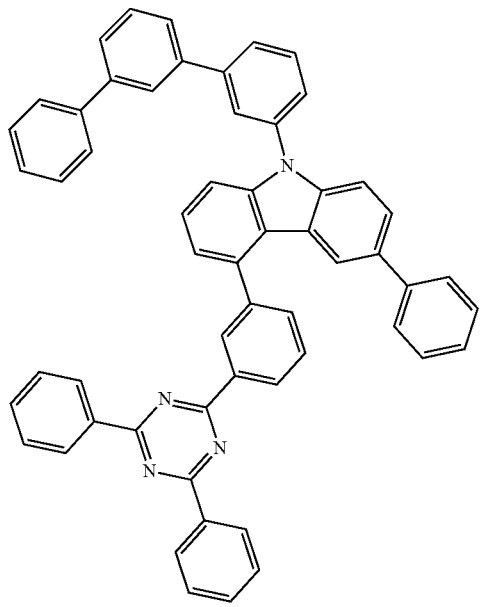

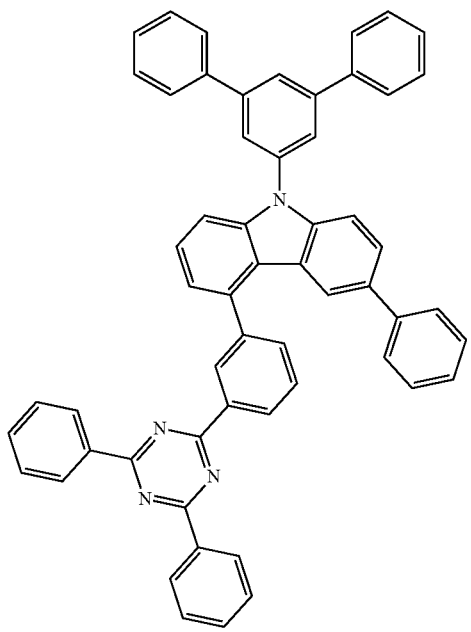
2-3
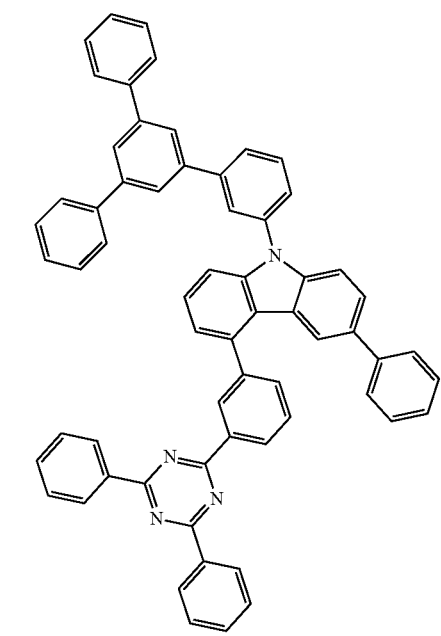
2-4
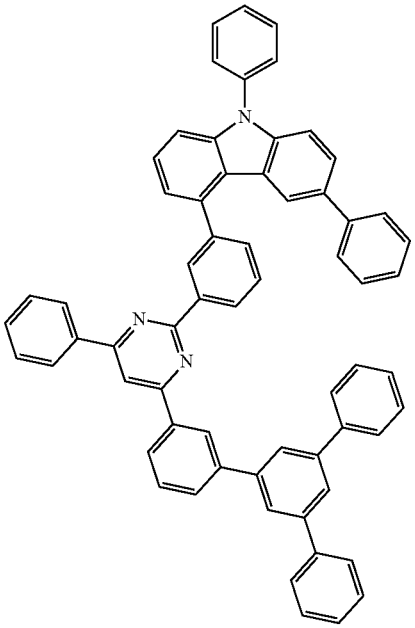
2-5
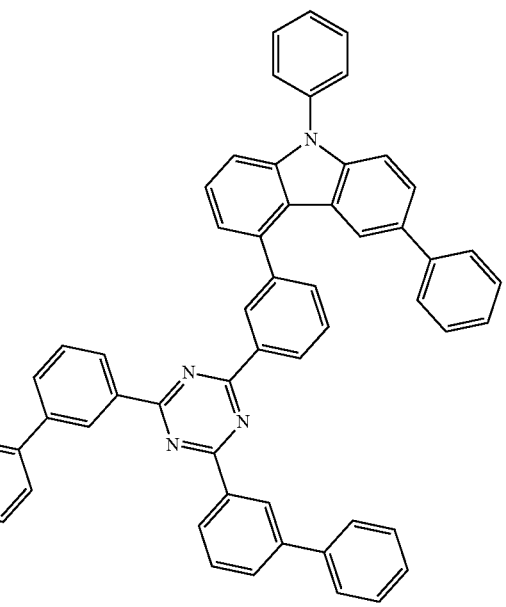
2-6

2-7
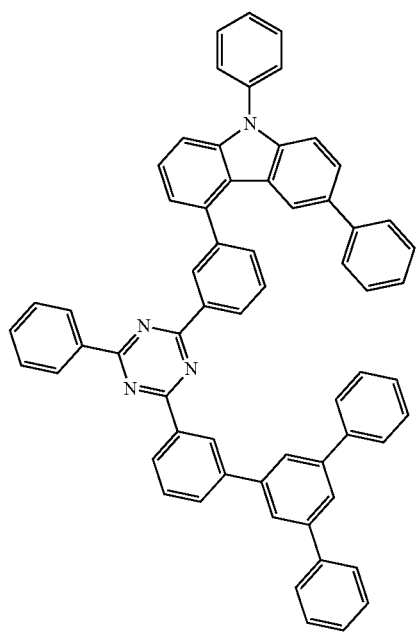
2-8
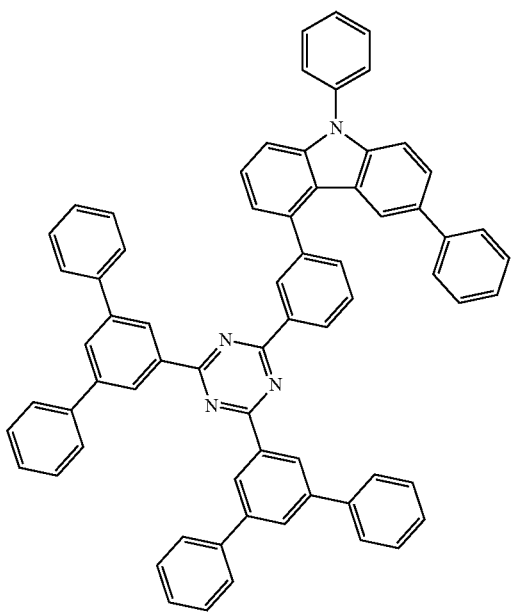
2-9
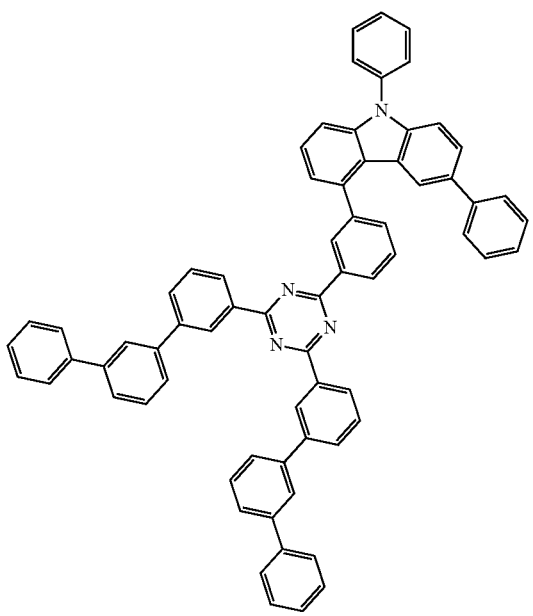
2-10

2-11
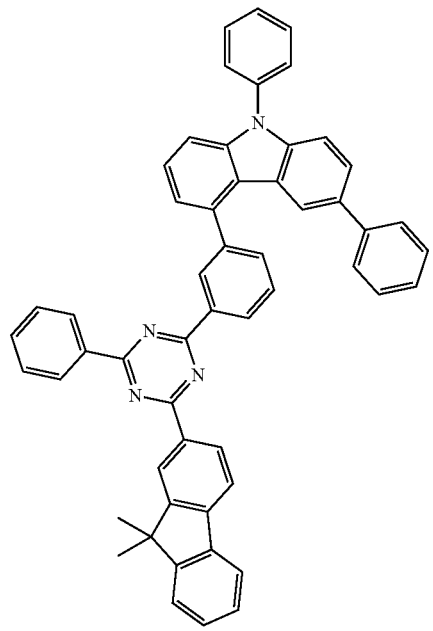
2-12
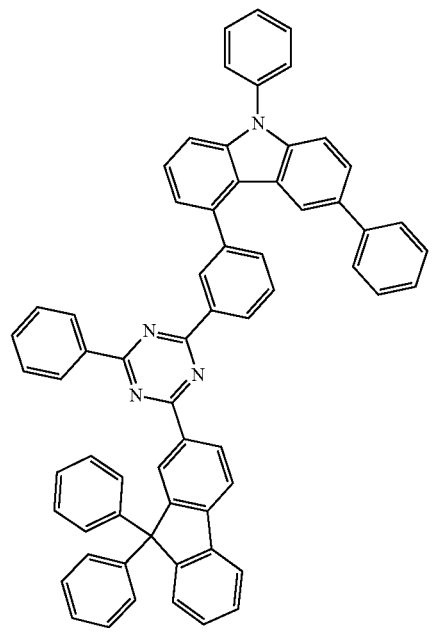
2-13
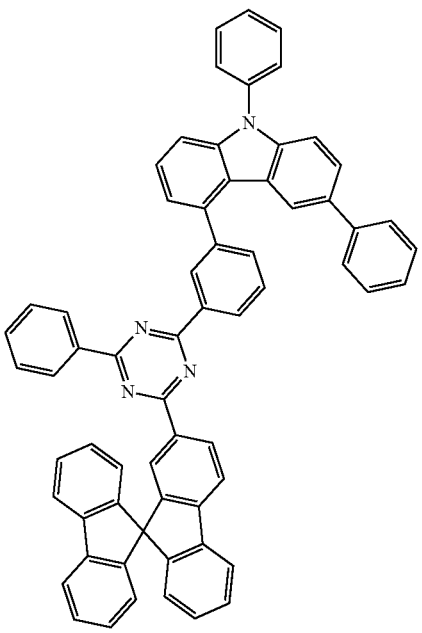
2-14
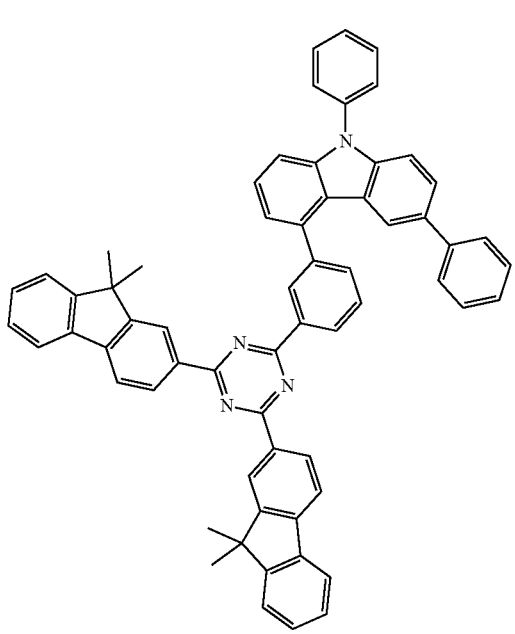

2-15
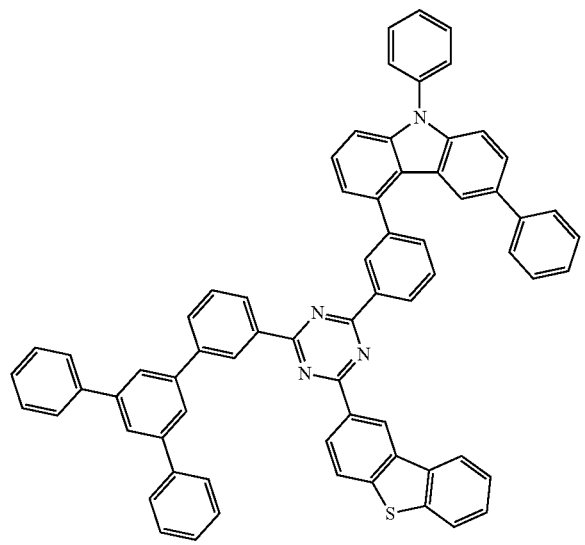
2-17
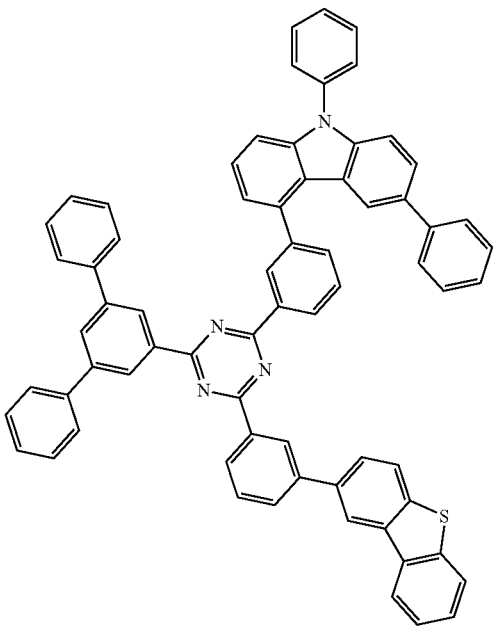
2-16
2-18
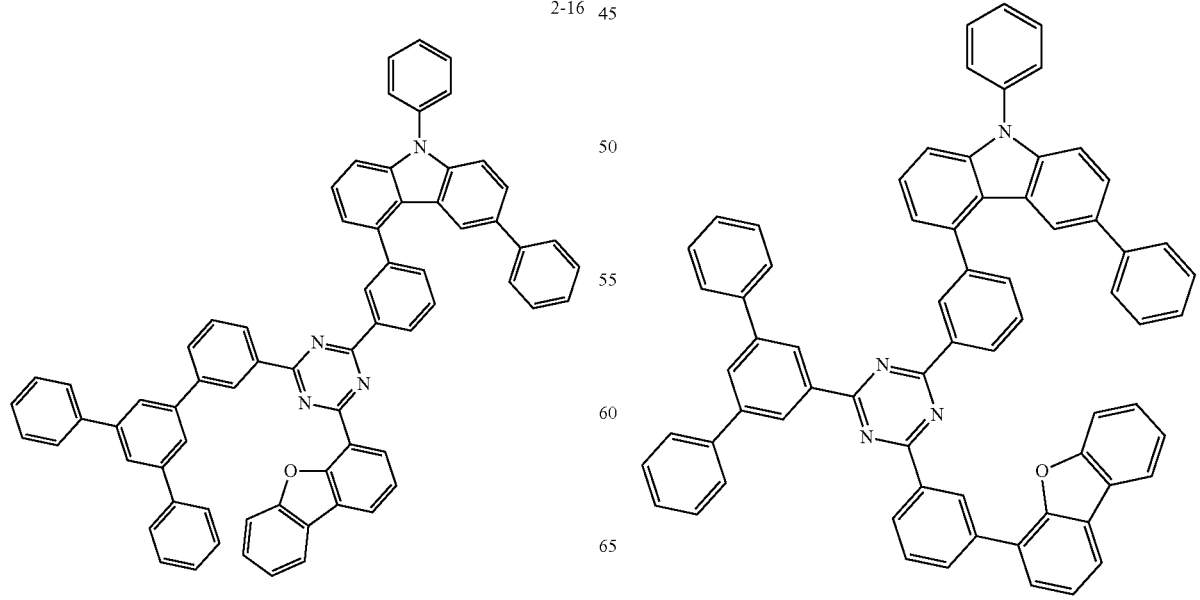

2-19
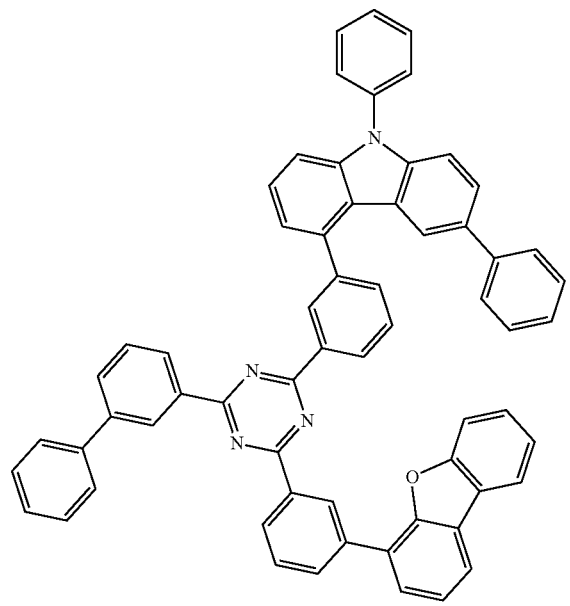
2-21
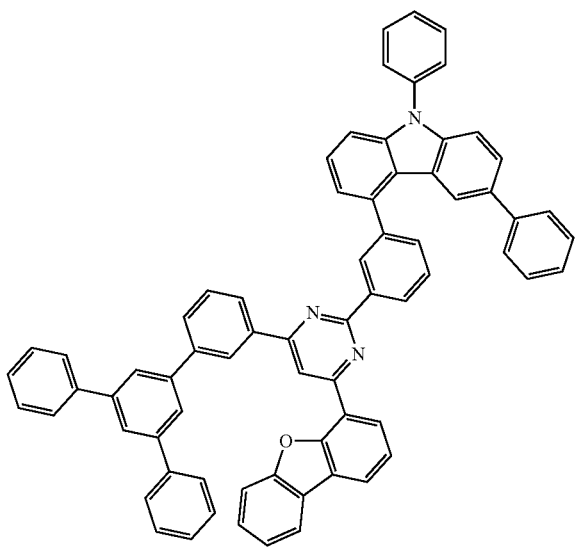
2-20
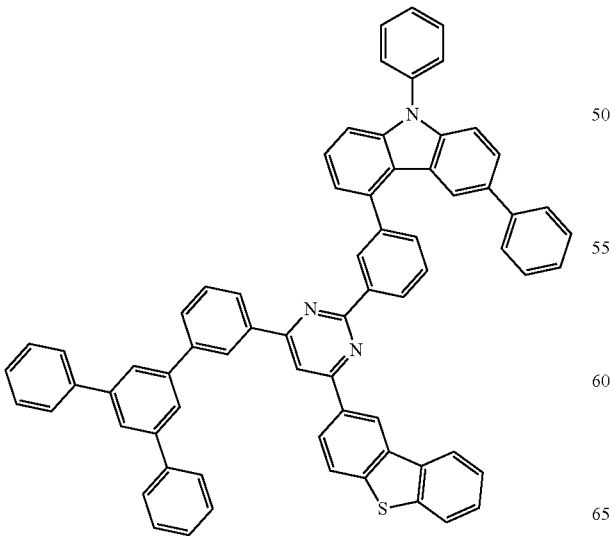
2-22
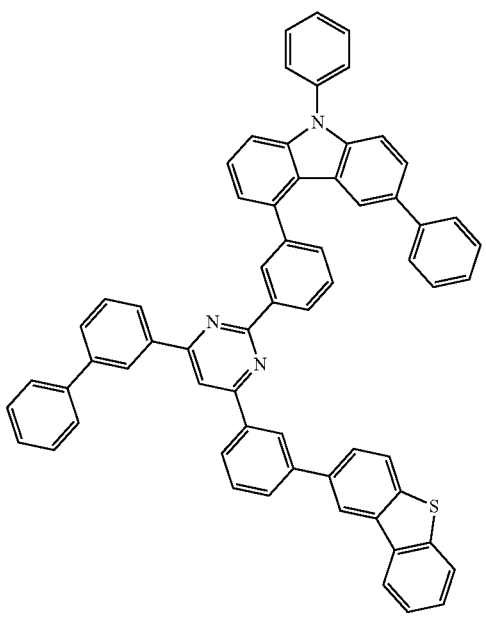

2-23
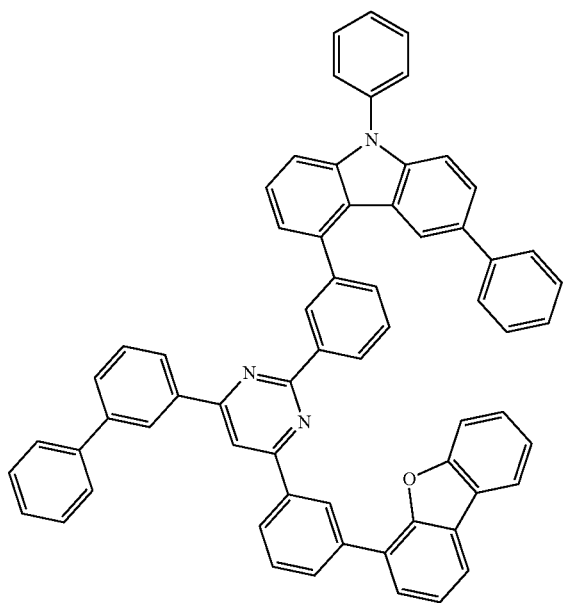
2-25
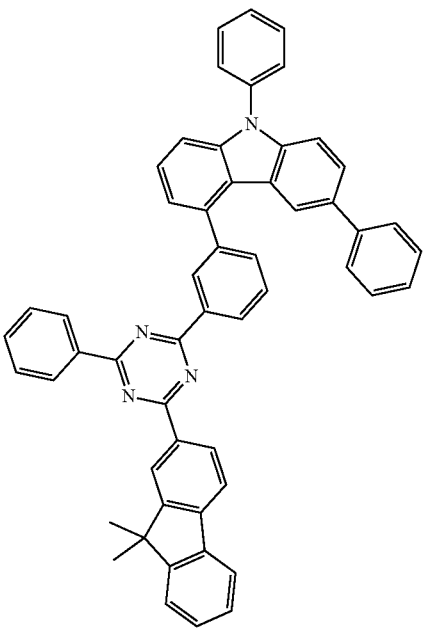
2-24
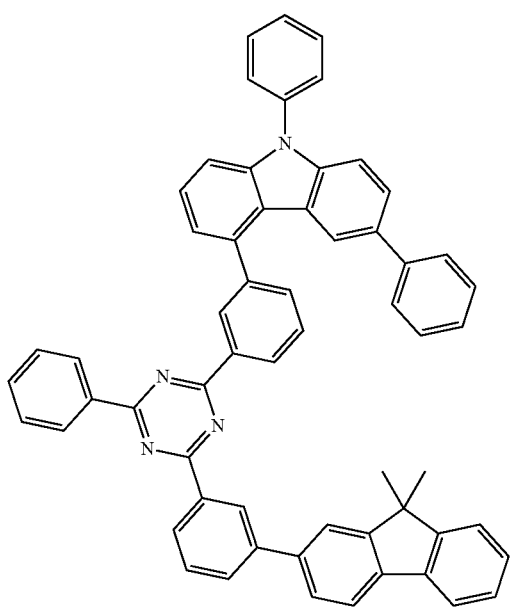
2-26
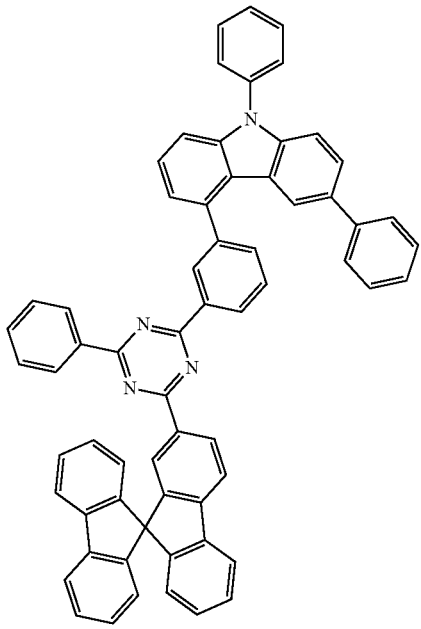

2-27
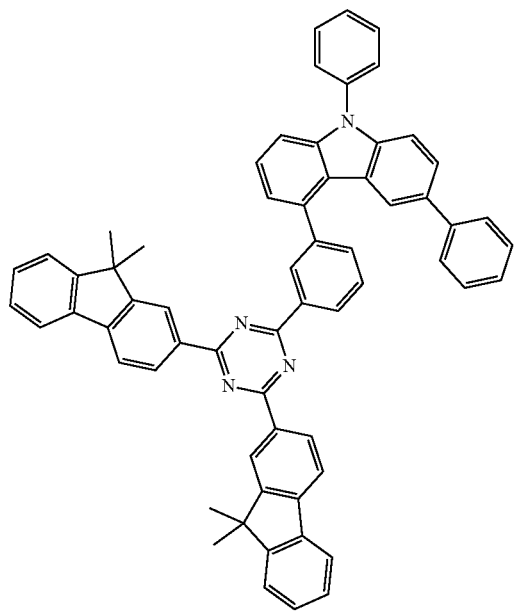
2-28
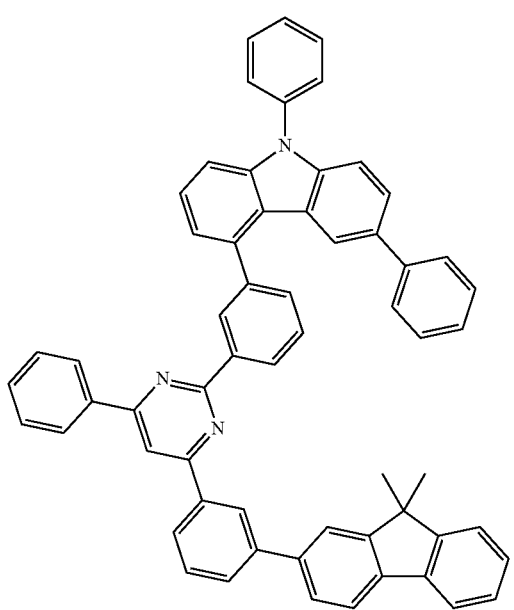
2-29
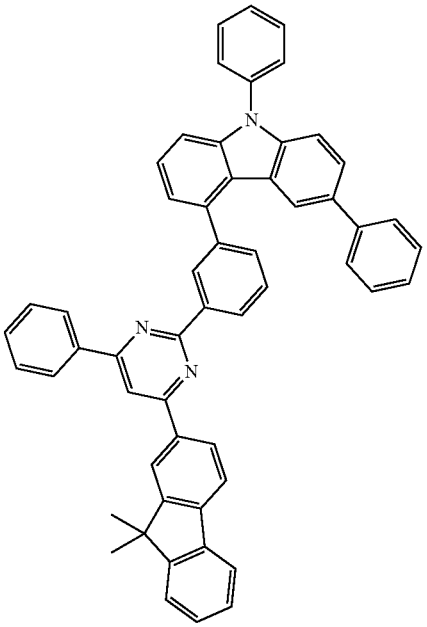
2-30

-continued
2-31
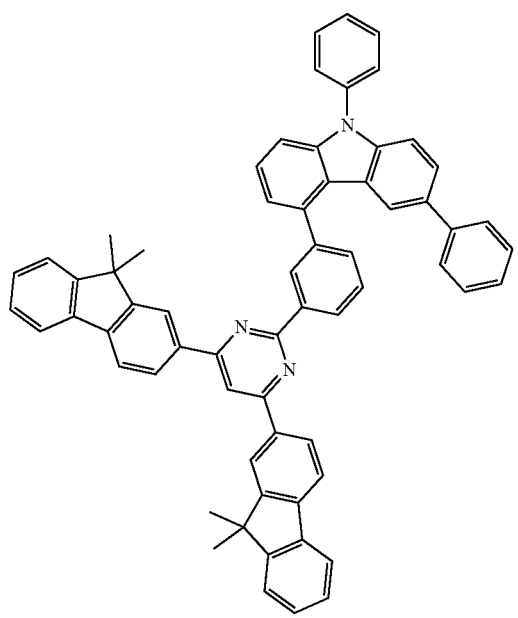
2-33
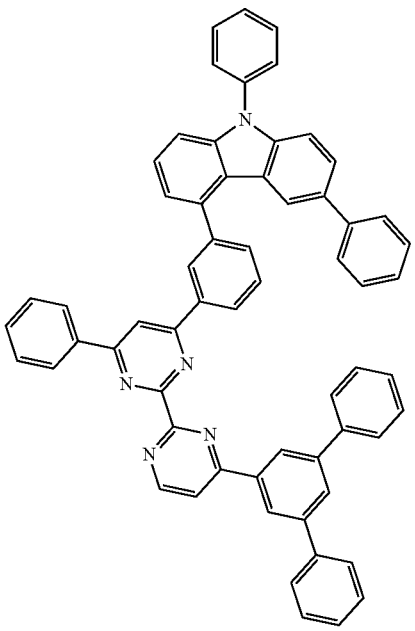
2-32
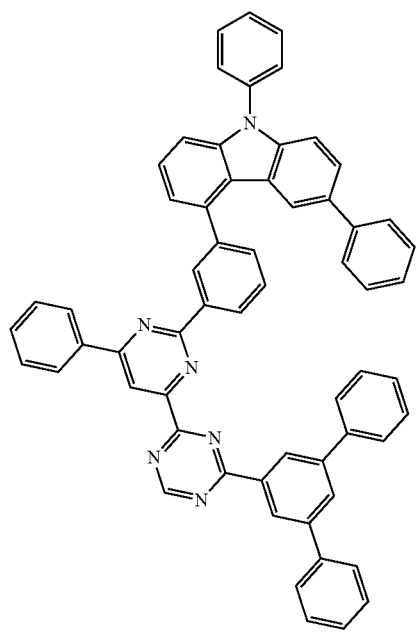
2-34
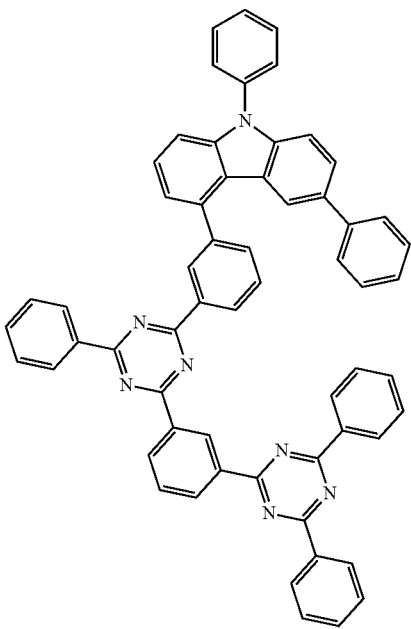

2-35
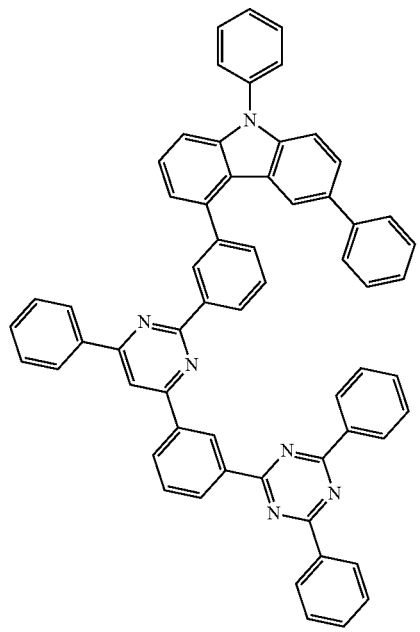
2-36
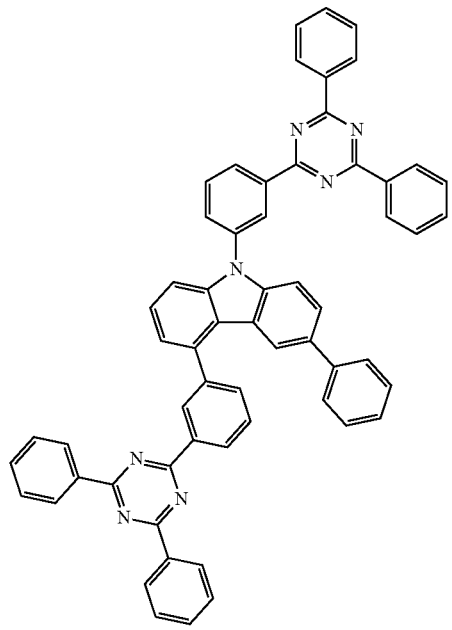
2-37
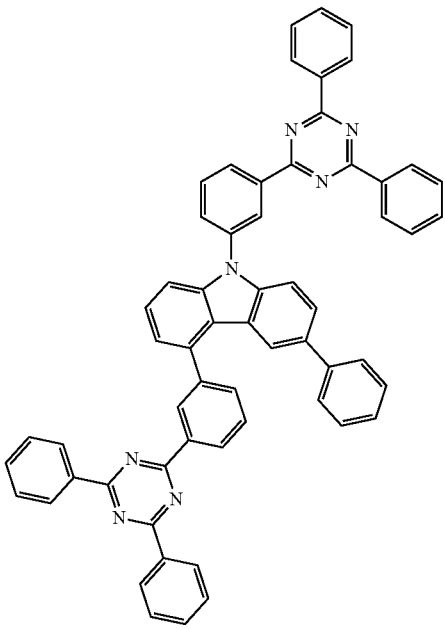
2-38
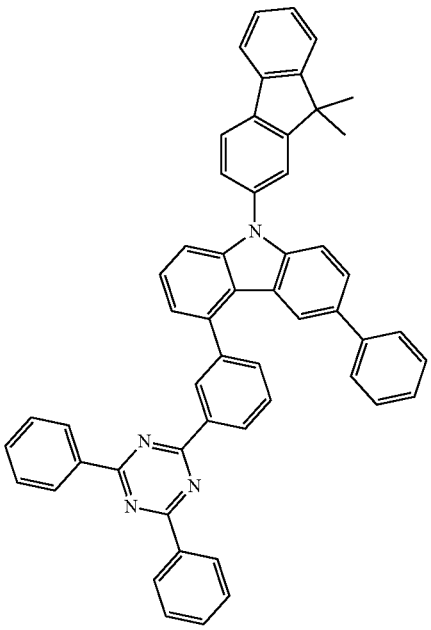

2-39
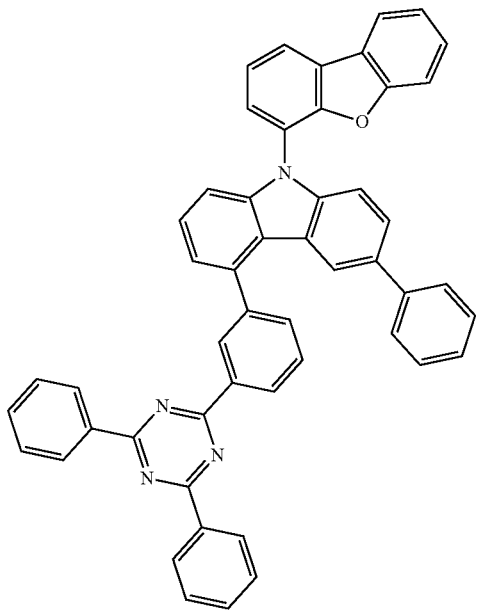
2-40
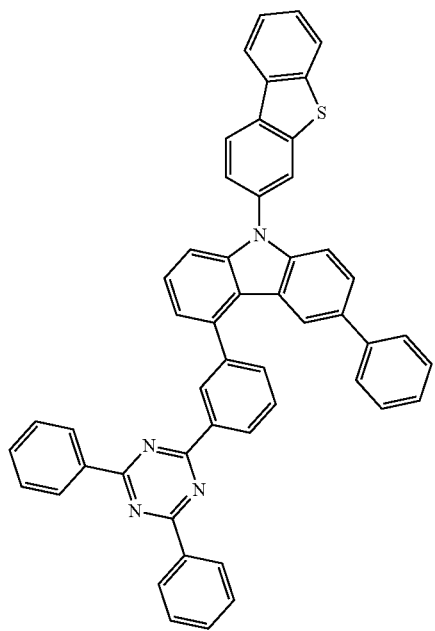
2-41
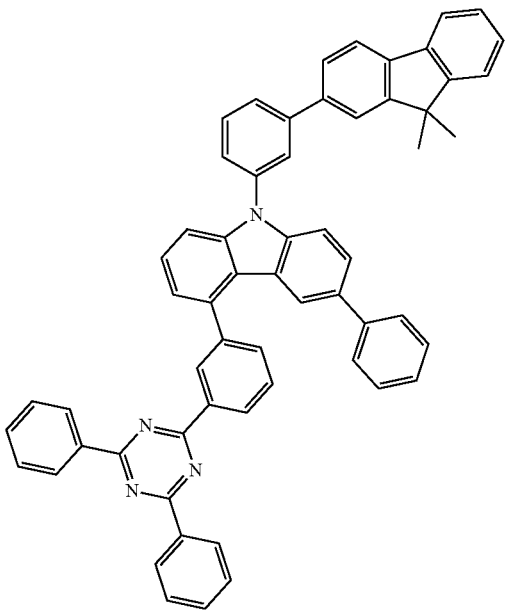
2-42
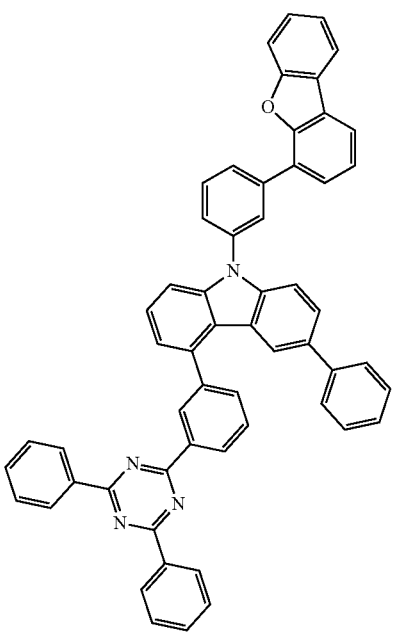

2-43
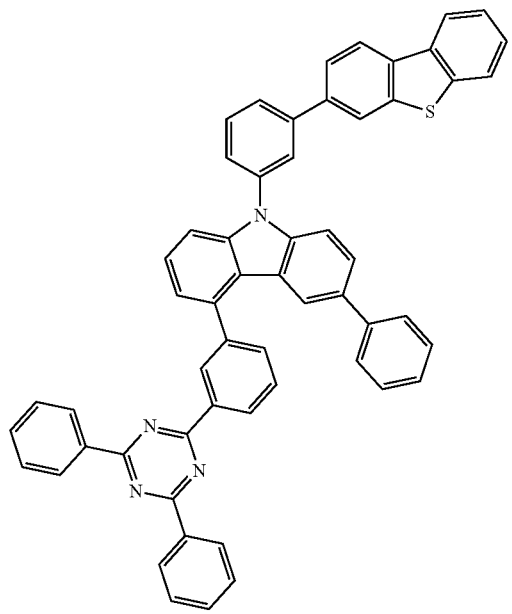
2-45
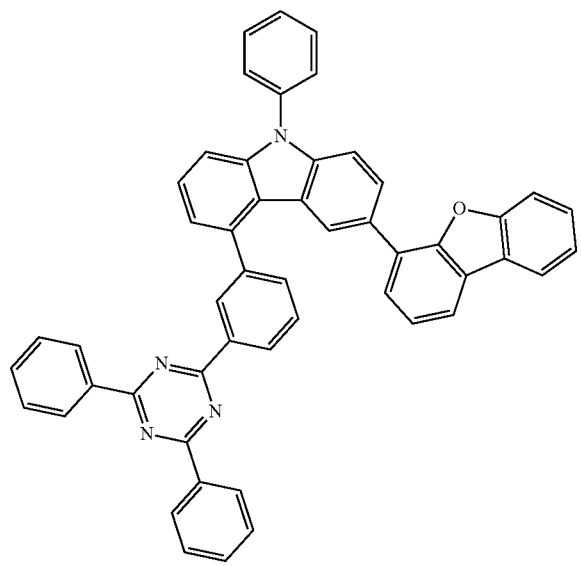
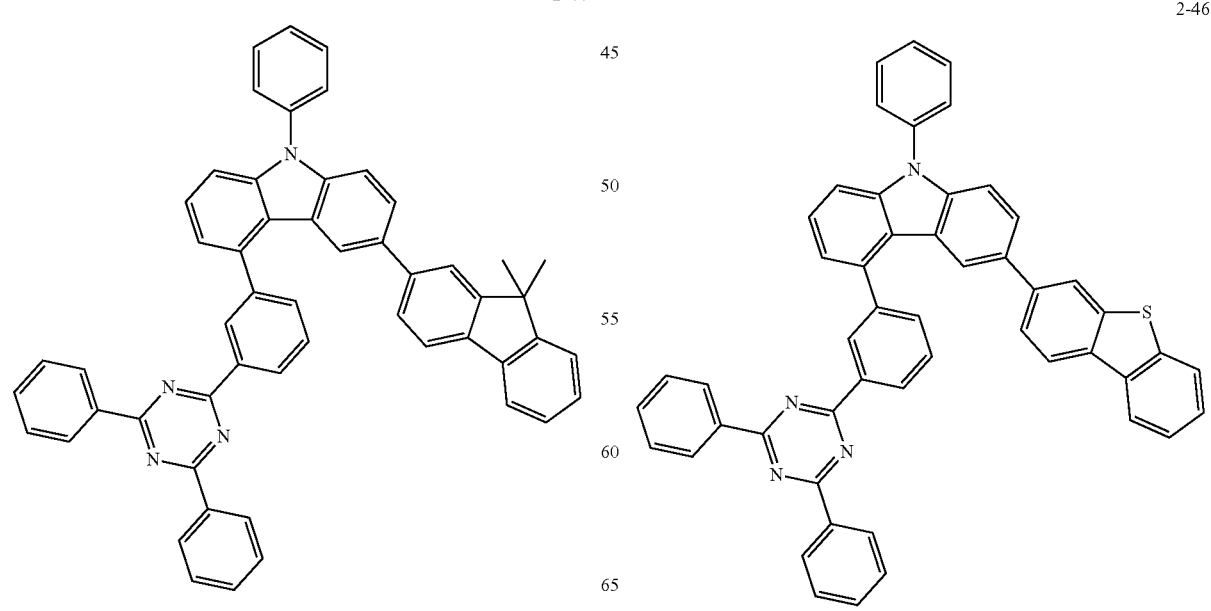
2-44
2-46

2-47
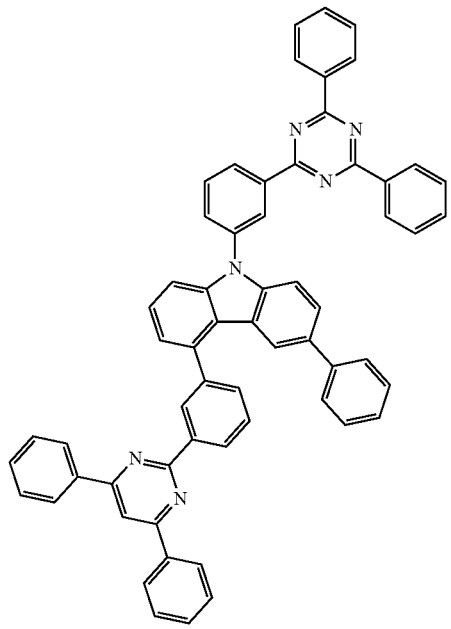
2-48
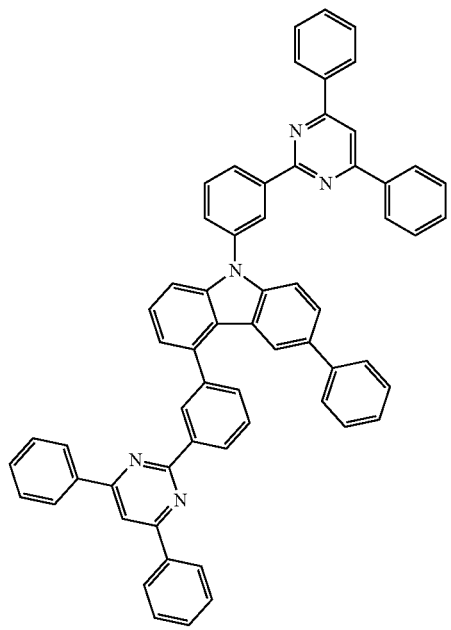
2-49
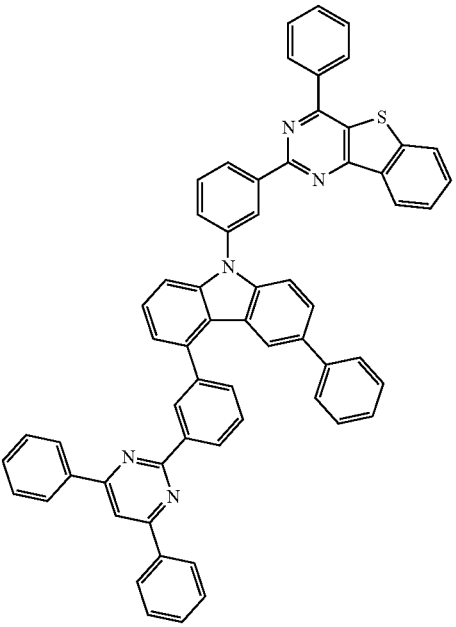
2-50
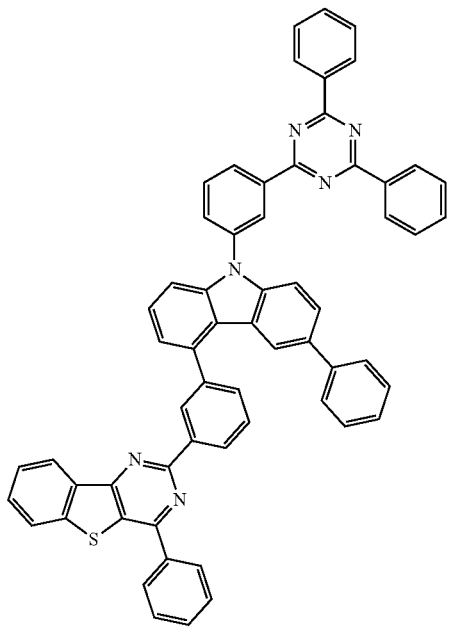

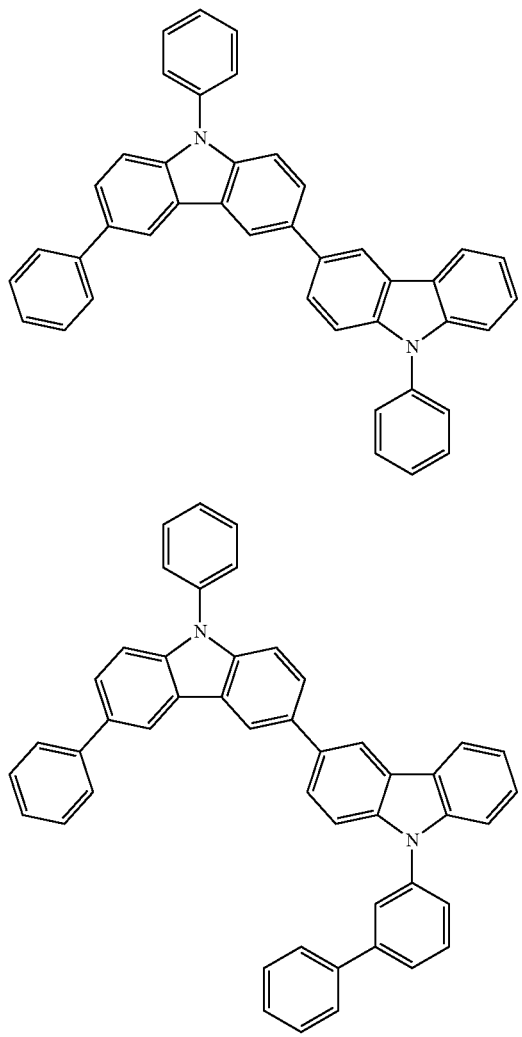
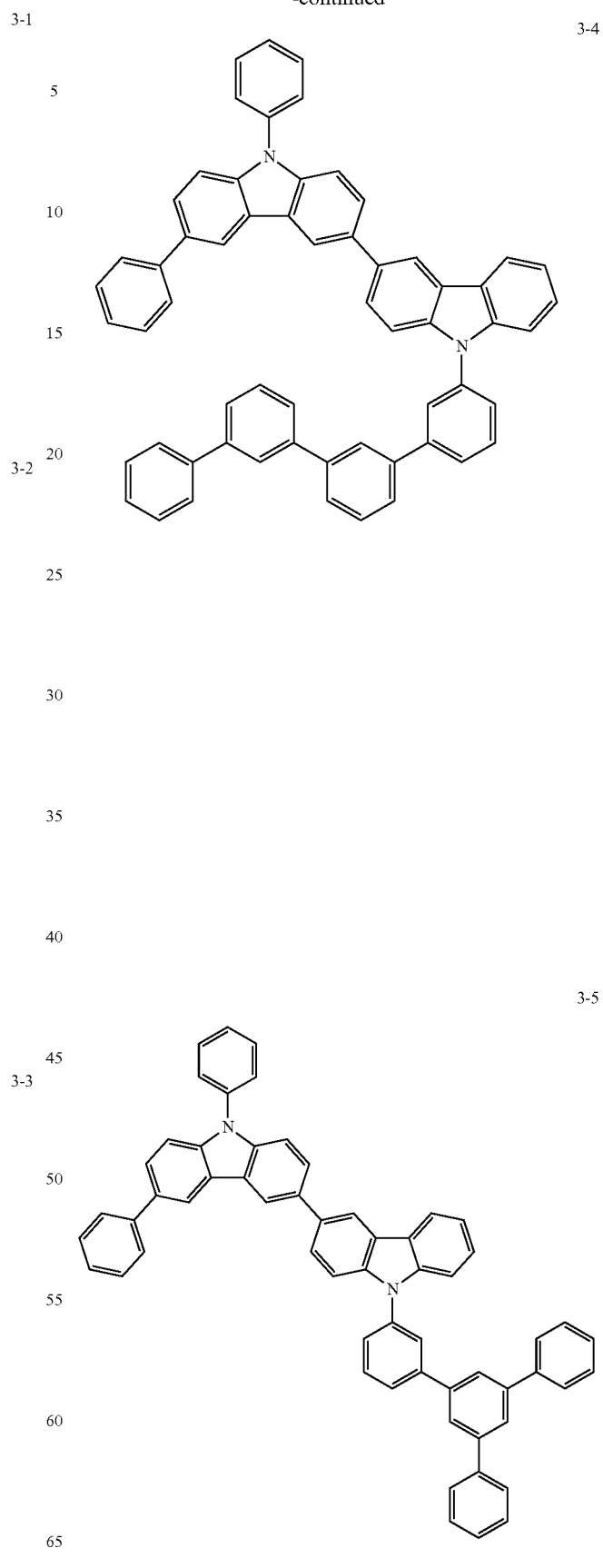

3-6
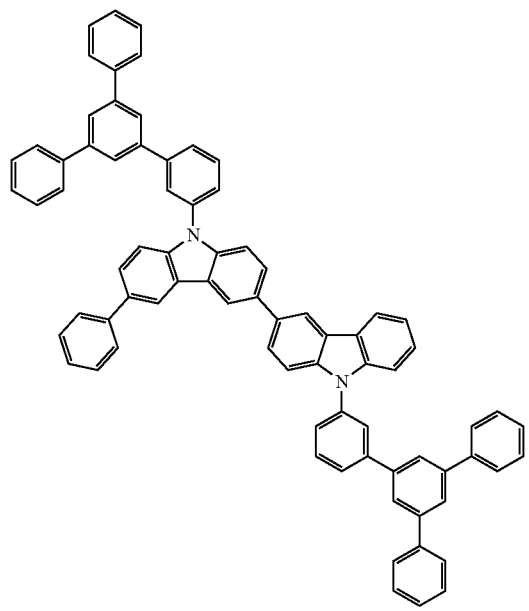
3-7
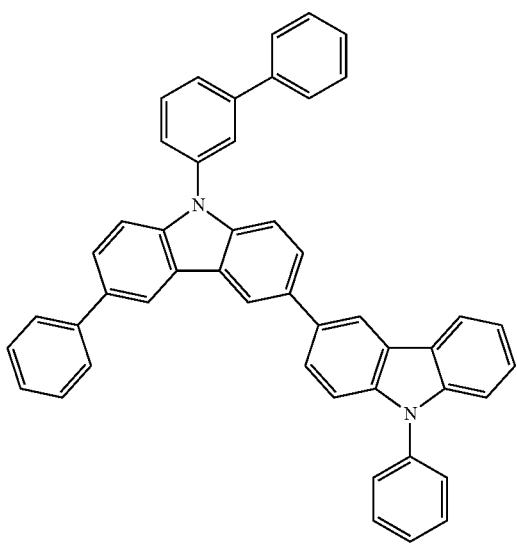
3-8
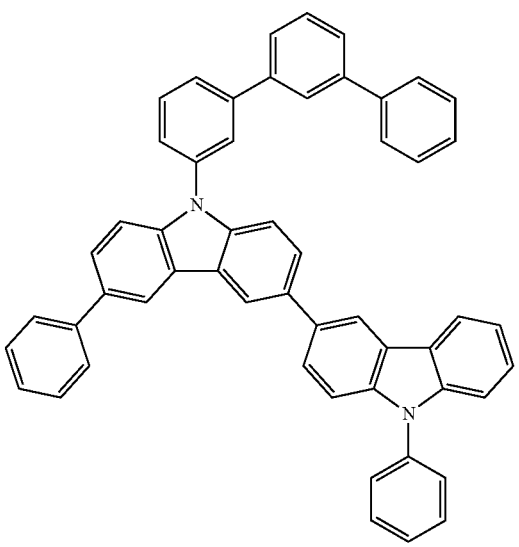
3-9
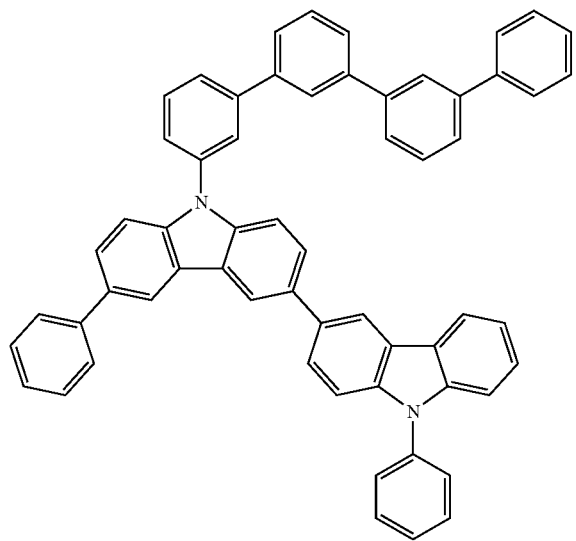

3-10
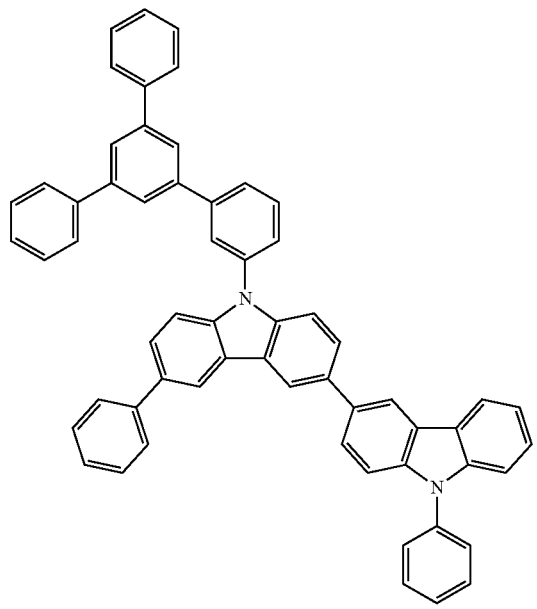
3-11
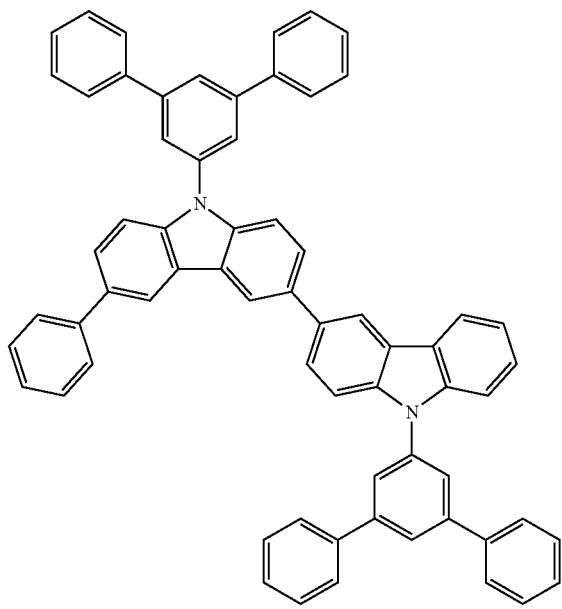
3-12
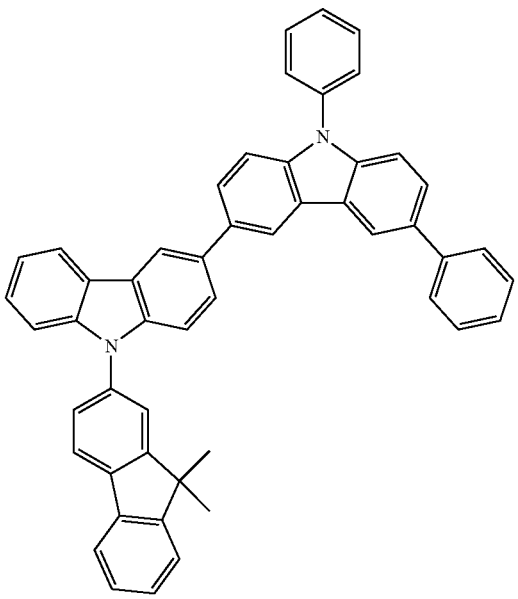
3-13
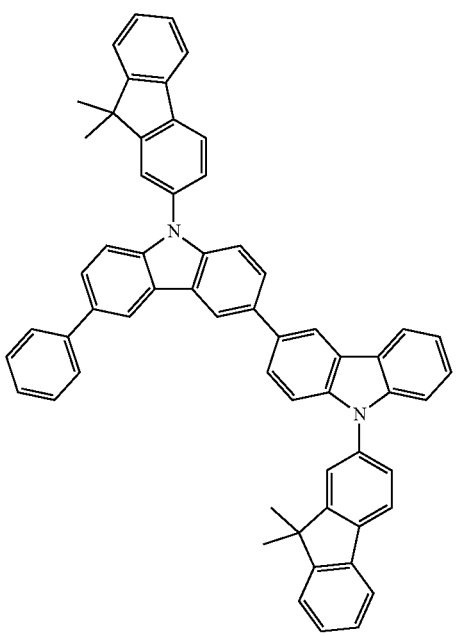

3-14
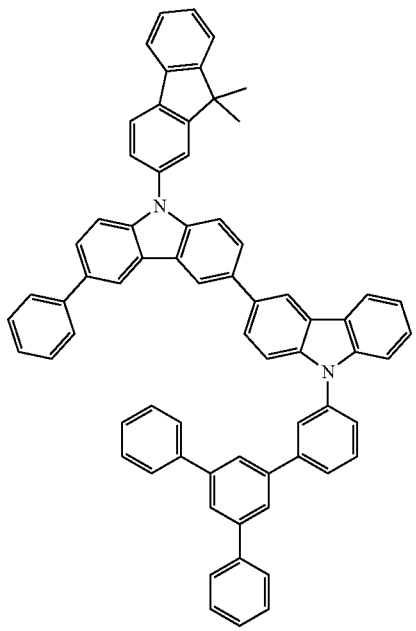
3-15
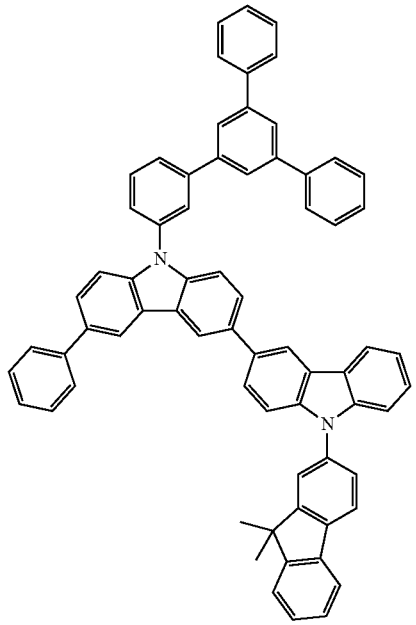
3-16
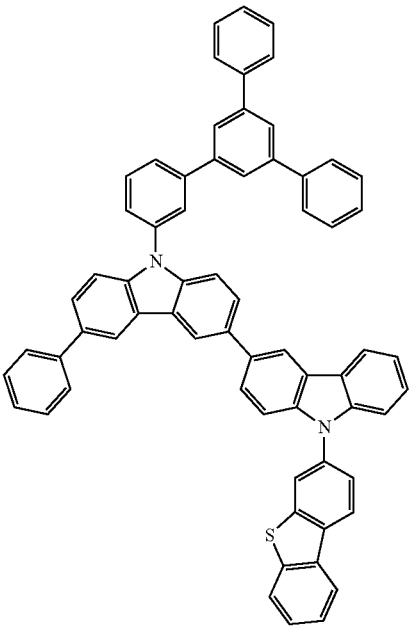
3-17
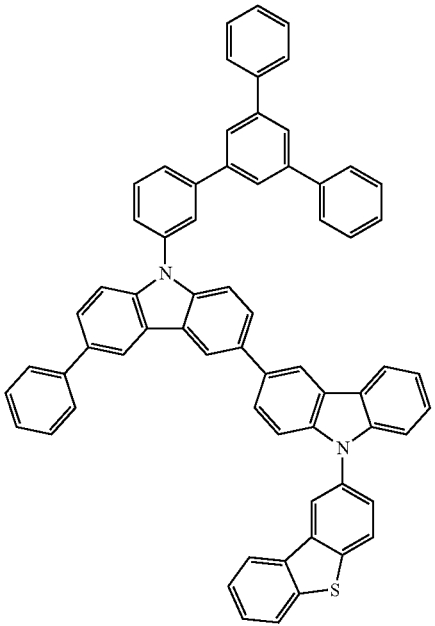

3-18
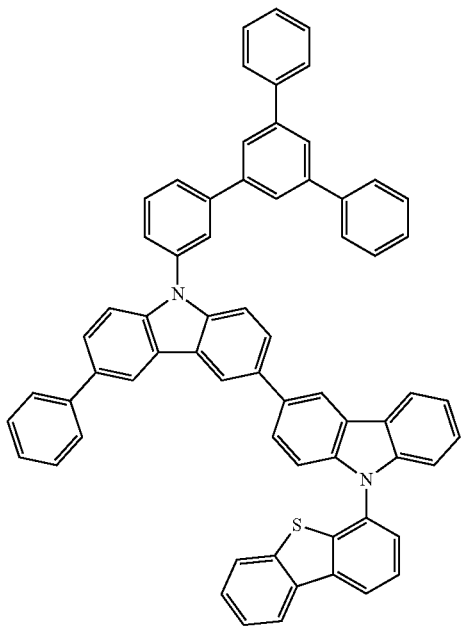
3-19
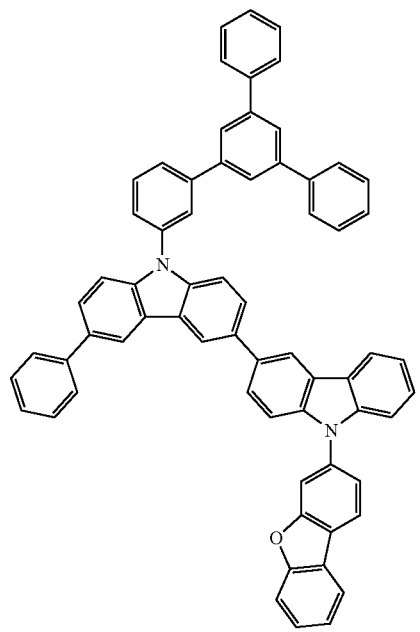
3-20
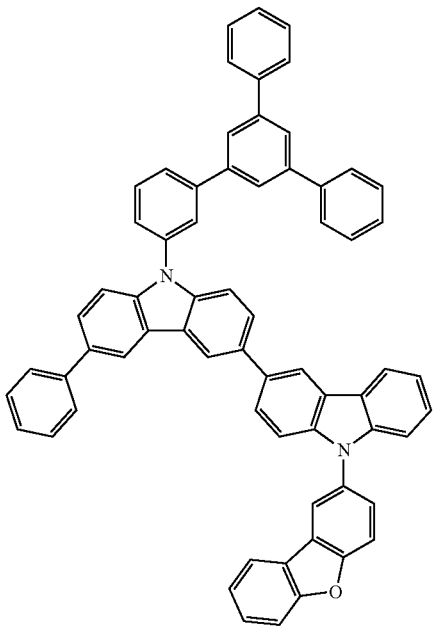
3-21
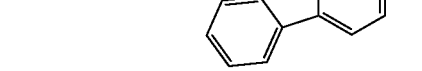

-continued
3-22
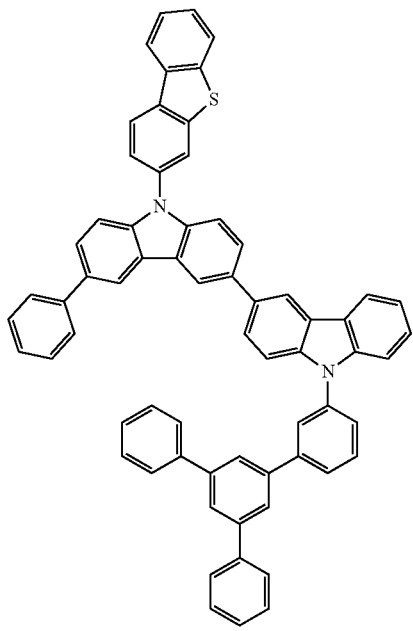
3-23
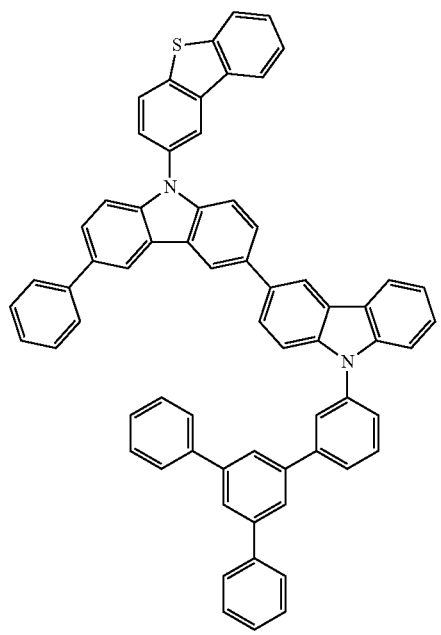
3-24
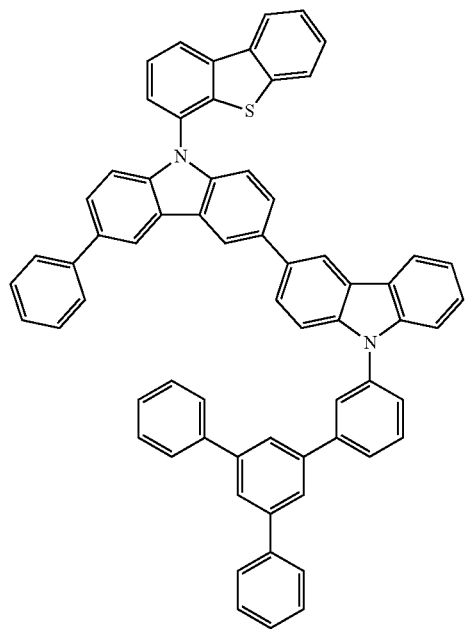
3-25
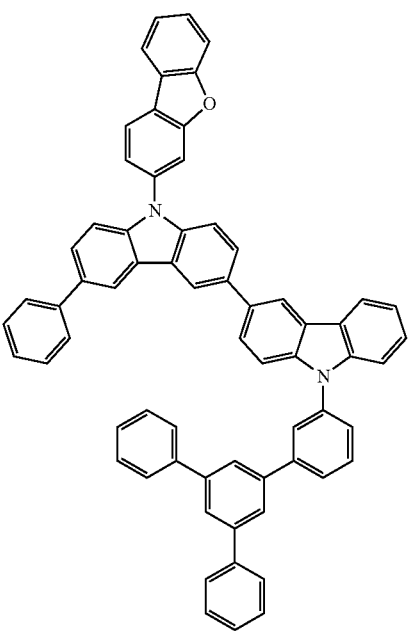

3-26
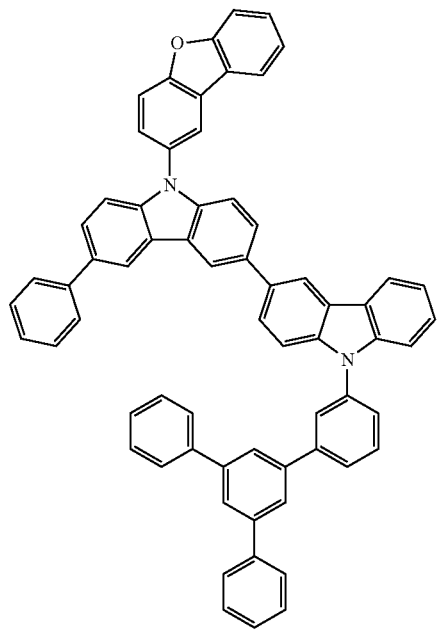
3-27
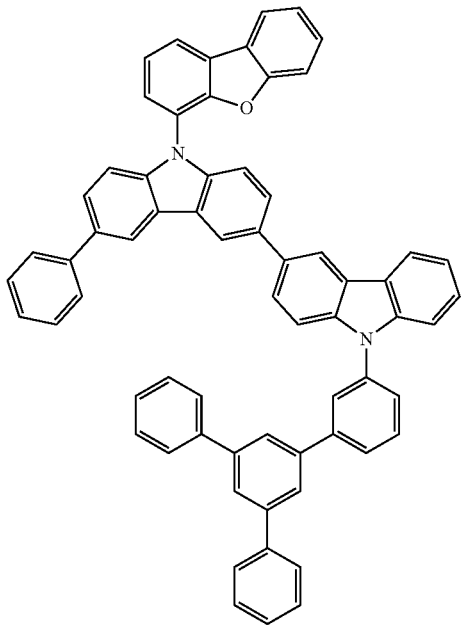
3-28
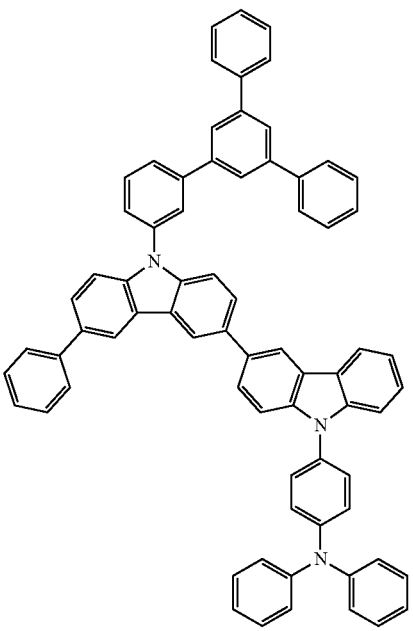
3-29
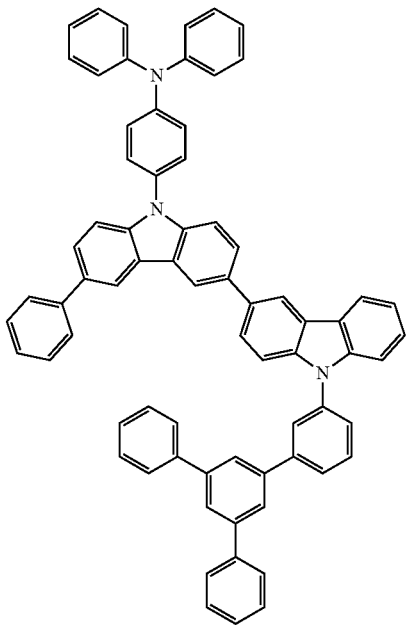

3-30
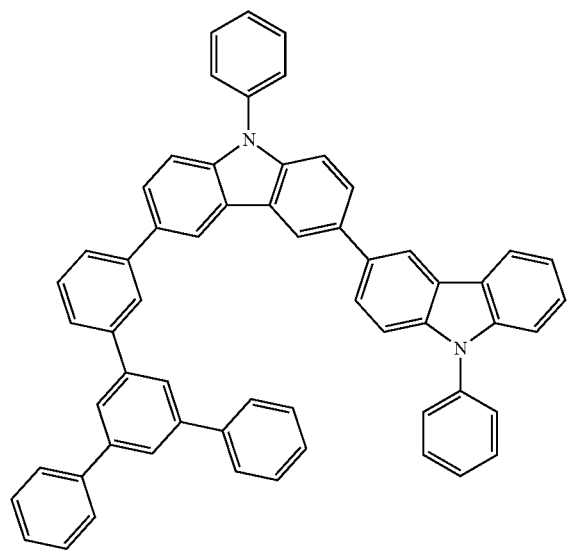
3-33
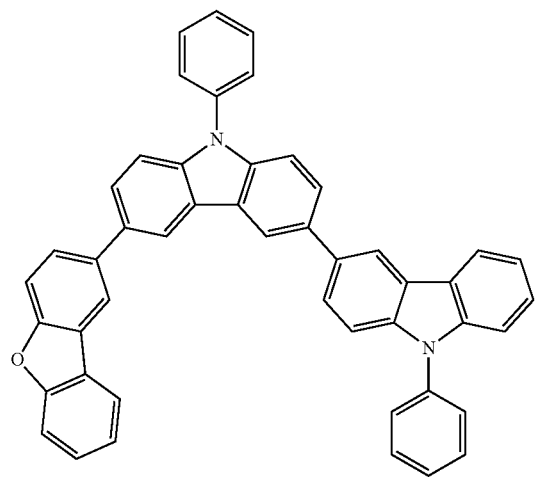
3-31
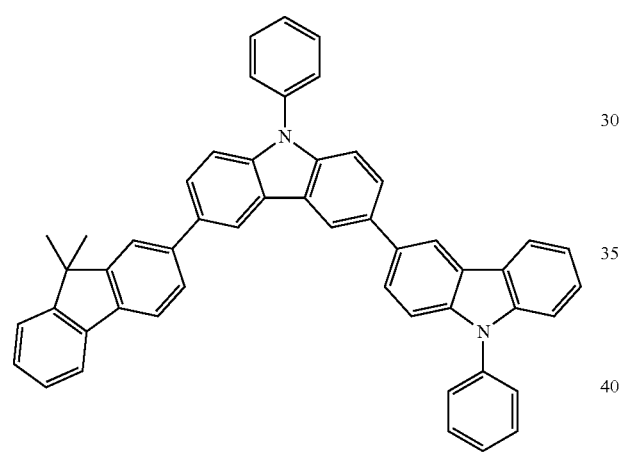
3-34
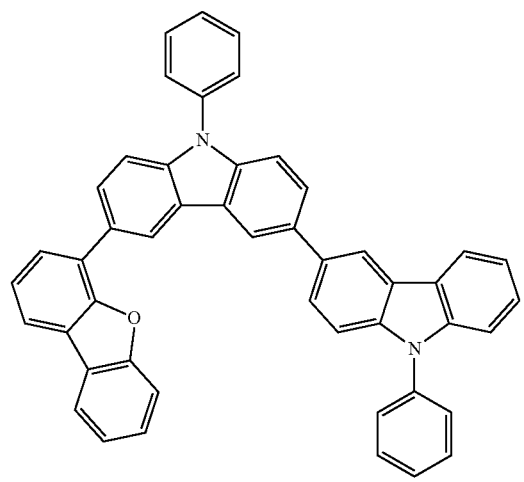
3-32
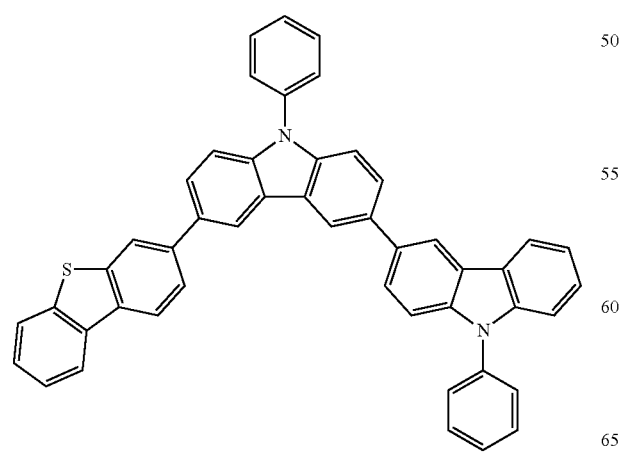
3-35
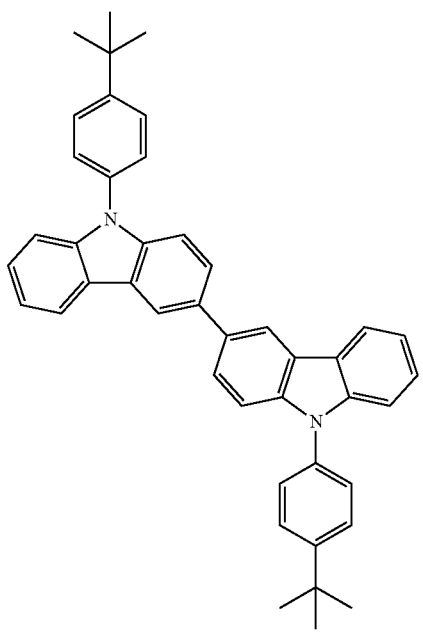

3-36

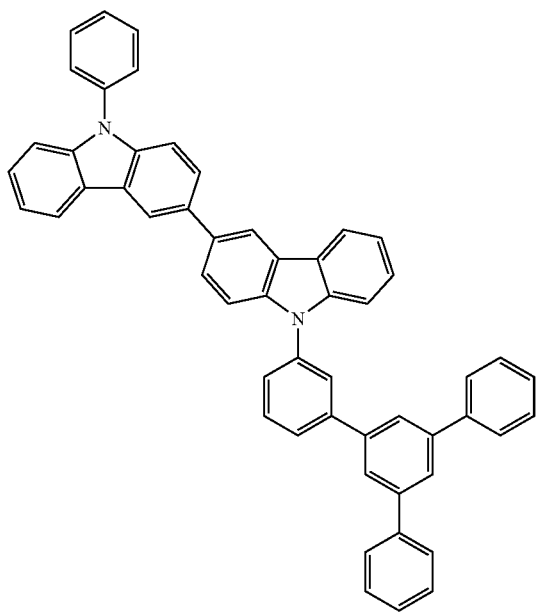

3-37

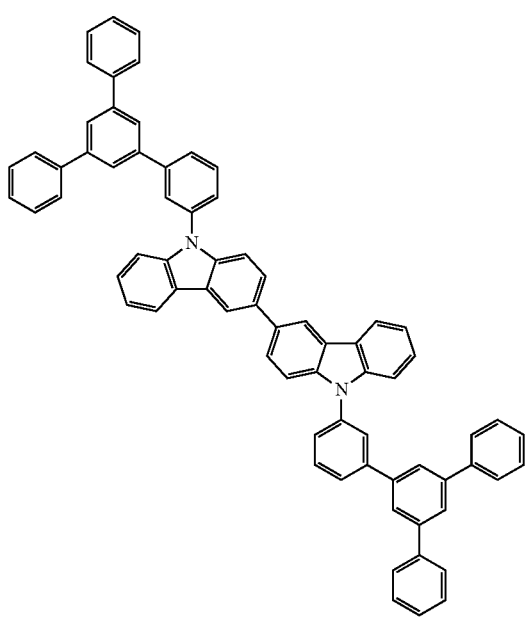

3-38

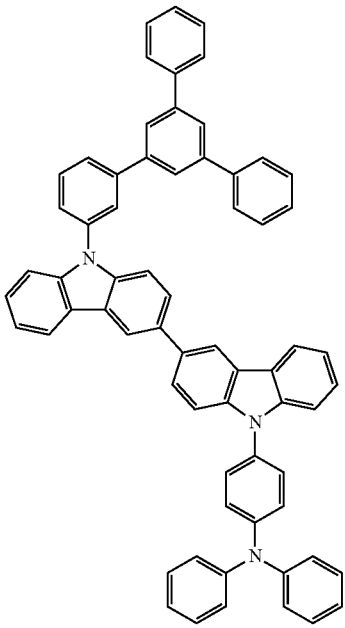

3-39

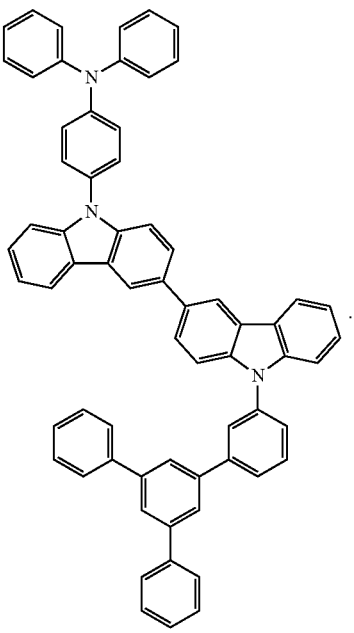

The luminescent host material may be one compound belonging to Formula (1) or a mixture of two or more different compounds belonging to Formula (1)(for example, a mixture of two different compounds belonging to Formula (1)).

In an embodiment, the luminescent host material may be a compound represented by Formula (2) or a compound represented by Formula (3).

In one or more embodiments, the luminescent host material may be a mixture of at least one compound represented by Formula (1), in which at least one of $A_1$ to $A_3$ is each independently represented by Formula (2-A), and at least one compound may have a biscarbazole backbone.

In one or more embodiments, the luminescent host material may be a mixture of at least one compound represented by Formula (2) and at least one compound represented by Formula (3).

In one or more embodiments, the luminescent host material may be a mixture of at least one compound represented by Formula (2), in which at least one of $A_1$ to $A_3$ is each independently represented by Formula (2-A), and at least one compound represented by Formula (3).

A molecular weight of the luminescent host material may be about 5,000 grams per mole (g/mol) or less, for example, about 2,000 g/mol or less. In an embodiment, the molecular weight of the luminescent host material may be in a range of about 300 g/mol to about 2,000 g/mol. While not wishing to be bound by theory, it is understood that when the molecular weight of the luminescent host material is within this range, the luminescent host material may be easily dispersed in the ink composition for an organic light-emitting device.

Also, the luminescent host material may be prepared by appropriately selecting known organic synthesis methods.

In addition to the compound represented by Formula (1), other luminescent host materials may be additionally used as the luminescent host material.

Although not particularly limited, the other luminescent host materials may include a silane compound such as 1,4-bis(triphenylsilyl)benzene (UGH-2) or 1,3-bis(triphenylsilyl)benzene, a phosphine compound such as 2,8-bis(diphenylphosphoryl)dibenzo[b,d]thiophene (PPT) or 2,7-bis(diphenylphosphoryl)-9,9'-spirofluorene (SPPO13), a triphenylamine derivative, a benzimidazole derivative, a quinoline derivative, a perylene derivative, a pyridine derivative, a pyrimidine derivative, a triazine derivative, a quinoxaline derivative, a diphenyl quinone derivative, or a nitro-substituted-fluorene derivative.

Also, the term "low-molecular-weight" used herein means that a weight average molecular weight ($M_w$) is 5,000 Daltons (Da) or less. The term "high-molecular-weight (polymeric)" as used herein means that a weight average molecular weight ($M_w$) is greater than 5,000 Da. A weight average molecular weight ($M_w$) of a low-molecular-weight compound is a value measured by using a time-of-flight mass spectrometry (TOF-MS) system (manufactured by Shimadzu), and a weight average molecular weight ($M_w$) of a high-molecular-weight (polymeric) compound is a value measured by a high-speed gel permeation chromatography (GPC) system (manufactured by Tosoh Corporation) using polystyrene as a standard material.

An amount of the luminescent host material in the ink composition for an organic light-emitting device may be in a range of about 0.1 parts by weight to about 50 parts by weight, for example, about 0.1 parts by weight to about 10 parts by weight, based on 100 parts by weight of the ink composition. While not wishing to be bound by theory, it is understood that when the amount of the luminescent host material is within this range, a uniform film may be formed by using the ink composition for an organic light-emitting device, and precipitation of the luminescent host material in the ink composition for an organic light-emitting device may be substantially suppressed.

Luminescent Impurities

The ink composition for an organic light-emitting device may further include, in addition to the luminescent host material described above, luminescent impurities.

The luminescent impurities may be a phosphorescent dopant or a fluorescent dopant.

Examples of the luminescent impurities may include a perylene and a derivative thereof, a rubrene and a derivative thereof, a coumarin and a derivative thereof, 4-dicyanomethylene-2-(p-dimethylaminostyryl)-6-methyl-4H-pyran (DCM) and a derivative thereof, an iridium (Ir) complex such as bis[2-(4,6-difluorophenyl)pyridinate]picolinate iridium (III) (FIrpic), bis(1-phenylisoquinoline)(acetylacetonate)iridium (III) (Ir(piq)$_2$(acac)), tris(2-(3-p-xylyl)phenyl)pyridine iridium) (III), or tris(2-phenylpyridine)iridium (III) (Ir(ppy)$_3$), an osmium (Os) complex, and a platinum complex.

Solvent

The ink composition for an organic light-emitting device may include at least one solvent selected from an aromatic ether, an aromatic ester, and an aromatic ketone.

Although not particularly limited, the aromatic ether may use a compound represented by Formula (4):

Formula (4)

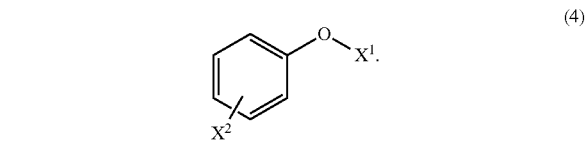

(4)

In Formula (4), $X^1$ may be a $C_1$-$C_6$ alkyl group, and $X^2$ may be a hydrogen atom, a methyl group, an ethyl group, or a propyl group.

Specific examples of the aromatic ether may include an anisole, a 4-methoxy toluene, a p-ethyl anisole, a p-propyl anisole, a p-butyl anisole, a phenetole, a 1-propyl-4-methoxybenzene, an iso-propyl phenyl ether, a phenyl propyl ether, a butyl phenyl ether, and a pentyl phenyl ether.

Although not particularly limited, the aromatic ester may use a compound represented by Formula (5):

Formula (5)

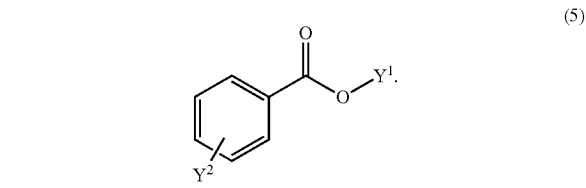

(5)

In Formula (5), $Y^1$ may be a $C_1$-$C_3$ alkyl group, and $Y^2$ may be a hydrogen atom, a methyl group, or an ethyl group.

Specific examples of the aromatic ester may include a methyl benzoate, a methyl 4-methyl benzoate, an ethyl benzoate, and an iso-propyl benzoate.

Although not particularly limited, the aromatic ketone may use a compound represented by Formula (6):

Formula (6)

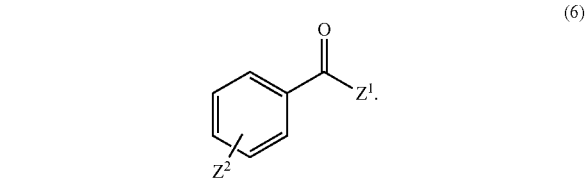

(6)

In Formula (6), $Z^1$ may be a $C_1$-$C_4$ alkyl group, and $Z^2$ may be a hydrogen atom, a methyl group, or an ethyl group.

Specific examples of the aromatic ketone may include an acetophenone, a 4'-methylacetophenone, a propiophenone, a 4'-methylpropiophenone, a butylophenone, and a 4'-methylbutylophenone.

In an embodiment, the ink composition for an organic light-emitting device may include an aromatic ether and/or an aromatic ester so as to improve luminescent efficiency and inkjet discharge stability of the organic light-emitting device.

In one or more embodiments, an aromatic ether that does not have a polar group, for example, a carbonyl group, which inhibits charge transport of the luminescent host material, may be used as a solvent for the ink composition, even if it is remained in a coating film.

A solubility of the solvent in water at a temperature of 20° C. may be about 1% or less, for example, about 0.9% or less, and in another example, about 0.7% or less. While not wishing to be bound by theory, it is understood that when the solubility of the solvent in water at a temperature of 20° C. is within this range, an organic light-emitting device including a film formed by using the ink composition including the solvent may substantially prevent generation of dark spots and short, durability deterioration, and the like.

A viscosity of the solvent may be in a range of about 1.0 millipascal seconds (mPa·s) to about 3.5 mPa·s, for example, about 1.2 mPa·s to about 3.0 mPa·s, and in another example, about 1.5 mPa·s to about 2.5 mPa·s. While not wishing to be bound by theory, it is understood that when the viscosity of the solvent is within this range, it is possible to substantially prevent a nozzle of an inkjet head from being clogged during inkjet printing using the ink composition for an organic light-emitting device, and small droplets of the ink composition for an organic light-emitting device may be easily discharged from an inkjet head.

A surface tension of the solvent may be in a range of about 20 millinewtons per meter (mN/m) to about 45 mN/m, for example, about 25 mN/m to about 43 mN/m, and in another example, 28 mN/m to about 40 mN/m. While not wishing to be bound by theory, it is understood that when the surface tension of the solvent is within this range, wettability of the ink composition for an organic light-emitting device on a surface of a nozzle is controlled as desired. Accordingly, a phenomenon in which the ink composition for an organic light-emitting device is attached around the nozzle, and thus, a flow direction of a droplet is bent is substantially prevented. Also, since a meniscus shape at a front end of the nozzle is stable, it is possible to easily control a discharge amount and a discharge timing of the ink composition for an organic light-emitting device.

Also, the solvents described above may be used alone or in a combination of two or more solvents.

In an embodiment, the solvent may include two or more different compounds selected from an aromatic ether, an aromatic ester, and an aromatic ketone.

For example, the solvent may be an aromatic ether, an aromatic ester, or an aromatic ketone, as described above, or may be a mixture of the aromatic ether and the aromatic ester, a mixture of the aromatic ester and the aromatic ketone, a mixture of the aromatic ether and the aromatic ketone, or a mixture of the aromatic ether, the aromatic ester, and the aromatic ketone.

In an embodiment, the solvent may include at least one of an aromatic ether and an aromatic ester.

Also, for the purpose of suppressing the drying of the ink composition for an organic light-emitting device at the nozzle of the inkjet head, a vapor pressure of the solvent at a temperature of 25° C. may be about 1 mmHg or less, for example, about 0.5 mmHg or less, and in another example, about 0.01 to mmHg to about 0.5 mmHg. While not wishing to be bound by theory, it is understood that when the vapor pressure of the solvent is within these ranges, it is possible to substantially prevent deterioration in luminescent efficiency and durability of an organic light-emitting device, even when the solvent exists in the coating film after drying.

On the other hand, in order to improve leveling during drying of inkjet-discharged substances or in order to improve solubility of the luminescent material, the ink composition for an organic light-emitting device may further include other solvents as well as the solvent described above.

As the other solvents, any solvents may be used as long as these solvents are capable of dissolving the luminescent material. Specific examples of the solvents may include: a halogen-containing solvent such as dichloromethane, dichloroethane, chloroform, carbon tetrachloride, tetrachloroethane, trichloroethane, chlorobenzene, dichlorobenzene, or chlorotoluene; a hydrocarbon solvent having 6 or more carbon atoms, such as hexane, heptane, octane, nonane, decane, or undecane; and an aromatic solvent such as benzene, toluene, xylene, ethylbenzene, propylbenzene, butylbenzene, pentylbenzene, hexylbenzene, nonylbenzene, decylbenzene, undecylbenzene, dodecylbenzene, tetralin, or cyclohexylbenzene.

Also, the other solvents described above may be used alone or in a combination of two or more solvents.

Additive

The ink composition for an organic light-emitting device may, if necessary, include an additive, such as a leveling agent or a viscosity modifier, so as to improve inkjet discharge performance or improve leveling during drying of inkjet-discharged substances.

Leveling Agent

Although not particularly limited, the leveling agent may be a silicon-containing compound, a fluorine-containing compound, a siloxane-containing compound, a non-ionic surfactant, an ionic surfactant, or a titanate coupling agent. For example, a silicon-containing compound and/or a fluorine-containing compound may be used as the leveling agent.

Although not particularly limited, the silicon compound may be a dimethyl silicone, a methyl silicone, a phenyl silicone, a methyl phenyl silicone, an alkyl-modified silicone, an alkoxy-modified silicone, or a polyether-modified silicone. For example, a dimethyl silicone or a methyl phenyl silicone may be used as the silicon compound.

Although not particularly limited, the fluorine-containing compound may be a polytetrafluoroethylene, a polyvinylidene fluoride, a fluoroalkyl methacrylate, a perfluoropolyether, or a perfluoroalkylethylene oxide. For example, a polytetrafluoroethylene may be used as the fluorine-containing compound.

Although not particularly limited, the siloxane-containing compound may be a dimethylsiloxane compound (product name: KF96L-1, KF96L-5, KF96L-10, KF96L-100, manufactured by Shinetsu Silicon Inc.).

In an embodiment, a silicon-containing compound, a fluorine-containing compound and/or a siloxane-containing compound among the leveling agents described above may be used. In one or more embodiments, a siloxane-containing compound may be used.

Also, the leveling agents described above may be used alone or in a combination of two or more leveling agents.

Although an amount of the leveling agent changes according to desired performance, the amount of the leveling agent may be in a range of about 0.001 parts by weight to about 5 parts by weight, for example, about 0.001 parts by weight to about 1 part by weight, based on 100 parts by weight of the ink composition for an organic light-emitting device. While not wishing to be bound by theory, it is understood that when the amount of the leveling agent is within this range, leveling of a coating film and luminescent efficiency of a light-emitting device may be improved.

Viscosity Modifier

Although not particularly limited, the viscosity modifier may be a thermoplastic resin such as a poly(α-methylstyrene), a polystyrene, a styrene-acrylonitrile copolymer, a styrene-butadiene-acrylonitrile copolymer, a polymethylmethacrylate, a methacrylate-styrene copolymer, or a polycarbonate. For example, a poly(α-methylstyrene), a polystyrene, a styreneacrylonitrile copolymer, a styrene-butadiene-acrylonitrile copolymer, or a polymethylmethacrylate may be used as the viscosity modifier.

The viscosity modifiers described above may be used alone or in a combination of two or more viscosity modifiers.

Although an amount of the viscosity modifier changes according to desired performance, the amount of the viscosity modifier may be in a range of about 0.001 parts by weight to about 5 parts by weight, for example, about 0.01 parts by weight to about 1 parts by weight, based on 100 parts by weight of the ink composition for an organic light-emitting device. While not wishing to be bound by theory, it is understood that when the amount of the viscosity modifier is within this range, the aggregation of the luminescent host material in the ink composition for an organic light-emitting device may be substantially suppressed, the luminescent efficiency of an organic light-emitting device may be improved, and a flow shape of droplets of the inkjet composition may be improved.

Organic Light-Emitting Device

In an embodiment, an organic light-emitting device is provided. The organic light-emitting device includes an anode, an emission layer, and a cathode. The emission layer may include a luminescent host material, and the luminescent host material may include at least one compound represented by Formula (1).

Also, the organic light-emitting device may further include one or more layers, such as a hole injection layer, a hole transport layer, an electron transport layer, and an electron injection layer. Also, the organic light-emitting device may further include known members such as an encapsulation member.

Hereinafter, each component of the organic light-emitting device will be described in detail.

Anode

Although not particularly limited, a metal such as gold (Au), copper iodide (CuI), indium tin oxide (ITO), tin oxide ($SnO_2$), zinc oxide (ZnO), or the like may be used as the cathode. These materials may be used alone or in a combination of two or more materials.

Although not particularly limited, a film thickness of the cathode may be in a range of about 10 nm to about 1,000 nm, for example, about 10 nm to about 200 nm.

The anode may be formed by deposition or sputtering. In this case, pattern formation may be performed by using photolithography or a mask.

Hole Injection Layer

The hole injection layer is an optional component in the organic light-emitting device and has a function of receiving holes from the anode. The holes received from the anode are transported to the hole transport layer or the emission layer.

A hole-injecting material may be a phthalocyanine compound such as copper phthalocyanine, a triphenylamine derivative such as 4,4',4"-tris[phenyl(m-tolyl)amino]triphenylamine, a cyano compound such as 1,4,5,8,9,12-hexaazatriphenylene hexacarbonitrile or 2,3,5,6-tetrafluoro-7,7,8,8-tetracyanoquinodimethane, an oxide such as a vanadium oxide or a molybenium oxide, amorphous carbon, a conductive polymer such as a polyaniline (emeraldine), a poly(3,4-ethylenedioxythiophene)-poly(sterene sulfonic acid) (PEDOT-PSS), or a polypyrrole, but embodiments of the present disclosure are not limited thereto. For example, a conductive polymer, for example, PEDOT-PSS, may be used as the hole-injecting material.

A film thickness of the hole injection layer may be in a range of about 0.1 nm to about 5 micrometers (μm), but embodiments of the present disclosure are not limited thereto.

The hole injection layer may have a single-layered structure or a multi-layered structure including two or more layers.

Hole Transport Layer

The hole transport layer is an optional component in the organic light-emitting device and has a function of efficiently transporting holes. Also, the hole transport layer may have a function of preventing transport of electrons. In general, the hole transport layer receives holes from the anode or the hole injection layer and transports the holes to the emission layer.

Although not particularly limited, a hole-transporting material usable for the hole transport layer may be a low-molecular-weight triphenylamine derivative such as N,N'-diphenyl-N, N'-di(3-methylphenyl)-1,1'-biphenyl-4,4'-diamine (TPD), 4,4'-bis[N-(1-naphthyl)-N-phenylamino]biphenyl (α-NPD), or 4,4',4"-tris (3-methylphenylphenylamino) triphenylamine (m-MTDATA); or a high-molecular-weight compound such as a polyvinyl carbazole or a diamine polymer polymerized by introducing a substituent into a triarylamine derivative. Of these, as the hole-transporting material, a triarylamine derivative, or a high-molecular-weight polymeric compound obtained by polymerizing a triphenylamine derivative introduced with a substituent, for example, a diamine polymer having a fluorene backbone may be used.

Although not particularly limited, a film thickness of the hole transport layer may be in a range of about 1 nm to about 5 μm, for example, about 5 nm to about 1 μm, and in another example, about 10 nm to about 500 nm.

Emission Layer

The emission layer has a function of causing light emission by using energy generated by recombination of holes and electrons injected into the emission layer.

As described above, the emission layer may include a luminescent host material, and the luminescent host material may include at least one compound represented by Formula (1). The luminescent host material may, if necessary, further include other luminescent host materials described above.

Also, if necessary, the emission layer may include, in addition to the luminescent host material, a luminescent impurity material.

Since the luminescent impurity material has been described above, a further description thereof will be omitted.

Although not particularly limited, a film thickness of the emission layer may be in a range of about 2 nm to about 30 µm, for example, about 10 nm to about 20 µm, and in another example, about 15 nm to about 15 µm. In an embodiment, the film thickness of the emission layer may be in a range of about 15 nm to about 200 nm. While not wishing to be bound by theory, it is understood that when the film thickness of the emission layer is within these ranges, the film thickness may be controlled with high precision.

Electron Transport Layer

The electron transport layer is an optional component in the organic light-emitting device and has a function of efficiently transporting electrons. Also, the electron transport layer may have a function of preventing transport of holes. In general, the electron transport layer receives electrons from the cathode or the electron injection layer and transports the electrons to the emission layer.

Although not particularly limited, an electron-transporting material usable for the electron transport layer may be a metal complex having a quinoline backbone or a benzoquinoline backbone, such as tris(8-quinolinato)aluminum (Alq), tris(4-methyl-8-quinolinolato)aluminum (Almq$_3$), bis (10-hydroxybenzo[h]quinolinato)beryllium (BeBq$_2$), bis(2-methyl-8-quinolinolato)(p-phenylphenolate)aluminum (BAlq), bis(8-quinolinolato)zinc (Znq), or 8-hydroxyquinolinatolithium (Liq); a metal complex having a benzoxazoline backbone, such as bis[2-(2'-hydroxyphenyl)benzoxazolate]zinc (Zn(BOX)$_2$); a metal complex having a benzothiazoline backbone, such as bis[2-(2'-hydroxyphenyl) benzothiazolate]zinc (Zn(BTZ)$_2$); a polyazole derivative such as 2-(4-biphenylyl)-5-(4-tert-butylphenyl)-1,3,4-oxadiazole (PBD), 3-(4-biphenylyl)-4-phenyl-5-(4-tert-butylphenyl)-1,2,4-triazole (TAZ), 1,3-bis[5-(p-tert-butylphenyl)-1, 3,4-oxadiazole-2-yl]benzene (OXD-7), 9-[4-(5-phenyl-1,3, 4-oxadiazole-2-yl)phenyl]carbazole (CO11), 2,2',2"-(1,3,5-benzenetriyl)tris(1-phenyl-1H-benzimidazole) (TPBI), or 2-[3-(dibenzothiophene-4-yl)phenyl]-1-phenyl-1H-benzimidazole (mDBTBIm-II); a benzimidazole derivative; a quinoline derivative; a perylene derivative; a pyridine derivative; a pyrimidine derivative; a triazine derivative; a quinoxaline derivative; a diphenylquinone derivative; or a nitro-substituted-fluorene derivative, KLET-03 (product name, manufactured by Chemipro Kasei). Of these, the electron-transporting material may use a benzimidazole derivative, a pyridine derivative, a pyrimidine derivative, a triazine derivative, or a phenanthroline derivative.

The electron-transporting materials described above may be used alone or in a combination of two or more electron-transporting materials.

Although not particularly limited, a film thickness of the electron transport layer may be in a range of about 5 nm to about 5 µm, for example, about 5 nm to about 200 nm.

The electron transport layer may have a single-layered structure or a multi-layered structure including two or more layers.

Electron Injection Layer

The electron injection layer is an optional component in the organic light-emitting device and has a function of receiving electrons from the cathode. In general, the electrons received from the cathode are transported to the electron transport layer or the emission layer.

Although not particularly limited, an electron-injecting material usable for the electron injection layer may be an alkali metal such as lithium or calcium; a metal such as strontium or aluminum; an alkali metal salt such as lithium fluoride or sodium fluoride; an alkali metal compound such as 8-hydroxyquinolinatolithium (LiQ); an alkaline earth metal salt such as magnesium fluoride; or an oxide such as aluminum oxide. Of these, the alkali metal, the alkali metal salt, and the alkali metal compound are preferable as the electron-injecting material, and the alkali metal salt or the alkali metal compound may be used as the electron-injecting material.

The electron-injecting materials described above may be used alone or in a combination of two or more electron-injecting materials.

Although not particularly limited, a film thickness of the electron injection layer may be in a range of about 0.1 nm to about 5 µm.

The electron injection layer may have a single-layered structure or a multi-layered structure including two or more layers.

Cathode

Although not particularly limited, the cathode may include lithium, sodium, magnesium, aluminum, a sodium-potassium alloy, a magnesium/aluminum mixture, a magnesium/indium mixture, an aluminum/aluminum oxide (Al$_2$O$_3$) mixture, and a rare earth metal. These materials may be used alone or in a combination of two or more materials.

The cathode may be formed by deposition or sputtering.

Although not particularly limited, a film thickness of the cathode may be in a range of about 10 nm to about 1,000 nm, for example, about 10 nm to about 200 nm.

Other Layers

Also, the organic light-emitting device may include layers other than the above-described layers. For example, the organic light-emitting device may include a hole blocking layer and an electron blocking layer. The hole blocking layer is a layer for blocking movement of holes from each layer such as the emission layer and is generally disposed on a side of the emission layer closer to the cathode. Also, the electron blocking layer is a layer for blocking movement of electrons from each layer such as the emission layer and is generally disposed on a side of the emission layer closer to the cathode. Although not particularly limited, various known materials may be used for forming the hole blocking layer and the electron blocking layer. Also, a material for forming the hole blocking layer may be HBL-1 represented by the following structural formula.

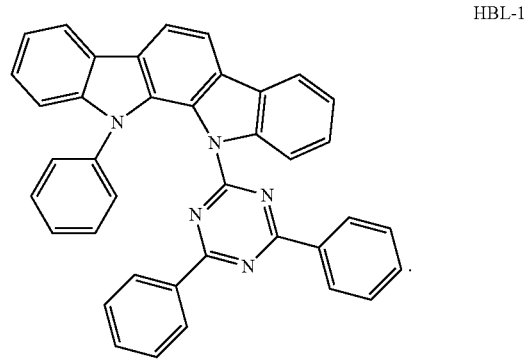 [SMILES: c1ccc(-c2nc(-c3ccccc3)nc(-n3c4ccccc4c4ccc5c6ccccc6n(-c6ccccc6)c5c43)n2)cc1]

HBL-1

Method of Manufacturing Organic Light-Emitting Device

According to one or more embodiments, a method of manufacturing an organic light-emitting device is provided. The method of manufacturing an organic light-emitting device includes a process (hereinafter, referred to as an emission layer forming process) of forming an emission layer by coating the ink composition for an organic light-emitting device on a support by inkjet printing.

Emission Layer Forming Process

The emission layer forming process is a process of forming an emission layer by coating the ink composition for an organic light-emitting device on a support by inkjet printing.

Hereinafter, the emission layer forming process according to an embodiment will be described with reference to the accompanying drawing.

The FIGURE is a partial schematic cross-sectional view for describing a process of forming a coating film by inkjet printing. Referring to the FIGURE, the organic light-emitting device includes a substrate 1, a plurality of anodes 2 disposed on the substrate 1, and a hole transport layer 4 disposed on the anodes 2. In this case, laminates of the plurality of anodes 2 and the hole transport layer 4 on the substrate 1 are separated by banks 3. When the ink composition for an organic light-emitting device is discharged from a nozzle 6 of an inkjet head 7, a coating film 5 of the ink composition for an organic light-emitting device is formed on the hole transport layer 3. The obtained coating film is dried to form an emission layer.

Ink Composition for Organic Light-Emitting Device

Since the ink composition described above is usable as the ink composition for an organic light-emitting device, a description thereof will be omitted.

Support

The support is a constituting layer of the organic light-emitting device adjacent to the emission layer and is different according to an organic light-emitting device to be manufactured. For example, in the case of manufacturing an organic light-emitting device including an anode, an emission layer, and a cathode, the support is the anode or the cathode. Also, in the case of manufacturing an organic light-emitting device including an anode, a hole injection layer, an emission layer, an electron injection layer, and a cathode, the support is the hole injection layer or the electron transport layer. As described above, the support may be an anode, a hole injection layer, a hole transport layer, an electron transport layer, an electron injection layer, or a cathode, for example, an anode, a hole injection layer, or a hole transport layer. In another example, the support may be a hole injection layer or a hole transport layer. For example, the support may be a hole transport layer.

Also, a bank may be formed in the support. Due to the bank, the emission layer may be formed only in desired portions.

A height of the bank may be in a range of about 0.1 µm to about 5.0 µm, for example, about 0.2 µm to about 3.0 µm. For example, the height of the bank may be in a range of about 0.2 µm to about 2.0 µm.

Also, a width of an opening of the bank may be in a range of about 10 µm to about 200 µm, for example, about 30 µm to about 200 µm, and in another example, about 50 µm to about 100 µm.

Also, a length of the opening of the bank may be in a range of about 10 µm to about 400 µm, for example, about 20 µm to about 200 µm, and in another example, about 50 µm to about 200 µm.

Also, a taper angle of the bank may be in a range of about 10° to about 100°, for example, about 10° to about 90°, and in another example, about 10° to about 800.

Coating

The coating is performed by inkjet printing. For example, the ink composition for an organic light-emitting device is discharged from the nozzle of the inkjet head toward the support.

In this case, a discharge amount of the ink composition for an organic light-emitting device may be in a range of about 1 picoliters (pL) to about 50 pL each time, for example, about 1 pL to about 30 pL each time, and in another example, about 1 pL to about 20 pL each time.

An diameter of an opening of the inkjet head may be in a range of about 5 µm to about 50 µm, for example, about 10 µm to about 30 µm, to minimize nozzle clogging or improve discharge precision.

Although not particularly limited, a temperature during the forming of the coating film may be in range of about 10° C. to about 50° C., for example, about 15° C. to about 40° C., and in another example, about 15° C. to about 30° C., so as to suppress crystallization of the luminescent material (luminescent host and/or luminescent impurity material) included in the ink composition for an organic light-emitting device.

Although not particularly limited, a relative humidity during the forming of the coating film may be in a range of about 0.01 parts per million (ppm) to about 80%, for example, about 0.05 ppm to about 60%, and in another example, about 0.1 ppm to about 15%. In an embodiment, the relative humidity may be in a range of about 1 ppm to about 1%, for example, about 5 ppm to about 100 ppm. While not wishing to be bound by theory, it is understood that when the relative humidity is within this range, control of the conditions for forming the coating film is facilitated, and the amount of moisture adsorbed on the coating film, which may affect the coating film, may be reduced.

Drying

The obtained coating layer is dried to form the emission layer.

Although not particularly limited, a drying temperature may be room temperature (25° C.), or may be raised by heating. When heating is used, the drying temperature may be about 40° C. to about 130° C., for example, about 40° C. to about 80° C.

Also, a pressure during the drying may be a reduced pressure. For example, a reduced pressure condition of about 0.001 pascals (Pa) to about 100 Pa may be used.

Also, a drying time may be in a range of about 1 minute to about 90 minutes, for example, about 1 minute to about 30 minutes.

Process of Forming Other Layers

The other layers constituting the organic light-emitting device, for example, the anode, the hole injection layer, the hole transport layer, the electron transport layer, the electron injection layer, and the cathode, may be formed by appropriately selecting known methods.

For example, the anode and the cathode may be formed by deposition or sputtering.

Also, the hole injection layer, the hole transport layer, the electron transport layer, and the electron injection layer may be formed by vacuum deposition, spin coating, casting, inkjet printing, or Langmuir-Blodgett (LB) deposition.

Example of method of manufacturing organic light-emitting device

A method of manufacturing an organic light-emitting device may include:

forming an anode on a substrate;

forming an emission layer including the luminescent host material by coating the ink composition for an organic light-emitting device on the anode and drying the obtained coating film; and forming a cathode on the emission layer.

The expression "B on A" used herein may include a case in which A and B directly contact each other and a case in which A and B are spaced apart from each other.

The coating of the ink composition for an organic light-emitting device on the cathode may be performed by inkjet printing.

EXAMPLES

Hereinafter, embodiments of the present disclosure are described with reference to Examples, but are not limited thereto. Also, "%" means "weight percent" ("wt %"), unless otherwise defined in the Examples.

Synthesis Example 1: Synthesis of Compound 2-7

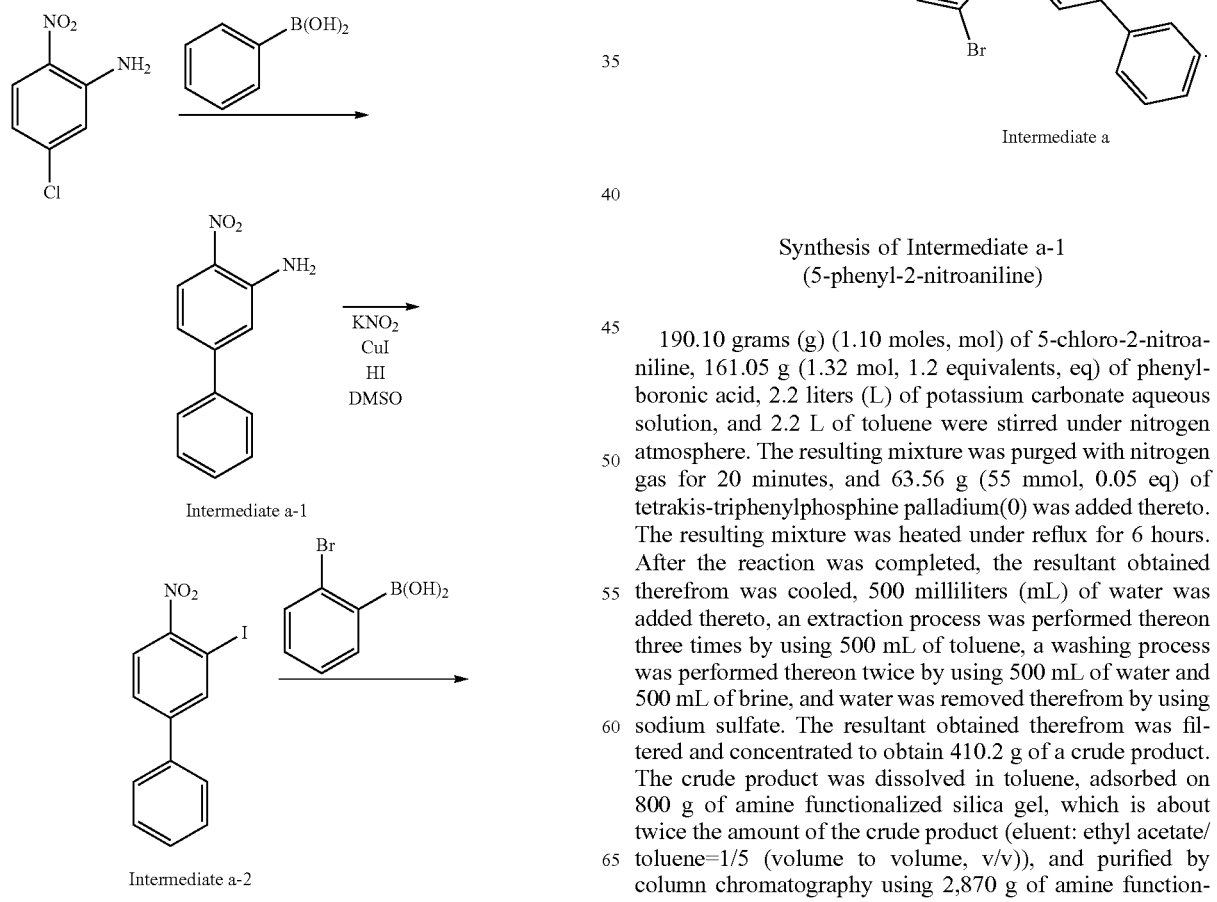

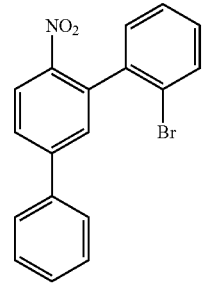

Intermediate a-3

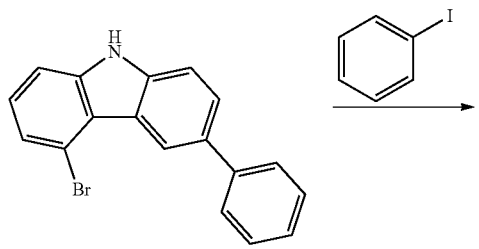

Intermediate a-4

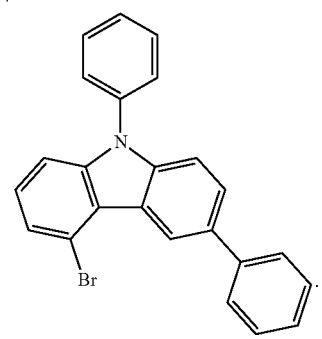

Intermediate a

Synthesis of Intermediate a-1
(5-phenyl-2-nitroaniline)

190.10 grams (g) (1.10 moles, mol) of 5-chloro-2-nitroaniline, 161.05 g (1.32 mol, 1.2 equivalents, eq) of phenylboronic acid, 2.2 liters (L) of potassium carbonate aqueous solution, and 2.2 L of toluene were stirred under nitrogen atmosphere. The resulting mixture was purged with nitrogen gas for 20 minutes, and 63.56 g (55 mmol, 0.05 eq) of tetrakis-triphenylphosphine palladium(0) was added thereto. The resulting mixture was heated under reflux for 6 hours. After the reaction was completed, the resultant obtained therefrom was cooled, 500 milliliters (mL) of water was added thereto, an extraction process was performed thereon three times by using 500 mL of toluene, a washing process was performed thereon twice by using 500 mL of water and 500 mL of brine, and water was removed therefrom by using sodium sulfate. The resultant obtained therefrom was filtered and concentrated to obtain 410.2 g of a crude product. The crude product was dissolved in toluene, adsorbed on 800 g of amine functionalized silica gel, which is about twice the amount of the crude product (eluent: ethyl acetate/toluene=1/5 (volume to volume, v/v)), and purified by column chromatography using 2,870 g of amine functionalized silica gel, which is about seven times the amount of the crude product, thereby obtaining Intermediate a-1 (yellow solid) (synthesized amount: 210 g, yield: 89%, purity (GC): 98%).

Synthesis of Intermediate a-2
(3-Iodo-4-nitro-1,1'-biphenyl)

221.31 g (1.03 mol) of Intermediate a-1 (5-phenyl-2-nitroaniline), 185.3 g (2.18 mol, 2.1 eq) of $KNO_2$ (potassium nitride), 187.0 g (0.982 mol, 1 eq) of cupper iodide (CuI), and 2.5 L of dimethylsulfoxide (DMSO) were stirred under nitrogen atmosphere. The resultant obtained therefrom was heated to a temperature of 60° C., and 1,976 g (8.5 mol, 8.23 eq) of 55% hydroiodic acid was added thereto dropwise for 30 minutes. The resulting mixture was stirred at a temperature of 60° C. for 30 minutes and cooled by stationary cooling and ice cooling. Then, 3 L of a potassium carbonate (1,078 g) aqueous solution was added to the reactant to stop the reaction. 2.5 L of diethyl ether was then added thereto and the organic layer was separated. The aqueous layer was extracted four times by using 2.0 L of diethyl ether, and the combined organic extracts were washed twice, each time with 3.0 L of water and 3.0 L of a sodium thiosulfate aqueous solution, and 2.0 L of brine. The extracts were dried by using sodium sulfate and concentrated to obtain 312.1 g of a crude product. The crude product was dissolved in dichloromethane, adsorbed on 624 g of silica gel, which is about twice the amount of the crude product (eluent: dichloromethane/hexane=1/10 (v/v)), and purified by column chromatography using 1,433 g of silica gel, which is about five times the amount of the crude product, thereby obtaining a target compound, that is, Intermediate a-2 (yellow crystal) (synthesized amount: 292 g, yield: 85%, purity (GC): 98%).

Synthesis of Intermediate a-3 (2-bromo-6'-nitro-1,1':3',1-terphenyl)

20.0 g (61.43 mmol) of Intermediate a-2 (3-iodo-4-nitro-1,1"-biphenyl) and 12.8 g (6,373 mmol) of o-bromophenylboronic acid were dissolved in a mixed solvent (86 ml/86 ml) of toluene/DME purged with nitrogen gas, and 1.42 g (1.23 mmol) of tetrakis-triphenylphosphine palladium(0) and 86 mL of 2 molar (M) sodium carbonate aqueous solution were added thereto in this order. The resulting mixture was heated under reflux for 10 hours. The resultant obtained therefrom was cooled to room temperature, and the organic layer was extracted therefrom twice by using 150 mL of pure water and 200 mL of toluene. The extracted organic layer was washed by using 200 mL of brine, and water was removed therefrom by using sodium sulfate. Filtering and concentration were performed thereon to obtain 23.2 g of a crude product. The crude product was purified by column chromatography by using 700 g of silica gel (eluent: hexane/toluene=1/1 (v/v)), and vacuum-dried at a temperature of 40° C. for 16 hours to obtain Intermediate a-3 (light yellow viscous liquid) (synthesized amount: 18.2 g, yield: 83%, purity (HPLC): 99.5%).

Synthesis of Intermediate a-4
(5-bromo-3-phenyl-9H-carbazole)

18.15 g (51.24 mmol) of Intermediate a-3 (2-bromo-6"-nitro-1,1":3",1-terphenyl) was dissolved in 110 mL of o-dichlorobenzene in an inert atmosphere, and 32.0 g (122.0 mmol) of triphenylphosphine was added thereto. The resulting mixture was stirred at a temperature of 180° C. for 20 hours. The outside temperature and pressure were respectively adjusted to 80° C. and 1 torr or less, and the stirring of the solvent was stopped to obtain 54.9 g of a viscous crude product. A mixture of hexane/toluene (=1/1 (v/v)) was added thereto to precipitate the target material. The target material was then filtered under reduced pressure and washed by using a mixture of hexane/toluene (=1/1 (v/v)). The filtrate obtained therefrom was concentrated to obtain 45.0 g of a crude product. The crude product was purified by column chromatography using 900 g of silica gel (eluent: hexane/toluene=1/1 (v/v)), and the solvent was removed therefrom to obtain 14.1 g of a light yellow viscous liquid. 50 mL of hexane was added to the light yellow viscous liquid, heated to a temperature of 60° C., and stirred to recover a precipitated target material. After drying for 15 hours under reduced pressure, Intermediate a-4 (light yellow solid) was obtained (synthesized amount: 13.5 g, yield: 81%, purity (HPLC): 99.1%).

Synthesis of Intermediate a (5-bromo-3,9-diphenyl-9H-carbazole)

13.46 g (41.78 mmol) of Intermediate a-4 (5-bromo-3-phenyl-9H-carbazole) and 9.50 g (46.57 mmol) of iodobenzene were mixed with 41 mL of 1,4-dioxane, and 0.40 g (2.09 mmol) of CuI, 0.96 g (8.41 mmol) of trans-1,2-diaminocyclohexane, and 2.02 g (21.02 mmol) of tert-BuONa were added thereto in this order. The resulting mixture was stirred at a temperature of 105° C. for 20 hours. The resulting mixture was cooled to room temperature, filtered under reduced pressure by using 10 g of celite, and washed by using dioxane to obtain a filtrate. The solvent was removed from the filtrate to obtain 25.30 g of a crude product. The crude product was dissolved in dichloromethane and adsorbed on 100 g of silica gel to remove the solvent. The crude product was then purified by column chromatography by using 400 g of the adsorption silica gel and an eluent of hexane/toluene (=1/1 (v/v)), and the solvent was removed therefrom. The resultant was vacuum-dried to obtain 14.6 g of Intermediate a (colorless solid) (yield: 88%, purity (HPLC): 99.0%).

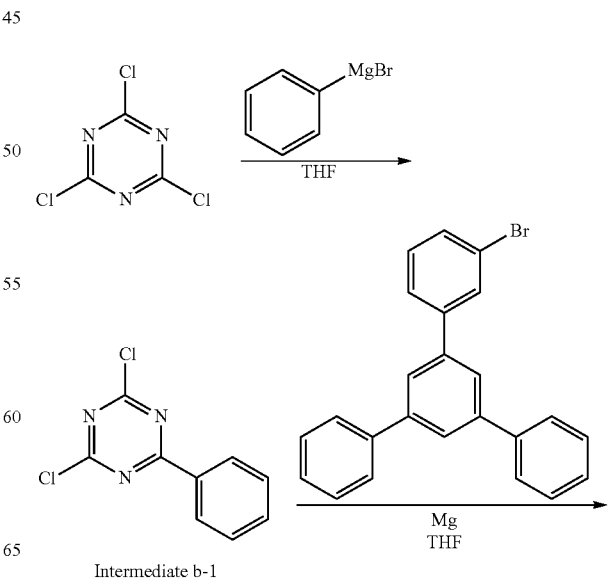

Intermediate b-1

-continued

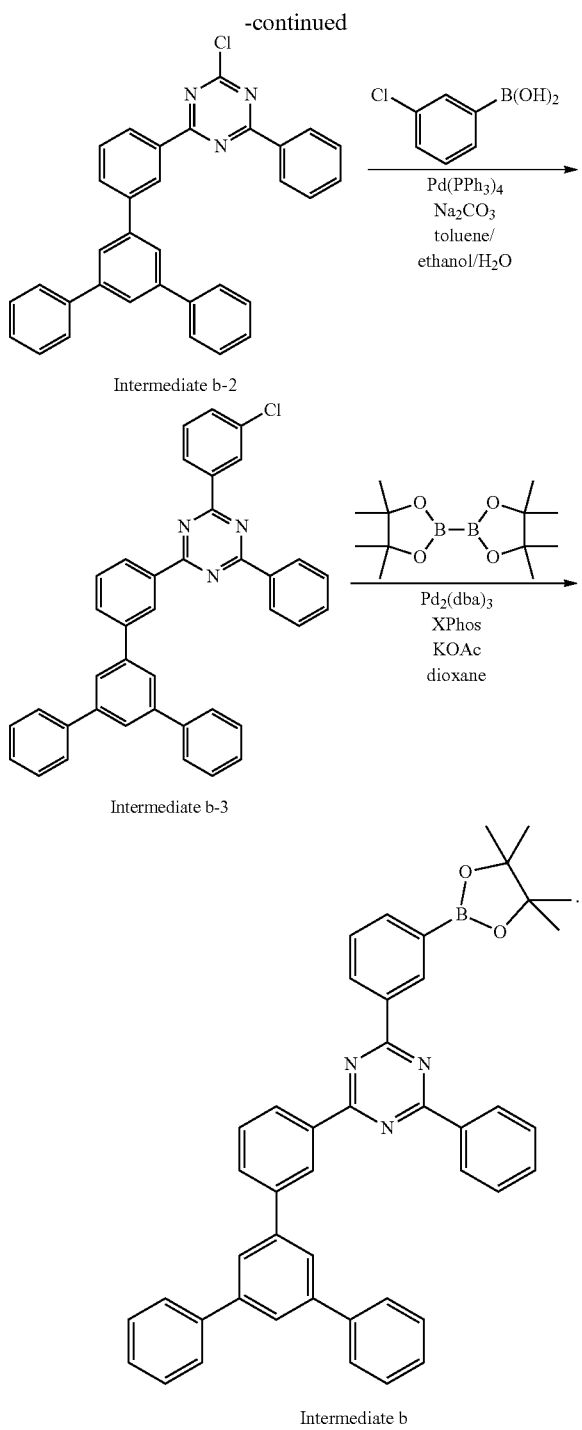

Intermediate b-2

Intermediate b-3

Intermediate b

Synthesis of Intermediate b-1 (2, 4-dichloro-6-phenyl-1,3,5-triazine)

30.0 g (162.7 mmol) of cyanuric acid was added to a 2-L round bottom flask, and the flask was evacuated and filled with argon three times by using a vacuum pump. 975 mL of dried toluene was then added to the flask and cooled to a temperature of 0° C. by using an ice bath. 29.5 g (162.3 mmol) of phenyl magnesium bromide and 54.2 mL of a dried diethyl ether solution were then added thereto dropwise under argon atmosphere. The mixture obtained therefrom was slowly warmed to room temperature and stirred for 2 hours, the reaction was terminated at a temperature of 0° C. by using 200 mL of 6 normal (N) HCl (aq.), and toluene was extracted therefrom. The organic layer collected therefrom was dried by using $MgSO_4$ and concentrated in a vacuum to obtain a crude product. The crude product was dissolved in THF and added to 200 mL of excess methanol to reprecipitate the crude product. This process was repeated twice. The crude product obtained therefrom was dissolved in THF and added to 100 mL of hexane to reprecipitate the crude product. The resultant obtained therefrom was vacuum-dried at a temperature of 40° C. for 5 hours to obtain Intermediate b-1 (light yellow-white solid) (synthesized amount 33.4 g, yield: 60%, purity (HPLC): 98.7%).

Synthesis of Intermediate b-2 (2-chloro-4-phenyl-6-(5'-phenyl-[1,1':3',1''-terphenyl]-3-yl)-1,3,5-triazine)

1.83 g (75.3 mmol) of Mg was added to a 300-mL round bottom flask, and the flask was evacuated and purged with argon three times by using a vacuum pump. 30 mL of dried THF was added to the flask and cooled to a temperature of −78° C. by using a dry ice ethanol bath. 29.0 g (75.3 mmol) of 3-bromo-5'-phenyl-1,1':3',1''-terphenyl and 166 mL of a dried THF solution were added thereto dropwise under argon atmosphere. The resultant obtained therefrom was slowly warmed to room temperature, stirred for 30 minutes, and slowly added dropwise to 196 mL of a dried THF solution containing 20.4 g (90.3 mmol) of 2,4-dichloro-6-phenyl-1,3,5-triazine at a temperature of 0° C. in a 1-L round bottom flask. The resultant obtained therefrom was slowly warmed to room temperature and stirred for 2 hours. After the reaction was completed at a temperature of 0° C., the reactant was extracted by using toluene to obtain an organic layer. The organic layer was dried by using $Na_2SO_4$ and vacuum-dried. The crude product obtained therefrom was dissolved in THF and added to excess methanol to reprecipitate the crude product. This process was repeated twice. The resultant obtained therefrom was dried at a temperature of 40° C. in a vacuum for 5 hours to obtain Intermediate b-2 (light yellow-white solid) (synthesized amount: 25.9 g, yield: 69%, purity (HPLC): 96.8%).

Synthesis of Intermediate b-3 (2-(3-chlorophenyl)-4-phenyl-6-(5'-phenyl-[1,1':3',1''-terphenyl]-3-yl)-1, 3,5-triazine)

19.5 g (39.3 mmol) of Intermediate b-3, 6.15 g (39.3 mmol) of (3-chlorophenyl)boronic acid, 0.91 g (0.79 mmol) of $Pd(PPh_3)_4$, and 12.5 g (118 mmol) of sodium carbonate were dissolved in 160 mL of toluene, mixed with 80 mL of ethanol and 160 mL of ultra-pure water in a 500-mL round bottom flask, and refluxed for 2 hours under argon atmosphere. After the reaction was completed, the mixture was added to 300 mL of pure water, and a precipitate was filtered and washed by methanol. The crude solid obtained therefrom was dissolved in toluene, and excess methanol was added thereto to reprecipitate the crude solid. The resultant obtained therefrom was dried at a temperature of 40° C. in a vacuum for 5 hours to obtain Intermediate b-3 (synthesized amount: 21.0 g, yield: 93%, purity (HPLC): 97.1%).

Synthesis of Intermediate b (2-phenyl-4-(5'-phenyl-[1,1':3',1''-terphenyl]-3-yl)-6-(3-(4,4,5,5-tetramethyl-1,3,2-dioxaborolan-2-yl)phenyl)-1,3,5-triazine 20.0 g (35.0 mmol) of Intermediate b-3, 17.8 g (69.9 mmol) of bis-(pinacolate)-diboron, 1.60 g (1.75 mmol) of Pd₂(dba)₃, 1.67 g (3.50 mmol) of XPhos, and 10.3 g (105 mmol) of potassium acetate were mixed with 350 mL of 1,4-dioxane in a round bottom flask and refluxed under argon atmosphere for 2 hours. After the reaction was completed, the mixture was filtered through celite and concentrated by a rotary evaporator to obtain a crude product. The crude product was purified by Si-gel column chromatography (a mixture of toluene and hexane was used as an eluent, and a mixing ratio thereof was gradually changed from ¼ to ⅙ (only toluene)) to obtain Intermediate b (white solid) (synthesized amount: 18.0 g, yield: 78%, purity (HPLC): 99.9%).

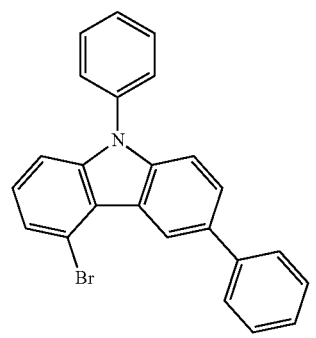

Intermediate a

+

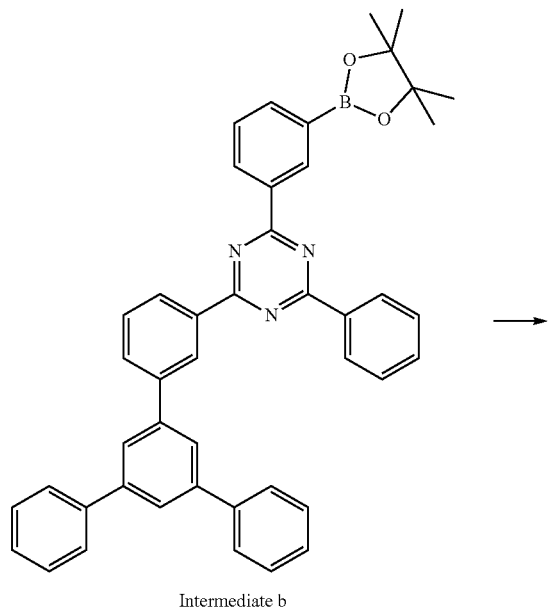

Intermediate b

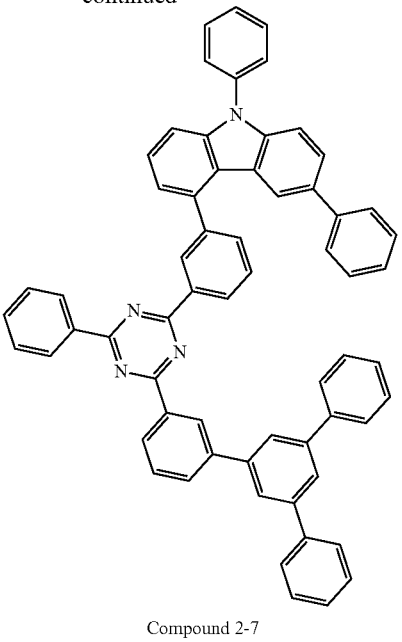

Compound 2-7

Synthesis of Compound 2-7

Under argon atmosphere, 2.20 g (5.52 mmol) of Intermediate a, 3.30 g (4.97 mmol) of Intermediate b, 0.078 g (0.11 mmol) of dichlorobis(triphenylphosphine)dipalladium, 55 ml of dioxane, and 28 mL of 0.5 N sodium carbonate aqueous solution were added to a reaction vessel and stirred at a temperature of 90° C. for 8 hours. After the reaction was completed, the mixture was cooled to room temperature and filtered through celite to obtain an organic layer. The organic layer was then concentrated and purified by column chromatography to obtain 2.97 g (yield: 69.9%) of Compound 2-7 (the structure thereof was identified by LC-MS). A glass transition temperature (Tg) was measured by using SII DSC6220 (manufactured by Seiko Instruments Inc.) based on JIS K 7121.

LC-MS, calcd for $C_{63}H_{42}N_4$=855, found m/z=855 (M⁺). Tg: 145.5° C.

Synthesis Example 2: Synthesis of Compound 3-5

Compound 3-5 was synthesized according to the Reaction Scheme below.

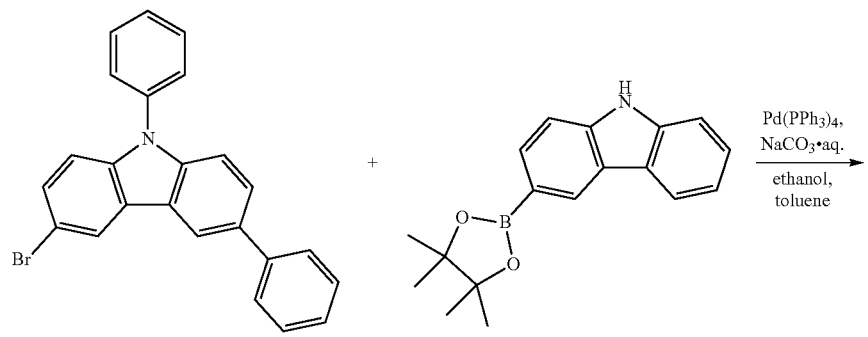

-continued

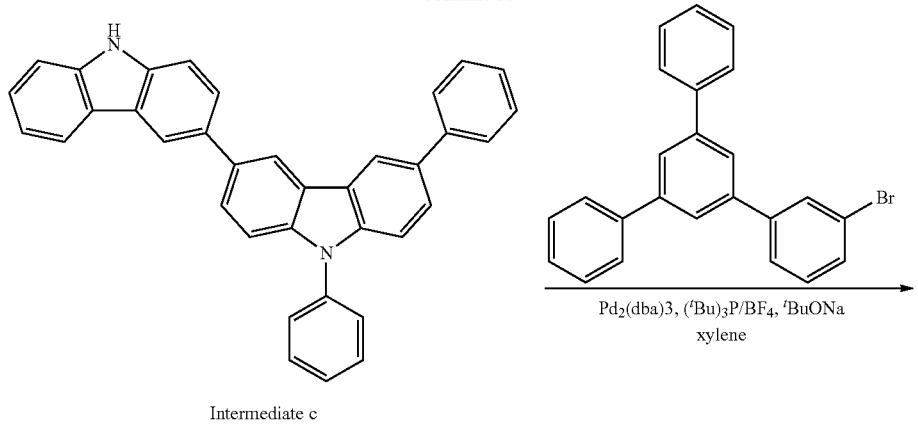

Intermediate c

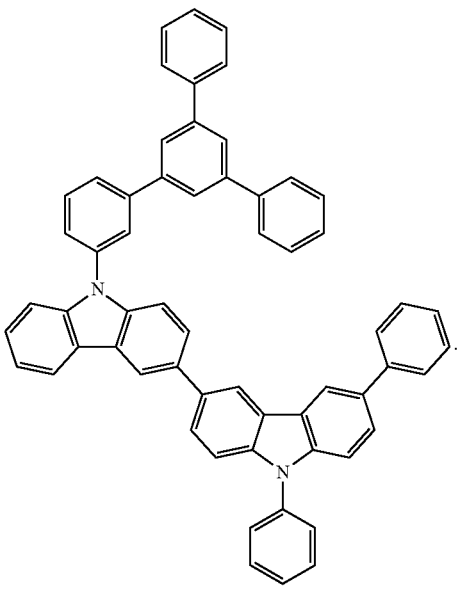

Compound 3-5

Synthesis of Intermediate c

Under argon atmosphere, 6.8 g (17.1 mmol) of 3-bromo-6,9-diphenylcarbazole(3-bromo-6,9-diphenylcarbazole), 5.0 g (17.1 mmol) of 3-(4,4,5,5-tetramethyl-1,3,2-dioxaborolan-2-yl)-9H-carbazole, 52 mL of toluene, 17 mL of ethanol, and 25 mL of 2 N sodium carbonate aqueous solution ($Na_2CO_3$ aq.) were mixed and stirred. 0.60 g (0.51 mmol) of tetrakistriphenylphosphine palladium ($Pd(PPh_3)_4$)) was then added thereto, and the mixture was refluxed for 8 hours. After the reaction was completed, the mixture was cooled to room temperature, and the product was extracted with toluene/water. The resultant was then purified by column chromatography to obtain 3.0 g (yield: 36%) of Intermediate c.

Synthesis of Compound 3-5

Under argon atmosphere, 3.0 g (6.19 mmol) of Intermediate c and 2.64 g (6.85 mmol) of 3-bromo-5"-phenyl-1,1': 3",1"-terphenyl were mixed with 26 mL of anhydrous xylene. 0.120 g (0.130 mmol) of tris(dibenzylideneacetone) dipalladium ($Pd_2(dba)_3$), 0.150 g (0.520 mmol) of tri-tert-butylphosphine tetrafluoroborate (($t-Bu)_3P/BF_4$), and 0.90 g (9.37 mmol) of sodium-t-butoxide (t-BuONa) were added, and the mixture was refluxed for 8 hours. The mixture was cooled to room temperature and filtered through celite. The product was then extracted with toluene and saturated saline solution. The resultant obtained therefrom was purified by column chromatography to obtain 2.0 g (yield: 41%) of light yellow Compound 3-5 (the structure thereof was identified by LC-MS).

LCMS, calcd for $C_{60}H_{40}N_2$=789, found m/z=789 ($M^+$).
Tg: 156.6° C.

Synthesis Example 3: Synthesis of Compound 3-35

Compound 3-35 was synthesized according to the Reaction Scheme below.

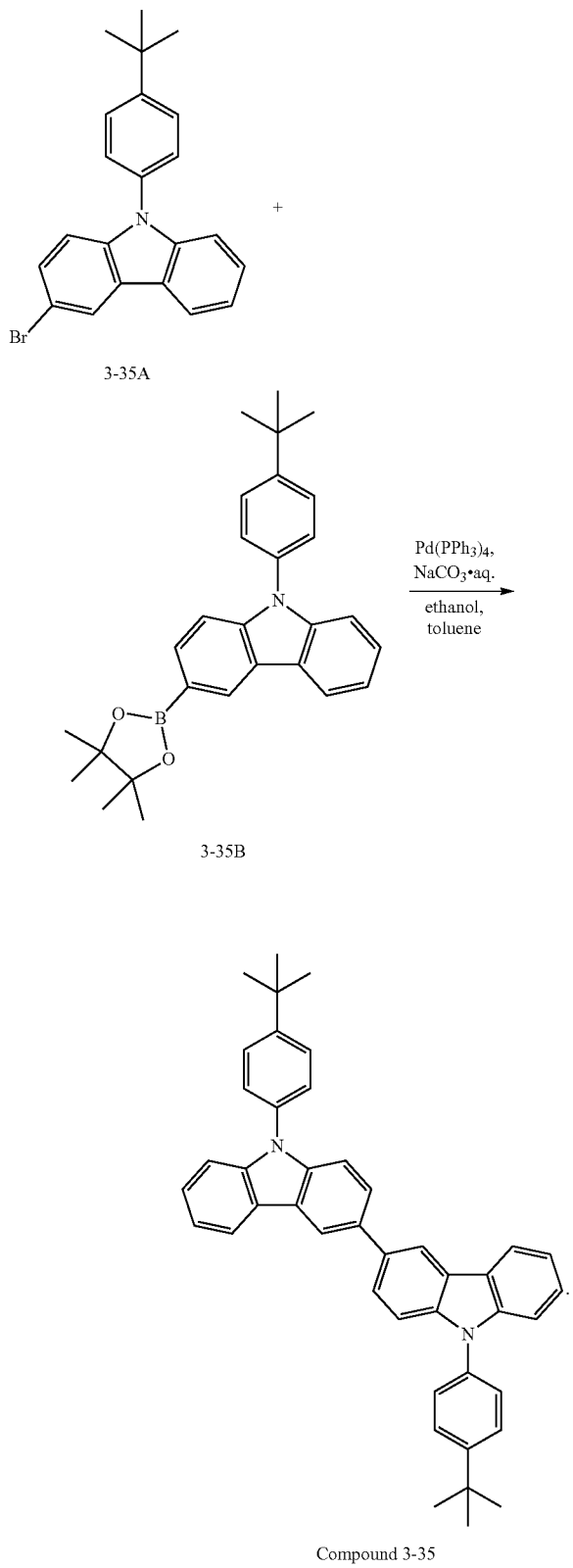

3-35A 3-35B

Compound 3-35

1.9 g (yield: 38%) of Compound 3-35 (the structure thereof was identified by LC-MS) was obtained in the same manner as Intermediate c in Synthesis Example 2, except that Compounds 3-35A and 3-35B were respectively used instead of 3-bromo-6,9-diphenylcarbazole and 3-(4,4,5,5-tetramethyl-1,3,2-dioxaborolan-2-yl)-9H-carbazole).

LCMS, calcd for $C_{60}H_{40}N_2$=597, found m/z=597 (M$^+$)
Tg: 136.0° C.

Example 1

A host (0.009 g of Compound 2-7 and 0.086 g of Compound 3-5) and a dopant (0.005 g of tris (2-(3-p-xylyl) phenyl)pyridine iridium)(III)) were added to 9.9 g butyl phenyl ether (vapor pressure: 0.21 millimeters of mercury, mmHg) to prepare an ink composition for an organic light-emitting device.

Example 2

An ink composition for an organic light-emitting device was prepared in the same manner as in Example 1, except that 1-propyl-4-methoxybenzene (vapor pressure: 0.11 mmHg) was used instead of butyl phenyl ether as a solvent.

Example 3

An ink composition for an organic light-emitting device was prepared in the same manner as in Example 1, except that ethyl benzoate (vapor pressure: 0.17 mmHg) was used instead of butyl phenyl ether as a solvent.

Example 4

An ink composition for an organic light-emitting device was prepared in the same manner as in Example 1, except that iso-propyl benzoate (vapor pressure: 0.11 mmHg) was used instead of butyl phenyl ether as a solvent.

Example 5

An ink composition for an organic light-emitting device was prepared in the same manner as in Example 1, except that 1-phenyl-1-butanone (butyrophenone) (vapor pressure: 0.12 mmHg) was used instead of butyl phenyl ether as a solvent.

Example 6

An ink composition for an organic light-emitting device was prepared in the same manner as in Example 1, except that p-methylacetophenone(4'-methylacetophenone) (vapor pressure: 0.18 mmHg) was used instead of butyl phenyl ether as a solvent.

Example 7

An ink composition for an organic light-emitting device was prepared in the same manner as in Example 1, except that Compound 3-35 was used instead of the mixture of Compound 2-7 and Compound 3-5 as a solvent.

Example 8

An ink composition for an organic light-emitting device was prepared in the same manner as in Example 7, except that ethyl benzoate (vapor pressure: 0.17 mmHg) was used instead of butyl phenyl ether as a solvent.

Example 9

An ink composition for an organic light-emitting device was prepared in the same manner as in Example 1, except that a mixture of ethyl benzoate and butyl phenyl ether (volume ratio of ethyl benzoate to butyl phenyl ether=7:3) was used instead of butyl phenyl ether as a solvent.

Comparative Example 1

An ink composition for an organic light-emitting device was prepared in the same manner as in Example 1, except that diethylene glycol ethyl methyl ether (vapor pressure: 0.96 mmHg) was used instead of butyl phenyl ether as a solvent.

Evaluation Example

Various performances were evaluated by using ink compositions for an organic light-emitting device, which were manufactured according to Examples 1 to 9 and Comparative Example 1.

Inkjet (IJ) Discharge Performance

By using an inkjet printer DMP2831 (manufactured by Fuji Film), the ink composition for an organic light-emitting device was discharged for 30 seconds, the discharging was stopped for 1 minute, and the ink composition was re-discharged. The evaluation of IJ discharge performance was performed based on the following criteria:

re-discharge possible, excellent droplet straightness: ◎
re-discharge possible, occurrence of droplet curve: ○
re-discharge impossible: X In this case, nozzle cleaning was performed under the following condition. That is, a nozzle head surface slightly contacted a cleaning pad mounted on an inkjet printer, and ink on a nozzle surface was suctioned.

Luminescent Efficiency

An organic light-emitting device was manufactured, and luminescent efficiency thereof was evaluated.

Manufacture and Evaluation of Organic Light-Emitting Device

A cleaned ITO substrate was exposed to UV/O$_3$, and poly(3,4-ethylenedioxythiophene)-poly(styrene sulfonic acid) (PEDOT-PSS) (manufactured by Sigma-Aldrich) was deposited by spin coating and heated in an atmosphere to a temperature of 180° C. for 15 minutes to form a hole injection layer having a thickness of 45 nanometers (nm). Then, 0.6 wt % of a xylene solution of HT-1 (Japanese Patent Publication No. 2014-001349, polymer Compound 8, additional test synthetic polymer $M_n$=28,000, $M_w$=122,000) was deposited on the hole injection layer by spin coating and dried under nitrogen atmosphere at a temperature of 230° C. for 30 minutes to form a hole transport layer having a thickness of 20 nm.

Then, each of the ink compositions for an organic light-emitting device according to Examples 1 to 9 and Comparative Example 1 was deposited on the hole transport layer by spin coating. After a pressure was reduced to $10^{-1}$ pascals (Pa), the ink composition was dried at a temperature of 0° C. for 15 minutes to form an emission layer having a thickness of 30 nm.

Then, HBL-1 was deposited in a vacuum condition of $5 \times 10^{-3}$ Pa HBL-1 to form a hole blocking layer having a thickness of 10 nm, (8-quinolinolato)lithium (LiQ) and KLET-03 (manufactured by Chemipro Kasei) were co-deposited on the hole blocking layer to form an electron transport layer having a thickness of 45 nm, and LiF was deposited on the electron transport layer to form an electron injection layer having a thickness of 0.5 nm. Then, aluminum was deposited on the electron injection layer to form a cathode having a thickness of 100 nm. Then, the substrate was loaded into a glove box and encapsulated by a glass substrate, thereby completing the manufacture of an organic light-emitting device.

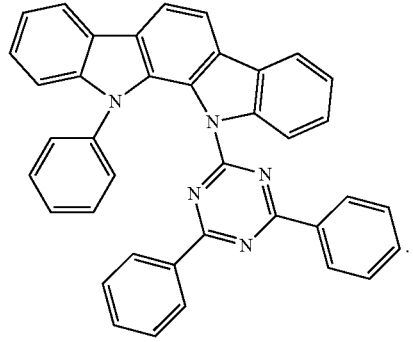

HBL-1

External power was connected to the organic light-emitting device, light emitted from the organic light-emitting device was measured by BM-9 (manufactured by Topcon Inc.), and luminescent efficiency was calculated from a current value at 6,000 candelas per square meter (cd/m$^2$). Evaluation results are shown in Table 1.

TABLE 1

| | Host compound No. | Solvent | Vapor pressure (mmHg) | Luminescent efficiency (cd/A) | IJ discharge stability |
|---|---|---|---|---|---|
| Example 1 | 2-7:3-5 | butyl phenyl ether | 0.21 | 83 | ◎ |
| Example 2 | 2-7:3-5 | 1-propyl-4-methoxybenzene | 0.11 | 80 | ◎ |
| Example 3 | 2-7:3-5 | ethyl benzoate | 0.17 | 75 | ◎ |
| Example 4 | 2-7:3-5 | Iso-propyl benzoate | 0.11 | 73 | ◎ |
| Example 5 | 2-7:3-5 | 1-phenyl-1-butanol | 0.12 | 72 | ○ |
| Example 6 | 2-7:3-5 | p-methyl-acetophenone | 0.18 | 68 | ○ |
| Example 7 | 3-35 | butyl phenyl ether | 0.21 | 48 | ○ |
| Example 8 | 3-35 | ethyl benzoate | 0.17 | 45 | ○ |
| Example 9 | 2-7:3-5 | ethyl benzoate:butyl phenyl ether | 0.18 | 78 | ◎ |
| Comparative Example 1 | 2-7:3-5 | diethylene glycol ethyl methyl ether | 0.96 | 32 | X |

TABLE 1-continued

| Host compound No. | Solvent | Vapor pressure (mmHg) | Luminescent efficiency (cd/A) | IJ discharge stability |
|---|---|---|---|---|

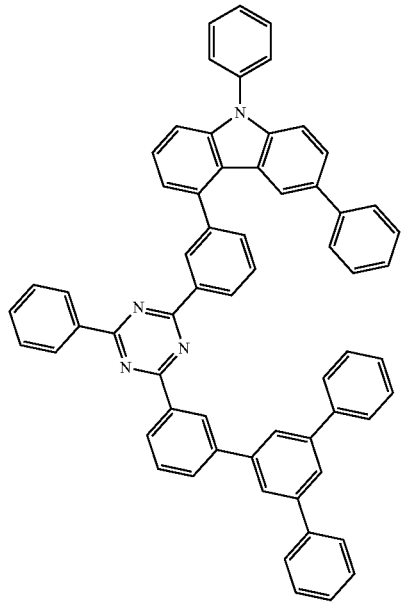

Compound 2-7

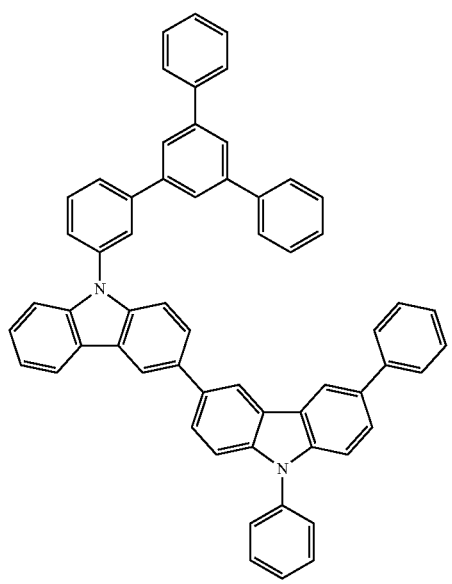

Compound 3-5

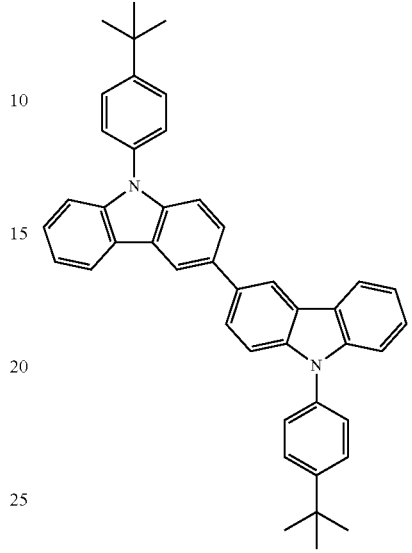

Compound 3-35

Referring to Table 1, it has been determined that the ink compositions prepared according to Examples 1 to 9 have excellent inkjet discharge stability, as compared with the ink composition prepared by using a non-aromatic solvent according to Comparative Example 1. Also, it is confirmed that high luminescent efficiency is exhibited when an aromatic solvent having a vapor pressure of about 1 mmHg is used.

As described above, the ink composition for an organic light-emitting device has excellent inkjet discharge stability, and accordingly, an organic light-emitting device, which includes a film formed by using the ink composition, may have high luminescent efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. An ink composition for an organic light-emitting device, the ink composition comprising a luminescent host material and a solvent,
   wherein the luminescent host material comprises at least one compound represented by Formula (1), and at least one compound represented by Formula (3), and,
   wherein the solvent comprises at least one selected from an aromatic ether, an aromatic ester, and an aromatic ketone:

Formula (1)

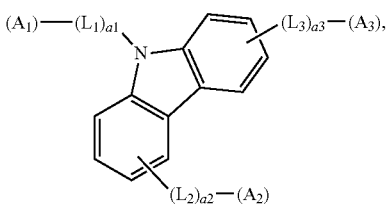

Formula (3)

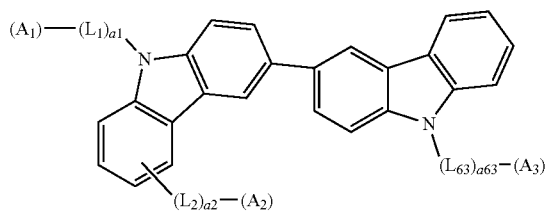

wherein, in Formulae (1) and (3)

$L_2$ and $L_3$ are each independently selected from a single bond, *—O—*', *—S—*', *—N($R_5$)—*', a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_1$ and $L_{63}$ are each independently selected from a single bond, *—O—*', *—S—*', a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 to a3 and a63 are each independently an integer from 1 to 10, $A_1$ to $A_3$ are each independently selected from hydrogen, deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —C(=O)($Q_1$), at least one of $A_1$ to $A_3$ in Formula (1) is a group represented by Formula (2-A):

Formula (2-A)

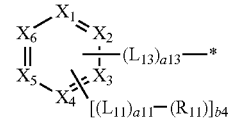

wherein, in Formula (2-A), $X_1$ is N, carbon linked to *-($L_{11}$)$_{a11}$-($R_{11}$), or carbon linked to $L_{13}$; $X_2$ is N, carbon linked to *-($L_{11}$)$_{a11}$-($_{11}$), or carbon linked to $L_{13}$; $X_3$ is N, carbon linked to *-($L_{11}$)$_{a11}$-($R_{11}$), or carbon linked to $L_{13}$; $X_4$ is N, carbon linked to *-($L_{11}$)$_{a11}$-($R_{11}$), or carbon linked to $L_{13}$; $X_5$ is N, carbon linked to *-($L_{11}$)$_{a11}$-($R_{11}$), or carbon linked to $L_{13}$; and $X_6$ is N, carbon linked to *-($L_{11}$)$_{a11}$-($R_{11}$), or carbon linked to $L_{13}$, at least one of $X_1$ to $X_6$ is N, $L_{11}$ and $L_{13}$ are each independently selected from a single bond, *—O—*', *—S—*', *—N($R_5$)—*', a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 and a13 are each independently an integer from 1 to 10, $R_5$ is selected from hydrogen, deuterium, a $C_1$-$C_{10}$ alkyl group represented by Formulae 7-1 to 7-57, and group represented by Formulae 8-1 to 8-7

7-1

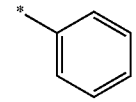

7-2

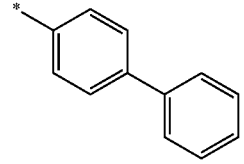

7-3

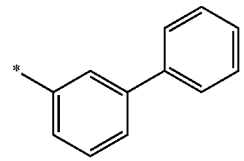

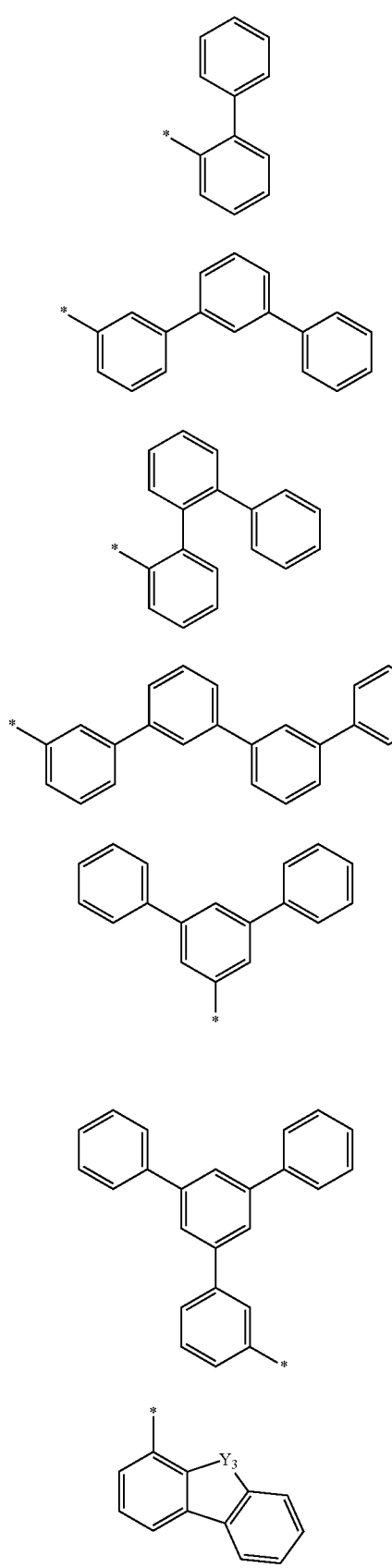
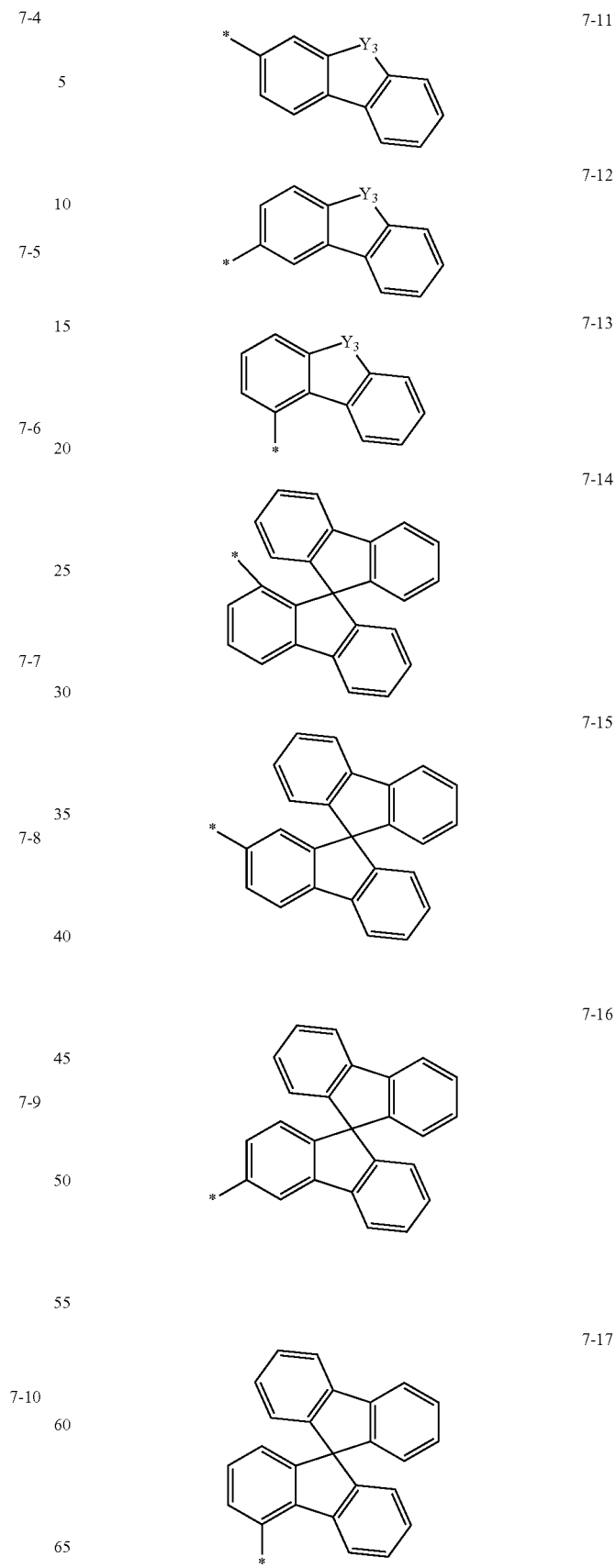

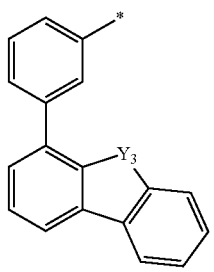
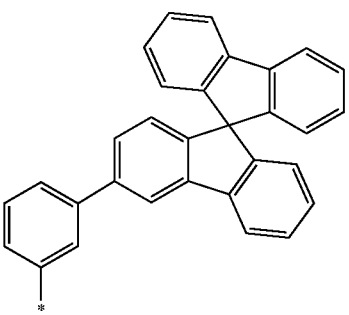

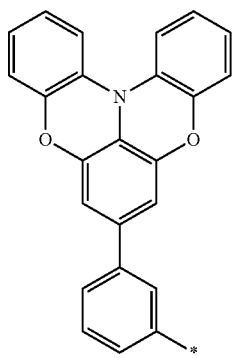
7-29
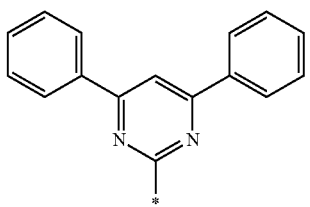
7-30
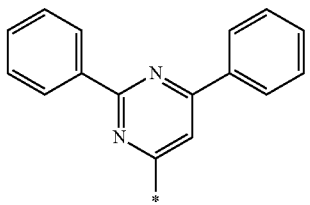
7-31
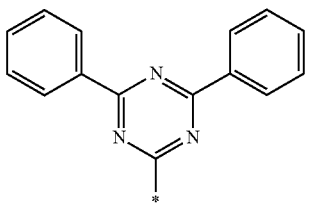
7-32
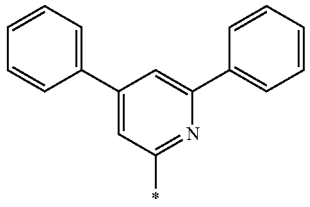
7-33
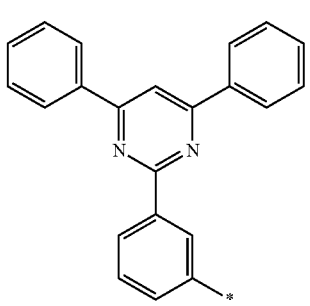
7-34
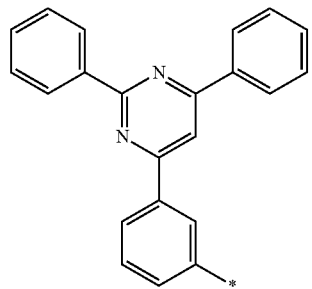
7-35
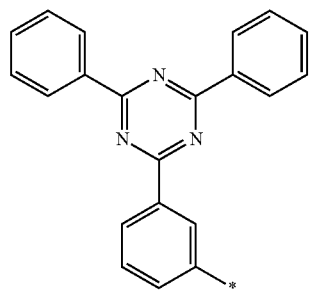
7-36
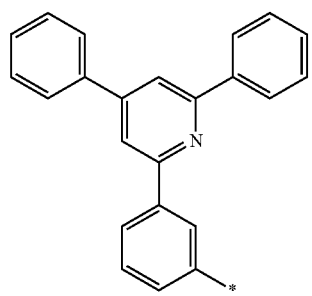
7-37
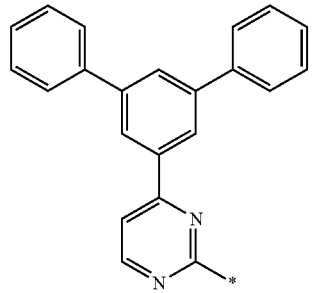
7-38
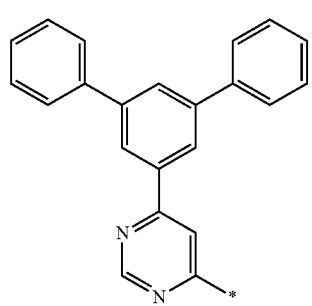
7-39

-continued
7-40
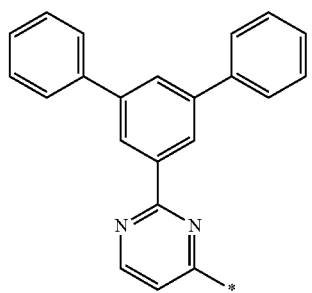
7-41
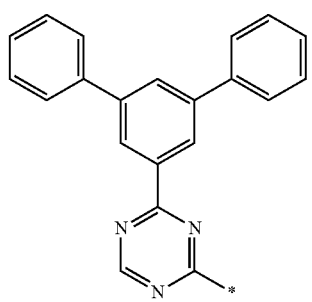
7-42
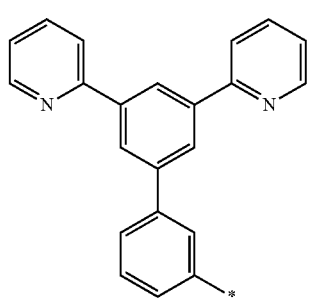
7-43
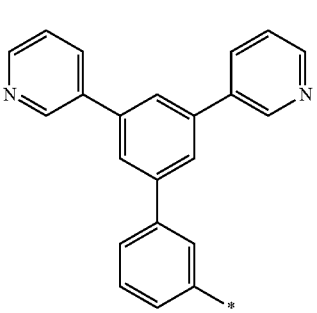
7-44
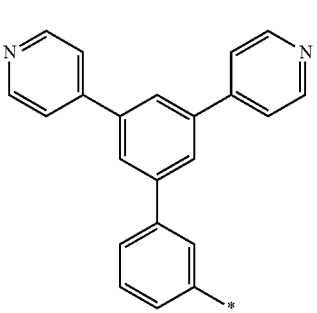
-continued
7-45
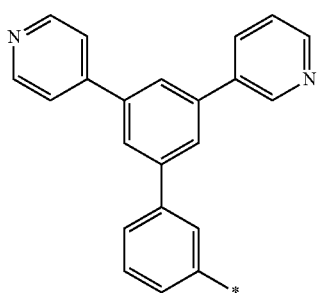
7-46
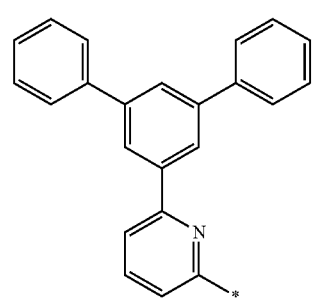
7-47
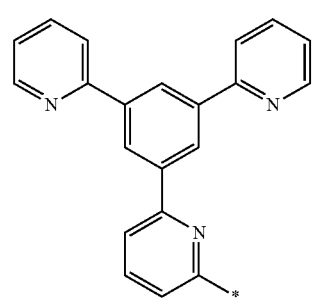
7-48
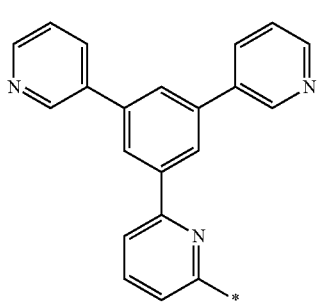
7-49
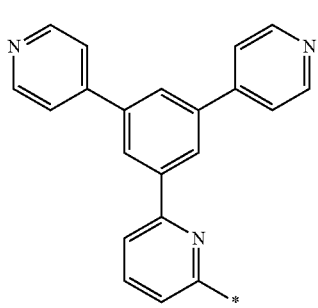

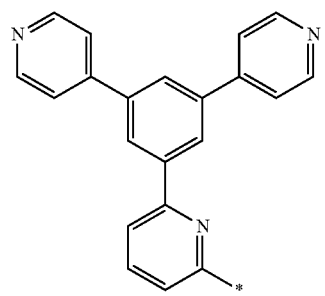
7-49
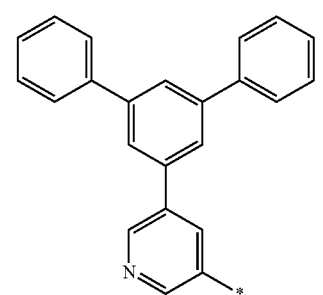
7-50
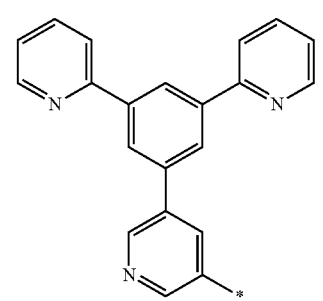
7-51
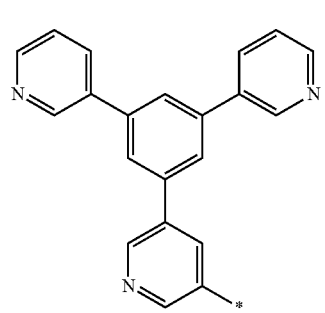
7-52
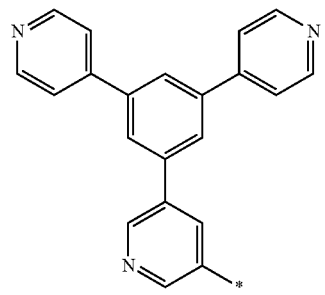
7-53
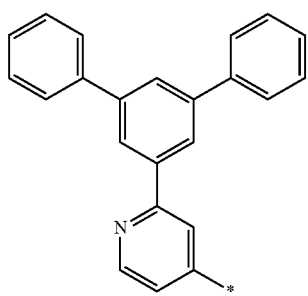
7-54
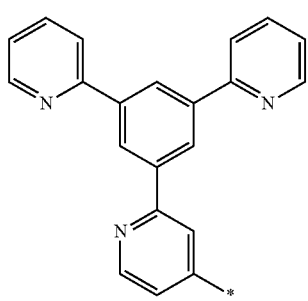
7-55
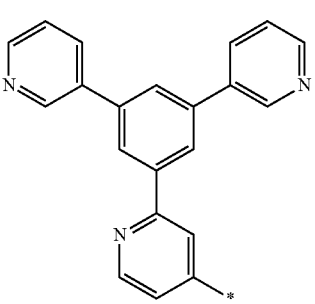
7-56
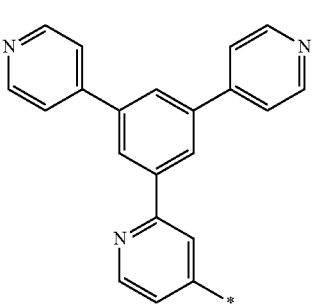
7-57
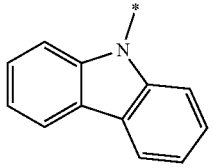
8-1
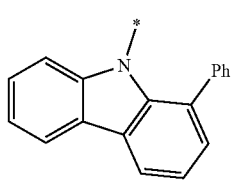
8-2

-continued

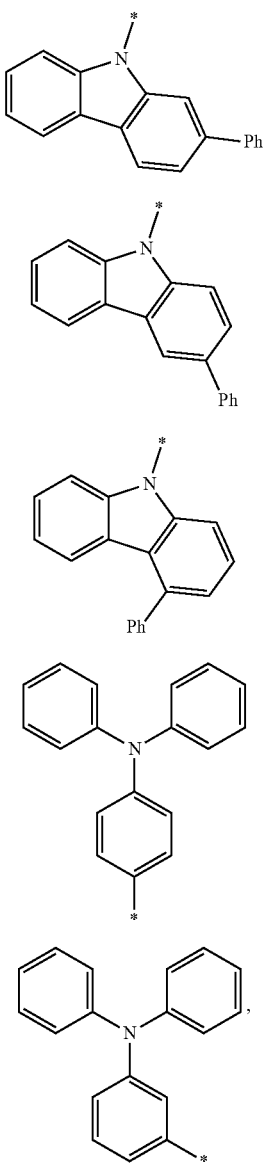

8-3

8-4

8-5

8-6

8-7

$R_{11}$ is selected from hydrogen, deuterium, —F, —Cl, —Br, —I, —CD$_3$, —CD$_2$H, -CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_1$)(Q$_2$), and —C(=O)(Q$_1$), two or more neighboring groups selected from a plurality of groups $R_{11}$ are optionally linked to form a substituted or unsubstituted $C_5$-$C_{30}$ carbocyclic group or a substituted or unsubstituted $C_2$-$C_{30}$ heterocyclic group, b4 is an integer from 0 to 4, and

* indicates a binding site to a neighboring atom, any neighboring groups in $A_1$ to $A_3$ are optionally linked to form a substituted or unsubstituted $C_5$-$C_{30}$ carbocyclic group or a substituted or unsubstituted $C_2$-$C_{30}$ heterocyclic group, provided that *-(L$_2$)$_{a2}$-(A$_2$) and *-(L$_3$)$_{a3}$-(A$_3$) in Formula (1) are not hydrogen at the same time, at least one substituent of the substituted $C_2$-$C_{60}$ alkylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_5$-$C_{30}$ carbocyclic group, and the substituted $C_2$-$C_{30}$ heterocyclic group is selected from:

deuterium, —F, —Cl, —Br, —I, —CD$_3$, —CD$_2$H, —CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{11}$)(Q$_{12}$), and —C(=O)(Q$_{11}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), and —C(=O)($Q_{21}$); and —Si($Q_{31}$)($Q_{32}$)($Q_{33}$), —N($Q_{31}$)($Q_{32}$), and —C(=O)($Q_{31}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

2. The ink composition of claim 1, wherein the compound represented by Formula (1) is represented by Formula (2):

Formula (2)

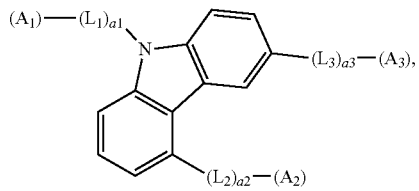

wherein, in Formula (2), $L_1$ to $L_3$, a1 to a3, and $A_1$ to $A_3$ are each independently the same as described in claim 1, and at least one of $A_1$ to $A_3$ is a group represented by Formula (2-A):

Formula (2-A)

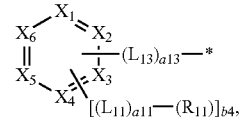

wherein, in Formula (2-A), $X_1$ is N, carbon linked to *-($L_{11}$)$_{a11}$-($R_{11}$), or carbon linked to $L_{13}$; $X_2$ is N, carbon linked to *-($L_{11}$)$_{a11}$-($R_{11}$), or carbon linked to $L_{13}$; $X_3$ is N, carbon linked to *-($L_{11}$)$_{a11}$-($R_{11}$), or carbon linked to $L_{13}$; $X_4$ is N, carbon linked to *-($L_{11}$)$_{a11}$-($R_{11}$), or carbon linked to $L_{13}$, $X_5$ is N, carbon linked to *-($L_{11}$)$_{a11}$-($R_{11}$), or carbon linked to $L_{13}$; $X_6$ is N, carbon linked to *-($L_{11}$)$_{a11}$-($R_{11}$), or carbon linked to $L_{13}$, at least one of $X_1$ to $X_6$ is N, $L_{11}$ and $L_{13}$ are the same as described in connection with $L_1$ in claim 1, a11 and a13 are the same as described in connection with a1 in claim 1, $R_{11}$ is the same as described in connection with $A_1$ in claim 1, two or more neighboring groups selected from a plurality of groups $R_{11}$ are optionally linked to form a substituted or unsubstituted $C_5$-$C_{30}$ carbocyclic group or a substituted or unsubstituted $C_2$-$C_{30}$ heterocyclic group, b4 is an integer from 0 to 4, and

* indicates a binding site to a neighboring atom.

3. The ink composition of claim 1, wherein in Formula (3) $L_1$, $L_2$, and $L_{63}$ are each independently selected from:

a single bond; and a phenylene group, a fluorenylene group, a spiro-bifluorenylene group, a carbazolylene group, a dibenzofuranylene group, and a dibenzothiophenylene group, each substituted or unsubstituted with at least one selected from deuterium, —$CD_3$, —$CD_2H$, —$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group, a1, a2, and a63 are each independently 1, 2, or 3, $A_1$, $A_2$, and $A_{63}$ are each independently selected from:

hydrogen, deuterium, —$CD_3$, —$CD_2H$, —$CDH_2$, a $C_1$-$C_{20}$ alkyl group, and a $C_1$-$C_{20}$ alkoxy group; and a phenyl group, a fluorenyl group, a spiro-bifluorenyl group, a carbazolyl group, a dibenzofuranyl group, and a dibenzothiophenyl group, each substituted or unsubstituted with at least one selected from deuterium, —$CD_3$, —$CD_2H$, —$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

4. The ink composition of claim 1, wherein in Formulae (1) and (3), $L_1$ to $L_3$ and $L_{63}$ are each independently selected from a single bond and groups represented by Formulae 6-1 to 6-27;

Formula 6-1

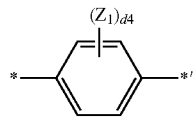

Formula 6-2

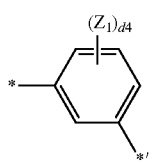

Formula 6-3

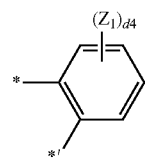

Formula 6-4

Formula 6-5

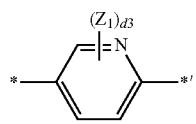

Formula 6-6

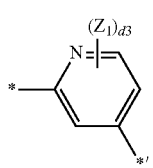

Formula 6-7

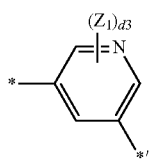

Formula 6-8

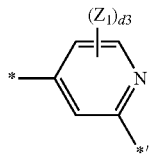

Formula 6-9

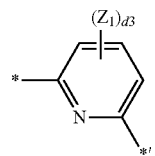

Formula 6-10

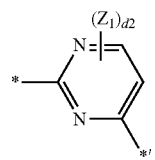

Formula 6-11

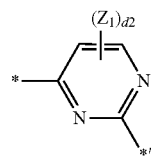

Formula 6-12

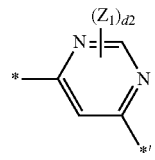

Formula 6-13

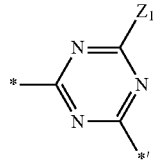

Formula 6-14

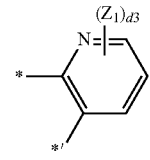

Formula 6-15

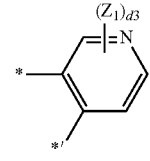

Formula 6-16

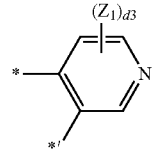

Formula 6-17

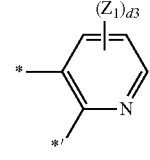

-continued

Formula 6-18

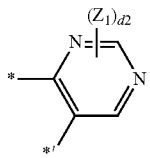

Formula 6-19

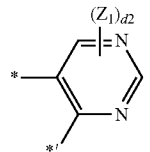

Formula 6-20

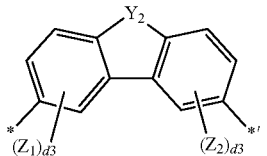

Formula 6-21

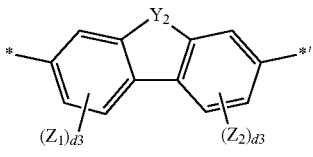

Formula 6-22

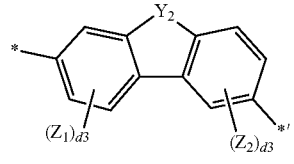

Formula 6-23

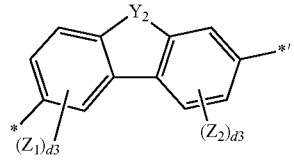

Formula 6-24

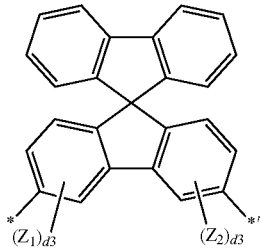

Formula 6-25

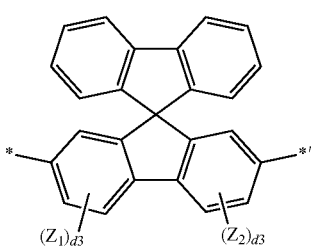

-continued

Formula 6-26

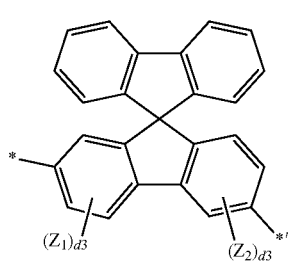

Formula 6-27

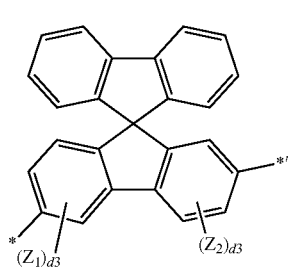

wherein in Formulae 6-1 to 6-27, $Y_2$ may be O, S, $C(Z_3)(Z_4)$, or $N(Z_5)$, $Z_1$ to $Z_5$ may each independently be hydrogen, deuterium, —$CD_3$, —$CD_2H$, —$CDH_2$, a $C_1$-$C_{20}$ alkyl group, a $C_1$-$C_{20}$ alkoxy group, a phenyl group, a biphenyl group, a trimethylsilyl group, or a triphenylsilyl group, d2 may be 1 or 2, d3 may be 1, 2, or 3, d4 may be 1, 2, 3, or 4, and \* and \*' each indicate a binding site to a neighboring atom.

5. The ink composition of claim 1, wherein a molecular weight of the luminescent host material is 2,000 grams per mole or less.

6. The ink composition of claim 1, wherein the aromatic ether comprises a compound represented by Formula (4), the aromatic ester comprises a compound represented by Formula (5), and the aromatic ketone comprises a compound represented by Formula (6):

Formula (4)

(4)

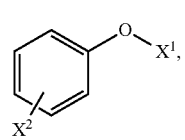

wherein, in Formula (4), $X^1$ is a $C_1$-$C_6$ alkyl group, and $X^2$ is a hydrogen atom, a methyl group, an ethyl group, or a propyl group, Formula (5)

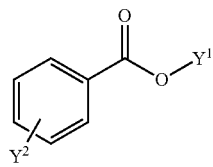
(5)

wherein, in Formula (5), $Y^1$ is a $C_1$-$C_3$ alkyl group, and $Y^2$ is a hydrogen atom, a methyl group, or an ethyl group, and Formula (6)

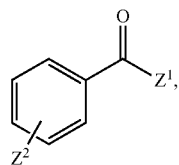
(6)

wherein, in Formula (6), $Z^1$ is a $C_1$-$C_4$ alkyl group, and $Z^2$ is a hydrogen atom, a methyl group, or an ethyl group.

7. The ink composition of claim 1, wherein the solvent comprises two or more different compounds selected from an aromatic ether, an aromatic ester, and an aromatic ketone.

8. The ink composition of claim 1, wherein the solvent comprises at least one of an aromatic ether and an aromatic ester.

9. The ink composition of claim 1, wherein a vapor pressure of the solvent at a temperature of 25°C. is 1 millimeter of mercury or less.

10. The ink composition of claim 1, further comprising a phosphorescent dopant or a fluorescent dopant.

11. The ink composition of claim 1, wherein the ink composition is an ink composition for inkjet printing.

12. An organic light-emitting device comprising:
an anode;
an emission layer; and
a cathode,
wherein the emission layer is an organic film formed by using the ink composition of claim 1,
wherein the emission layer comprises a luminescent host material, and
wherein the luminescent host material comprises at least one compound represented by Formula (1) and at least one compound represented by Formula (3).

13. The organic light-emitting device of claim 12, wherein the emission layer further comprises a phosphorescent dopant or a fluorescent dopant.

14. A method of manufacturing an organic light-emitting device, the method comprising:
forming an anode on a substrate;
forming an emission layer comprising the luminescent host material by coating the ink composition of claim 1 on the anode and drying the obtained coating film; and
forming a cathode on the emission layer.

15. The method of claim 14, wherein the coating of the ink composition on the anode is performed by inkjet printing.

* * * * *